(12) United States Patent
Mizuno et al.

(10) Patent No.: US 7,291,730 B2
(45) Date of Patent: Nov. 6, 2007

(54) PYRIMIDINE COMPOUNDS AND THEIR USE

(75) Inventors: Hajime Mizuno, Minoo (JP); Noriyasu Sakamoto, Toyonaka (JP); Yoshiharu Kinoshita, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 425 days.

(21) Appl. No.: 10/964,618

(22) Filed: Oct. 15, 2004

(65) Prior Publication Data

US 2005/0107609 A1    May 19, 2005

Related U.S. Application Data

(62) Division of application No. 10/344,318, filed as application No. PCT/JP01/07766 on Sep. 7, 2001, now Pat. No. 6,838,463.

(30) Foreign Application Priority Data

Sep. 19, 2000  (JP) ............... 2000-283113
May 14, 2001  (JP) ............... 2001-142975

(51) Int. Cl.
  *C07D 239/30*   (2006.01)
(52) U.S. Cl. ............... 544/319; 544/326; 544/334
(58) Field of Classification Search ............... 544/319, 544/326, 334
  See application file for complete search history.

(56) References Cited

U.S. PATENT DOCUMENTS

| 3,778,441 A | 12/1973 | Burckhardt et al. |
| 3,907,797 A | 9/1975 | Budesinsky et al. |
| 4,402,730 A | 9/1983 | Milzner |
| 5,945,426 A * | 8/1999 | Chokai et al. ............... 514/269 |

FOREIGN PATENT DOCUMENTS

| CN | 87103906 A | 2/1988 |
| DE | 40 29 654 | 4/1992 |
| DE | 40 31 798 | 4/1992 |
| EP | 0 506 269 | 9/1992 |
| EP | 0 972 770 | 1/2000 |
| GB | 1264621 | * 2/1972 |
| GB | 2 078 222 | 1/1982 |
| JP | 4-95077 | 3/1992 |
| WO | WO97/14684 | 4/1997 |

OTHER PUBLICATIONS

Baram et al., CAPLUS Abstract No. 99:5069, 1983.*
Chemical Abstracts, vol. 131, No. 9, 1999. Columbus, Ohio, US; abstracts No. 116250j, XP002191469.

* cited by examiner

*Primary Examiner*—Deepak Rao
(74) *Attorney, Agent, or Firm*—Sughrue Mion Pllc.

(57) ABSTRACT

Pyrimidine compounds of formula (1):

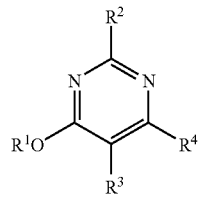

(1)

wherein $R^1$ is $C_3$-$C_7$ alkynyl optionally substituted with halogen; $R^2$ and $R^3$ are independently hydrogen or the like; and $R^4$ is $C_3$-$C_7$ alkynyloxy optionally substituted with halogen, optionally substituted phenyl, or the like have an excellent pesticidal effect.

4 Claims, No Drawings

PYRIMIDINE COMPOUNDS AND THEIR USE

This application is a divisional of application Ser. No. 10/344,318 filed Feb. 11, 2003 now U.S. Pat. No. 6,838,463 which is a 371 of PCT/JP01/07766 filed Sep. 7, 2001; the disclosure of which is incorporated herein by reference.

TECHNICAL FIELD

The present invention relates to certain pyrimidine compounds and their use.

BACKGROUND ART

Various compounds have been used in the past for the purpose of pest control. However, since not all these compounds have a satisfactory effect, there has been a demand for the development of compounds which are novel as pesticides and have a satisfactory effect.

It is an object of the present invention to provide novel compounds having a pesticidal effect and pesticidal compositions characterized in that these compounds are contained as active ingredients.

DISCLOSURE OF THE INVENTION

The present inventors have extensively studied in order to search for compounds having an excellent pesticidal effect. As a result, they have found that the compounds of formula (1) as depicted below have pesticidal activity, thereby completing the present invention.

That is, the present invention provides pyrimidine compounds of formula (1):

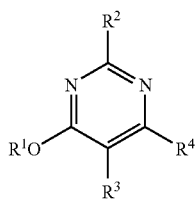

(hereinafter referred to as the present compound(s))
wherein $R^1$ is $C_3$-$C_7$ alkynyl optionally substituted with halogen;

$R^2$ and $R^3$ are independently hydrogen, halogen or $C_1$-$C_4$ alkyl; and $R^4$ is $C_3$-$C_7$ alkynyloxy optionally substituted with halogen; $C_3$-$C_8$ cycloalkoxy optionally substituted with halogen, hydroxy, $C_1$-$C_4$ alkyl or $C_1$-$C_4$ alkoxy; ethynyl substituted with $C_3$-$C_5$ alkyl; or a group of formula -$A^1R^5$ wherein $A^1$ is a single bond, oxygen, sulfur, carbonyl,

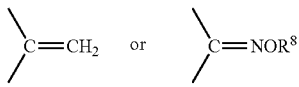

wherein $R^8$ is $C_1$-$C_4$ alkyl; when $A^1$ is a single bond oxygen, or sulfur, then $R^5$ is optionally substituted phenyl or optionally substituted $C_7$-$C_9$ aralkyl; or when $A^1$ is carbonyl,

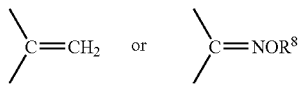

wherein $R^8$ is $C_1$-$C_4$ alkyl, then $R^5$ is optionally substituted phenyl; or a group of formula —$NR^6R^7$ wherein $R^6$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted with $C_7$-$C_9$ aralkyl; and $R^7$ is hydrogen, $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl;

wherein the substituent in the optionally substituted phenyl and in the optionally substituted $C_7$-$C_9$ aralkyl is at least one selected from halogen, hydroxy, cyano, nitro, phenyl, phenoxy, $C_1$-$C_4$ alkyl, $C_1$-$C_4$ haloalkyl, $C_1$-$C_4$ alkoxy, $C_1$-$C_4$ haloalkoxy, $C_1$-$C_3$ alkylthio, $C_1$-$C_4$ haloalkylthio, $C_3$-$C_7$ alkynyloxy, $C_2$-$C_6$ (alkoxyalkoxy), $C_2$-$C_6$ (alkylcarbonyl), and $C_2$-$C_6$ (alkylcarbonyloxy).

The present invention further provides pesticidal compositions containing the present compounds as active ingredients.

MODE FOR CARRYING OUT THE INVENTION

The $C_3$-$C_7$ alkynyl optionally substituted with halogen, which is represented by $R^1$, may include 2-propynyl, 2-butynyl, 3-butynyl, 2-pentynyl, 3-pentynyl, 2-heptynyl, 4,4-dimethyl-2-pentynyl, 3-fluoro-2-propynyl, 3-chloro-2-propynyl, 3-bromo-2-propynyl, 3-iodo-2-propynyl, 3-trifluoromethyl-2-propynyl, 1-methyl-2-propynyl, 1-methyl-2-butynyl, 4-fluoro-2-butynyl, 4-chloro-2-butynyl, 4,4-difluoro-2-butynyl, and 1,1-dimethyl-2-propynyl.

The $C_1$-$C_4$ alkyl, which is represented by $R^2$ or $R^3$, may include methyl, ethyl, propyl, 1-methylethyl, butyl, 1-methylpropyl, 2-methylpropyl, and 1,1-dimethylethyl.

The $C_3$-$C_7$ alkynyloxy optionally substituted with halogen, which is represented by $R^4$, may include 2-propynyloxy, 2-butynyloxy, 3-butynyloxy, 2-pentynyloxy, 3-pentynyloxy, 2-heptynyloxy, 4,4-dimethyl-2-pentynyloxy, 3-fluoro-2-propynyloxy, 3-chloro-2-propynyloxy, 3-bromo-2-propynyloxy, 3-trifluoromethyl-2-propynyloxy, 1-methyl-2-propynyloxy, 1-methyl-2-butynyloxy, 4-fluoro-2-butynyloxy, 4-chloro-2-butynyloxy, 4,4-difluoro-2-butynyloxy, and 1,1-dimethyl-2-propynyloxy.

The $C_3$-$C_8$ cycloalkoxy optionally substituted with halogen, hydroxy, $C_1$-$C_4$ alkyl, or $C_1$-$C_4$ alkoxy, which is represented by $R^4$, may include cyclopropoxy, cyclopentyloxy, 2-methylcyclopentyloxy, cyclohexyloxy, 1-methylcyclohexyloxy, 2-methylcyclohexyloxy, 3-methylcyclohexyloxy, 4-methylcyclohexyloxy, 2-fluorocyclohexyloxy, 3-fluorocyclohexyloxy, 4-fluorocyclohexyloxy, 2-chlorocyclohexyloxy, 3-chlorocyclohexyloxy, 4-chlorocyclohexyloxy, 2,3-dimethylcyclohexyloxy, 2-hydroxycyclohexyloxy, 3-hydroxycyclohexyloxy, 2-methoxycyclohexyloxy, 3-methoxycyclohexyloxy, 2-ethylcyclohexyloxy, cycloheptyloxy, cyclooctyloxy, 4-hydroxycyclohexyloxy, 2,2-dimethylcyclopropoxy, and 4-methoxycyclohexyloxy.

The $C_7$-$C_9$ aralkyl, which is represented by $R^5$, may include benzyl, 1-phenylethyl, and 2-phenylethyl, wherein the aralkyl group may be optionally substituted on the aryl or alkyl moiety, or on both moieties.

For the substituents on the phenyl or $C_7$-$C_9$ aralkyl group, which is represented by $R^5$, the $C_1$-$C_4$ alkyl may include methyl, ethyl, propyl, 1-methylethyl, and butyl; the $C_1$-$C_4$ haloalkyl may include trifluoromethyl, perfluoroethyl, and 2,2,2-trifluoroethyl; the $C_1$-$C_4$ alkoxy may include methoxy, ethoxy, propoxy, and 1-methylethoxy; the $C_1$-$C_4$ haloalkoxy may include trifluoromethoxy, perfluoroethoxy, and 2,2,2-trifluoroethoxy; the $C_1$-$C_3$ alkylthio may include methylthio and ethylthio; the $C_1$-$C_4$ haloalkylthio may include trifluoromethylthio; the $C_3$-$C_7$ alkynyloxy may include propynyloxy; the $C_2$-$C_6$ (alkoxyalkoxy) may include methoxymethoxy and ethoxymethoxy; the $C_2$-$C_6$ (alkylcarbonyl) may include acetyl and propionyl; the $C_2$-$C_6$ (alkylcarbonyloxy) may include acetoxy and isobutyryloxy.

Specific examples of the optionally substituted phenyl, which is represented by $R^5$, may include phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-fluoro-3-trifluoromethylphenyl, 2-fluoro-6-trifluoromethylphenyl, 2,3-difluoro-6-trifluoromethylphenyl, 2,3,6-trifluorophenyl, 2,4,6-trifluorophenyl, 2-chloro-3-fluorophenyl, 3-chloro-2-fluorophenyl, 2-chloro-4-fluorophenyl, 2-chloro-5-fluorophenyl, 2-chloro-6-fluorophenyl, 2-chloro-4,6-difluorophenyl, 2,3,4,6-tetrafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,6-dichloro-4-fluorophenyl, 2,3,6-trichlorophenyl, 2,4,6-trichlorophenyl, 2-bromophenyl, 3-bromophenyl, 4-bromophenyl, 2-trifluoromethylphenyl, 3-trifluoromethylphenyl, 4-trifluoromethylphenyl, 3,5-bistrifluoromethylphenyl, 2-perfluoroethylphenyl, 3-(2,2,2-trifluoroethyl)phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2-propylphenyl, 3-propylphenyl, 4-propylphenyl, 2-(1-methylethyl)phenyl, 3-(1-methylethyl)phenyl, 4-(1-methylethyl)phenyl, 4-(1,1-dimethylethyl)phenyl, 2-methylthiophenyl, 3-methylthiophenyl, 4-methylthiophenyl, 2-ethylthiophenyl, 2-trifluoromethylthiophenyl, 3-trifluoromethylthiophenyl, 4-trifluoromethylthiophenyl, 2-methoxyphenyl, 3-methoxyphenyl, 4-methoxyphenyl, 2-ethoxyphenyl, 2-propoxyphenyl, 2-(1-methylethoxy)phenyl, 2-trifluoromethoxyphenyl, 3-trifluoromethoxyphenyl, 4-trifluoromethoxyphenyl, 2-(2,2,2-trifluoroethoxy)phenyl, 2-cyanophenyl, 2-nitrophenyl, 3-nitrophenyl, 4-nitrophenyl, 2-phenylphenyl, 2-phenoxyphenyl, 3-phenoxyphenyl, and 4-phenoxyphenyl.

Specific examples of the optionally substituted $C_7$-$C_9$ aralkyl, which is represented by $R^5$, may include benzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-fluoro-3-trifluoromethylbenzyl, 2-fluoro-6-trifluoromethylbenzyl, 2,3-difluoro-6-trifluoromethylbenzyl, 2,3,6-trifluorobenzyl, 2,4,6-trifluorobenzyl, 2-chloro-3-fluorobenzyl, 3-chloro-2-fluorobenzyl, 2-chloro-4-fluorobenzyl, 2-chloro-5-fluorobenzyl, 2-chloro-6-fluorobenzyl, 2-chloro-4,6-difluorobenzyl, 2,3,4,6-tetrafluorobenzyl, 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 2,6-dichloro-4-fluorobenzyl, 2,3,6-trichlorobenzyl, 2,4,6-trichlorobenzyl, 2-bromobenzyl, 3-bromobenzyl, 4-bromobenzyl, 2-trifluoromethylbenzyl, 3-trifluoromethylbenzyl, 4-trifluoromethylbenzyl, 3,5-bistrifluoromethylbenzyl, 2-perfluoroethylbenzyl, 3-(2,2,2-trifluoroethyl)benzyl, 2-methylbenzyl, 3-methylbenzyl, 4-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2-ethylbenzyl, 3-ethylbenzyl, 4-ethylbenzyl, 2-propylbenzyl, 3-propylbenzyl, 4-propylbenzyl, 2-(1-methylethyl)benzyl, 3-(1-methylethyl)benzyl, 4-(1-methylethyl)benzyl, 4-(1,1-dimethylethyl)benzyl, 2-methylthiobenzyl, 3-methylthiobenzyl, 4-methylthiobenzyl, 2-ethylthiobenzyl, 2-trifluoromethylthiobenzyl, 3-trifluoromethylthiobenzyl, 4-trifluoromethylthiobenzyl, 2-methoxybenzyl, 3-methoxybenzyl, 4-methoxybenzyl, 2-ethoxybenzyl, 2-propoxybenzyl, 2-(1-methylethoxy)benzyl, 2-trifluoromethoxybenzyl, 3-trifluoromethoxybenzyl, 4-trifluoromethoxybenzyl, 2-(2,2,2-trifluoroethoxy)benzyl, 2-cyanobenzyl, 2-nitrobenzyl, 3-nitrobenzyl, 4-nitrobenzyl, 2-phenylbenzyl, 2-phenoxybenzyl, 3-phenoxybenzyl, 4-phenoxybenzyl, 2-phenylethyl, 2-(2-fluorophenyl)ethyl, 2-(3-fluorophenyl)ethyl, 2-(4-fluorophenyl)ethyl, 2-(2,3-difluorophenyl)ethyl, 2-(2,4-difluorophenyl)ethyl, 2-(2,5-difluorophenyl)ethyl, 2-(2,6-difluorophenyl)ethyl, 2-(3,4-difluorophenyl)ethyl, 2-(3,5-difluorophenyl)ethyl, 2-(2-fluoro-3-trifluoromethylphenyl)ethyl, 2-(2-fluoro-6-trifluoromethylphenyl)ethyl, 2-(2,3-difluoro-6-fluoromethylphenyl)ethyl, 2-(2,3,6-trifluorophenyl)ethyl, 2-(2,4,6-trifluorophenyl)ethyl, 2-(2-chloro-3-fluorophenyl)ethyl, 2-(3-chloro-2-fluorophenyl)ethyl, 2-(2-chloro-4-fluorophenyl)ethyl, 2-(2-chloro-5-fluorophenyl)ethyl, 2-(2-chloro-6-fluorophenyl)ethyl, 2-(2-chloro-4,6-difluorophenyl)ethyl, 2-(2,3,4,6-tetrafluorophenyl)ethyl, 2-(2-chlorophenyl)ethyl, 2-(3-chlorophenyl)ethyl, 2-(4-chlorophenyl)ethyl, 2-(2,3-dichlorophenyl)ethyl, 2-(2,4-dichlorophenyl)ethyl, 2-(2,5-dichlorophenyl)ethyl, 2-(2,6-dichlorophenyl)ethyl, 2-(3,4-dichlorophenyl)ethyl, 2-(3,5-dichlorophenyl)ethyl, 2-(2,6-dichloro-4-fluorophenyl)ethyl, 2-(2,3,6-trichlorophenyl)ethyl, 2-(2,4,6-trichlorophenyl)ethyl, 2-(2-bromophenyl)ethyl, 2-(3-bromophenyl)ethyl, 2-(4-bromophenyl)ethyl, 2-(2-trifluoromethylphenyl)ethyl, 2-(3-trifluoromethylphenyl)ethyl, 2-(4-trifluoromethylphenyl)ethyl, 2-(3,5-bistrifluoromethylphenyl)ethyl, 2-(2-perfluoroethylphenyl)ethyl, 2-(3-(2,2,2-trifluoroethyl)phenyl)ethyl, 2-methylphenyl)ethyl, 2-(3-methylphenyl)ethyl, 2-(4-methylphenyl)ethyl, 2-(2,3-dimethylphenyl)ethyl, 2-(2,4-dimethylphenyl)ethyl, 2-(2,5-dimethylphenyl)ethyl, 2-(2,6-dimethylphenyl)ethyl, 2-(3,4-dimethylphenyl)ethyl, 2-(3,5-dimethylphenyl)ethyl, 2-(2-ethylphenyl)ethyl, 2-(3-ethylphenyl)ethyl, 2-(4-ethylphenyl)ethyl, 2-(2-propylphenyl)ethyl, 2-(3-propylphenyl)ethyl, 2-(4-propylphenyl)ethyl, 2-(2-(1-methylethyl)phenyl)ethyl, 2-(3-(1-methylethyl)phenyl)ethyl, 2-(4-(1-methylethyl)phenyl)ethyl, 2-(4-(1,1-dimethylethyl)phenyl)ethyl, 2-(2-methylthiophenyl)ethyl, 2-(3-methylthiophenyl)ethyl, 2-(4-methylthiophenyl)ethyl, 2-(2-ethylthiophenyl)ethyl, 2-(2-trifluoromethylthiophenyl)ethyl, 2-(3-trifluoromethylthiophenyl)ethyl, 2-(4-trifluoromethylthiophenyl)ethyl, 2-(2-methoxyphenyl)ethyl, 2-(3-methoxyphenyl)ethyl, 2-(4-methoxyphenyl)ethyl, 2-(2-ethoxyphenyl)ethyl, 2-(2-propoxyphenyl)ethyl, 2-(2-(1-methylethoxy)phenyl)ethyl, 2-(2-trifluoromethoxyphenyl)ethyl, 2-(3-trifluoromethoxyphenyl)ethyl, 2-(4-trifluoromethoxyphenyl)ethyl, 2-(2-perfluoroethoxyphenyl)ethyl, 2-(2-(2,2,2-trifluoroethoxy)phenyl)ethyl, 2-(2-cyanophenyl)ethyl, 2-(2-nitrophenyl)ethyl, 2-(3-nitrophenyl)ethyl, 2-(4-nitrophenyl)ethyl, 2-(2- phenylphenyl)ethyl, 2-(2-phenoxyphenyl)ethyl, 2-(3-phenoxyphenyl)ethyl, 2-(4-phenoxyphenyl)ethyl, 1-phenylethyl, 1-(2-fluorophenyl)ethyl, 1-(3-fluorophenyl)ethyl, 1-(4-fluorophenyl)ethyl, 1-(2,3-difluorophenyl)ethyl, 1-(2,4-difluorophenyl)ethyl, 1-(2,5-difluorophenyl)ethyl, 1-(2,6-difluorophenyl)ethyl, 1-(3,4-difluorophenyl)ethyl, 1-(3,5-difluorophenyl)ethyl, 1-(2-fluoro-3-trifluoromethylphenyl)ethyl, 1-(2-fluoro-6-trifluoromethylphenyl)ethyl, 1-(2,3-difluoro-6-fluoromethylphenyl)ethyl, 1-(2,3,6-trifluorophenyl)ethyl, 1-(2,4,6-trifluorophenyl)ethyl, 1-(2-chloro-3-fluorophenyl)ethyl, 1-(3-chloro-2-fluorophenyl)ethyl, 1-(2-chloro-4-fluorophenyl)ethyl, 1-(2-chloro-5-fluorophenyl)ethyl, 1-(2-chloro-6-fluorophenyl)ethyl, 1-(2-chloro-4,6-difluorophenyl)ethyl, 1-(2,3,4,6-tetrafluorophenyl)ethyl, 1-(2-chlorophenyl)ethyl, 1-(3-chlorophenyl)ethyl, 1-(4-chlorophenyl)ethyl, 1-(2,3-dichlorophenyl)ethyl, 1-(2,4-dichlorophenyl)ethyl, 1-(2,5-dichlorophenyl)ethyl, 1-(2,6-dichlorophenyl)ethyl, 1-(3,4-dichlorophenyl)ethyl, 1-(3,5-dichlorophenyl)ethyl, 1-(2,6-dichloro-4-fluorophenyl)ethyl, 1-(2,3,6-trichlorophenyl)ethyl, 1-(2,4,6-trichlorophenyl)ethyl, 1-(2-bromophenyl)ethyl, 1-(3-bromophenyl)ethyl, 1-(4-bromophenyl)ethyl, 1-(2-trifluoromethylphenyl)ethyl, 1-(3-trifluoromethylphenyl)ethyl, 1-(4-trifluoromethylphenyl)ethyl, 1-(3,5-bistrifluoromethylphenyl)ethyl, 1-(2-perfluoroethylphenyl)ethyl, 1-(3-(2,2,2-trifluoroethyl)phenyl)ethyl, 1-(2-methylphenyl)ethyl, 1-(3-methylphenyl)ethyl, 1-(4-methylphenyl)ethyl, 1-(2,3-dimethylphenyl)ethyl, 1-(2,4-dimethylphenyl)ethyl, 1-(2,5-dimethylphenyl)ethyl, 1-(2,6-dimethylphenyl)ethyl, 1-(3,4-dimethylphenyl)ethyl, 1-(3,5-dimethylphenyl)ethyl, 1-(2-ethylphenyl)ethyl, 1-(3-ethylphenyl)ethyl, 1-(4-ethylphenyl)ethyl, 1-(2-propylphenyl)ethyl, 1-(3-propylphenyl)ethyl, 1-(4-propylphenyl)ethyl, 1-(2-(1-methylethyl)phenyl)ethyl, 1-(3-(1-methylethyl)phenyl)ethyl, 1-(4-(1-methylethyl)phenyl)ethyl, 1-(4-(1,1-dimethylethyl)phenyl)ethyl, 1-(2-methylthiophenyl)ethyl, 1-(3-methylthiophenyl)ethyl, 1-(4-methylthiophenyl)ethyl, 1-(2-ethylthiophenyl)ethyl, 1-(2-trifluoromethylthiophenyl)ethyl, 1-(3-trifluoromethylthiophenyl)ethyl, 1-(4-trifluoromethylthiophenyl)ethyl, 1-(2-methoxyphenyl)ethyl, 1-(3-methoxyphenyl)ethyl, 1-(4-methoxyphenyl)ethyl, 1-(2-ethoxyphenyl)ethyl, 1-(2-propoxyphenyl)ethyl, 1-(2-(1-methylethoxy)phenyl)ethyl, 1-(2-trifluoromethoxyphenyl)ethyl, 1-(3-trifluoromethoxyphenyl)ethyl, 1-(4-trifluoromethoxyphenyl)ethyl, 1-(2-perfluoroethoxyphenyl)ethyl, 1-(2-(2,2,2-trifluoroethoxy)phenyl)ethyl, 1-(2-cyanophenyl)ethyl, 1-(2-nitrophenyl)ethyl, 1-(3-nitrophenyl)ethyl, 1-(4-nitrophenyl)ethyl, 1-(2-phenylphenyl)ethyl, 1-(2-phenoxyphenyl)ethyl, 1-(3-phenoxyphenyl)ethyl, and 1-(4-phenoxyphenyl)ethyl.

The $C_1$-$C_7$ alkyl, which is represented by $R^6$ or $R^7$, may include methyl, ethyl, propyl, 1-methylethyl, butyl, 2-methylpropyl, 1-methylpropyl, 1,1-dimethylethyl, pentyl, 3-methylbutyl, 2,2-dimethylpropyl, 1,1-dimethylpropyl, 1-ethylpropyl, hexyl, 5-methylpentyl, 2-ethylbutyl, 3-methylpentyl, 1,3-dimethylbutyl, heptyl, and 1-ethyl-1-methylbutyl.

The $C_1$-$C_3$ haloalkyl, represented by $R^6$ or $R^7$, may include difluoromethyl, dibromofluoromethyl, 1-chloroethyl, 1-bromoethyl, 2,2,2-trifluoroethyl, 2-fluoroethyl, 2-chloroethyl, 2,2-difluoroethyl, 3-fluoropropyl, 3,3,3-trifluoropropyl, 2-fluoropropyl, and 2-bromopropyl.

The $C_2$-$C_4$ (alkoxymethyl), which is represented by $R^6$ or $R^7$, may include methoxymethyl, ethoxymethyl, propoxymethyl, and 1-methylethoxymethyl.

The $C_2$-$C_4$ (haloalkoxymethyl), which is represented by $R^6$ or $R^7$, may include chloromethoxymethyl, bromomethoxymethyl, 2-chloroethoxymethyl, 2-bromoethoxymethyl, and 2,2,2-trifluoroethoxymethyl.

The $C_3$-$C_6$ alkenyl, which is represented by $R^6$ or $R^7$, may include 2-propenyl, 2-butenyl, 3-butenyl, 1-methyl-2-propenyl, 2-methyl-2-propenyl, 2-pentenyl, 1-methyl-2-butenyl, 3-methyl-3-butenyl, 1-ethyl-2-propenyl, 2-hexenyl, 2-methyl-2-pentenyl, 3-methyl-2-pentenyl, 4-methyl-2-pentenyl, 1-methyl-3-pentenyl, 4-methyl-3-pentenyl, 1-methyl-4-pentenyl, 3-methyl-4-pentenyl, and 4-methyl-4-pentenyl.

The $C_3$-$C_6$ haloalkenyl, which is represented by $R^6$ or $R^7$, may include 3-chloro-2-propenyl, 2-chloro-2-propeyl, 2-bromo-2-propenyl, 3,3-dichloro-2-propenyl, 3,3-difluoro-2-propenyl, 2,3-dichloro-2-propenyl, 2,3-dibromo-2-propenyl, 3-chloro-4,4,4-trifluoro-2-butenyl, 3,4-dichloro-4,4-difluoro-2-butenyl, 3,4,4,4-tetrafluoro-2-butenyl, 4,4-dibromo-2-butenyl, 6,6-dichloro-5-hexenyl, and 6,6-dibromo-5-hexenyl.

The $C_3$-$C_7$ alkynyl, which is represented by $R^6$ or $R^7$, may include 2-propynyl, 2-butynyl, 2-pentynyl, 4,4-dimethyl-2-pentynyl, 1-methyl-2-propynyl, and 1,1-dimethyl-2-propynyl.

The substituents in the optionally substituted phenyl and in the optionally substituted $C_7$-$C_9$ aralkyl, which are represented by $R^6$ or $R^7$, may include the above substituents for $R^5$, and specific examples thereof may include the above groups for $R^5$.

The embodiments of the present compounds may include the following compounds.

The pyrimidine compounds of formula (1) wherein $R^1$ is 2-propynyl optionally substituted with halogen, 2-butynyl optionally substituted with halogen, or 2-methyl-2-butynyl optionally substituted with halogen;

The pyrimidine compounds of formula (1) wherein $R^2$ and $R^3$ are both hydrogen;

The pyrimidine compounds of formula (1) wherein $R^2$ is hydrogen and $R^3$ is chlorine or fluorine;

The pyrimidine compounds of formula (1) wherein $R^1$ is $C_3$-$C_7$ alkyl optionally substituted with halogen; $R^2$ and $R^3$ are both hydrogen; and $R^4$ is 2-halophenyl; the pyrimidine compounds of formula (1) wherein $R^1$ is $C_3$-$C_7$ alkyl optionally substituted with halogen; $R^2$ and $R^3$ are both hydrogen; and $R^4$ is 3-halophenyl; the pyrimidine compounds of formula (1) wherein $R^1$ is $C_3$-$C_7$ alkyl optionally substituted with halogen; $R^2$ and $R^3$ are both hydrogen; and $R^4$ is 2,3-dihalophenyl; the pyrimidine compounds of formula (1) wherein $R^1$ is $C_3$-$C_7$ alkyl optionally substituted with halogen; $R^2$ and $R^3$ are both hydrogen; and $R^4$ is 2,6-dihalophenyl;

The pyrimidine compounds of formula (1) wherein $R^1$ is $C_3$-$C_7$ alkyl optionally substituted with halogen; $R^2$ and $R^3$ are both hydrogen; and $R^4$ is 2-halophenoxy; the pyrimidine compounds of formula (1) wherein $R^1$ is $C_3$-$C_7$ alkyl optionally substituted with halogen; $R^2$ and $R^3$ are both hydrogen; and $R^4$ is 3-halophenoxy; the pyrimidine compounds of formula (1) wherein $R^1$ is $C_3$-$C_7$ alkyl optionally substituted with halogen; $R^2$ and $R^3$ are both hydrogen; and $R^4$ is 2,3-dihalophenoxy; the pyrimidine compounds of formula (1) wherein $R^1$ is $C_3$-$C_7$ alkyl optionally substituted with halogen; $R^2$ and $R^3$ are both hydrogen; and $R^4$ is 2,6-dihalophenoxy;

The pyrimidine compounds of formula (1) wherein $R^1$ is $C_3$-$C_7$ alkyl optionally substituted with halogen; $R^2$ and $R^3$ are both hydrogen; and $R^4$ is 2-halobenzyl; the pyrimidine compounds of formula (1) wherein $R^1$ is $C_3$-$C_7$ alkyl optionally substituted with halogen; $R^2$ and $R^3$ are both hydrogen; and $R^4$ is 3-halobenzyl; the pyrimidine compounds of formula (1) wherein $R^1$ is $C_3$-$C_7$ alkyl optionally substituted with halogen; $R^2$ and $R^3$ are both hydrogen; and $R^4$ is 2,3-dihalobenzyl; the pyrimidine compounds of formula (1) wherein $R^1$ is $C_3$-$C_7$ alkyl optionally substituted with halogen; $R^2$ and $R^3$ are both hydrogen; and $R^4$ is 2,6-dihalophenyl; the pyrimidine compounds of formula (1) wherein $R^1$ is $C_3$-$C_7$ alkyl optionally substituted with halogen; $R^2$ and $R^3$ are both hydrogen; $R^4$ is a group of formula —N($C_2H_5$)$R^7$; and $R^7$ is $C_3$-$C_5$ 2-alkynyl optionally substituted with halogen; the pyrimidine compounds of formula (1) wherein $R^1$ is $C_3$-$C_7$ alkyl optionally substituted with halogen; $R^2$ and $R^3$ are both hydrogen; and $R^4$ is a group of formula —N($C_2H_5$) $R^7$; and $R^7$ is $C_3$-$C_5$ alkenyl optionally substituted with halogen; and the pyrimidine compounds of formula (1) wherein $R^1$ is $C_3$-$C_7$ alkyl optionally substituted with halogen; $R^2$ and $R^3$ are both hydrogen; and $R^4$ is a group of formula —N($C_2H_5$)—$R^7$; and $R^7$ is $C_2$-$C_3$ alkyl.

Specific examples of the present compounds are show below.

The compounds of formula (25):

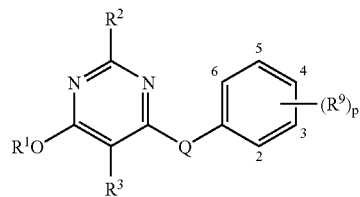

(25)

wherein Q is oxygen, $R^1$ is 2-propynyl, $R^2$ and $R^3$ are both hydrogen, and the substituent(s) $(R^9)_p$ on the benzene ring are selected from those of Table 1.

TABLE 1

| H | 2-$CH_3$ | 3-$SCF_3$ | 2-Cl-3-F |
|---|---|---|---|
| 2-Cl | 3-$CH_3$ | 4-$SCF_3$ | 2-Cl-6-F |
| 3-Cl | 4-$CH_3$ | 2,3-diF | 2-Cl-4,6-diF |
| 4-Cl | 2-$CF_3$ | 2,4-diF | 2,3-diCl |
| 2-F | 3-$CF_3$ | 2,5-diF | 2,3-di$CH_3$ |
| 3-F | 4-$CF_3$ | 2,6-diF | 2,3,6-triF |
| 4-F | 2-$OCF_3$ | 3,4-diF | 2,4,6-triF |
| 2-$OCH_3$ | 3-$OCF_3$ | 3,5-diF | 2,3,4,6-tetraF |
| 3-$OCH_3$ | 4-$OCF_4$ | 2-F-3-$CF_3$ | |
| 4-$OCH_4$ | 2-$SCF_3$ | 2-F-6-$CF_3$ | |

The compounds of formula (25) wherein Q is oxygen, $R^1$ is 2-propynyl, $R^2$ is methyl, $R^3$ is hydrogen, and the substituent(s) $(R^9)_p$ on the benzene ring are selected from those of Table 2.

TABLE 2

| H | 3-Cl | 2,3-di$CH_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 2-propynyl, $R^2$ and $R^3$ are both methyl, and the substituent(s) $(R^9)_p$ on the benzene ring are those of Table 3.

TABLE 3

| H | 3-Cl | 2,3-di$CH_3$ | 2,6-diF |
|---|---|---|---|
| 2-Cl | 3-Br | 2-Cl-6-F | 2,3-diF |

TABLE 3-continued

| 2-Br | 3-F | 2-Cl-3-F | 2-Cl-3,6-diF |
|---|---|---|---|
| 2-F | 2,3-diCl | 3-Cl-2-F | |

The compounds of formula (25) wherein Q is oxygen, $R^1$ is 2-propynyl, $R^2$ is hydrogen, $R^3$ is methyl, and the substituent(s) $(R^9)_p$ on the benzene ring are those of Table 4.

TABLE 4

| H | 3-Cl | 2,3-di$CH_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 2-butynyl, $R^2$ and $R^3$ are both hydrogen, and the substituent(s) $(R^9)_p$ on the benzene ring are those of Table 5.

TABLE 5

| H | 3-CN | 2-OPh | 2,6-di$CH_3$ |
|---|---|---|---|
| 2-Cl | 4-CN | 3-OPh | 2-F-3-$CF_3$ |
| 3-Cl | 2-$SCH_3$ | 4-OPh | 2-F-6-$CF_3$ |
| 4-Cl | 3-$SCH_3$ | 2-ethoxy | 2-Cl-3-F |
| 2-F | 4-$SCH_3$ | 3-ethoxy | 2-Cl-4-F |
| 3-F | 2-$OCF_3$ | 4-ethoxy | 2-Cl-5-F |
| 4-F | 3-$OCF_3$ | 2-isopropyl | 2-Cl-6-F |
| 2-Br | 4-$OCF_3$ | 3-isopropyl | 3-Cl-2-F |
| 3-Br | 2-$SCF_3$ | 4-isopropyl | 2-Cl-4,6-diF |
| 4-Br | 3-$SCF_3$ | 2,3-diF | 2,3-diCl |
| 2-I | 4-$SCF_3$ | 2,4-diF | 2,4-diCl |
| 3-I | 2-$CH_2CH_3$ | 2,5-diF | 2,5-diCl |
| 4-I | 3-$CH_2CH_3$ | 2,6-diF | 2,6-diCl |
| 2-$OCH_3$ | 4-$CH_2CH_3$ | 3,4-diF | 3,4-diCl |
| 3-$OCH_3$ | 2-propyl | 3,5-diF | 3,5-diCl |
| 4-$OCH_3$ | 3-propyl | 3,5-di$CF_3$ | 2,3,6-triCl |
| 2-$CH_3$ | 4-propyl | 2,3,6-triF | 2,4,6-triCl |
| 3-$CH_3$ | 2-$NO_2$ | 2,4,6-triF | 2,6-diCl-4-F |
| 4-$CH_3$ | 3-$NO_2$ | 3,4-di$CH_3$ | 2,3-diF-6-$CF_3$ |
| 2-$CF_3$ | 4-$NO_2$ | 3,5-di$CH_3$ | 2,3,4,6-tetraF |
| 3-$CF_3$ | 2-Ph | 2,3-di$CH_3$ | |
| 4-$CF_3$ | 3-Ph | 2,4-di$CH_3$ | |
| 2-CN | 4-Ph | 2,5-di$CH_3$ | |

The compounds of formula (25) wherein Q is oxygen, $R^1$ is 2-butynyl, $R^2$ is methyl, $R^3$ is hydrogen, and the substituent(s) $(R^9)_p$ on the benzene ring are those of Table 6.

TABLE 6

| H | 3-Cl | 2,3-di$CH_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 2-butynyl, $R^2$ and $R^3$ are both methyl, and the substituent(s) $(R^9)_p$ on the benzene ring are those of Table 7.

TABLE 7

| H | 3-Cl | 2,3-di$CH_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 2-butynyl, $R^2$ is hydrogen, $R^3$ is methyl, and the substituent(s) $(R^9)_p$ on the benzene ring are those of Table 8.

TABLE 8

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 1-methyl-2-butynyl, $R^2$ and $R^3$ are both hydrogen, and the substituent(s) $(R^9)_p$ on the benzene ring are those of Table 9.

TABLE 9

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 1-methyl-2-propynyl, $R^2$ are $R^3$ are both hydrogen, and the substituent(s) $(R^9)_p$ on the benzene ring are those of Table 10.

TABLE 10

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is oxygen, $R^1$ is 3-pentynyl, $R^2$ and $R^3$ are both hydrogen, and the substituent(s) $(R^9)_p$ on the benzene ring are those of Table 11.

TABLE 11

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds formula (25) wherein Q is oxygen, $R^1$ is 2-butynyl, $R^2$ is hydrogen, $R^3$ is fluorine, and the substituent(s) $(R^9)_p$ on the benzene ring are those of Table 12.

TABLE 12

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CH$_2$, $R^1$ is 2-propynyl, $R^2$ and $R^3$ are both hydrogen, and the substituent(s) $(R^9)_p$ on the benzene ring are those of Table 13.

TABLE 13

| H | 3-CH$_3$ | 2-CH$_3$ | 2-Cl-3-F |
|---|---|---|---|
| 2-Cl | 4-CH$_3$ | 2-CN | 2-Cl-6-F |
| 3-Cl | 2-CF$_3$ | 4-SCF$_3$ | 2-Cl-4,6-diF |
| 4-Cl | 3-CF$_3$ | 2,3-diF | 2,3-diCl |
| 2-F | 4-CF$_3$ | 2,4-diF | 2,3-diCH$_3$ |
| 3-F | 2-OCF$_3$ | 2,5-diF | 2,3,6-triF |
| 4-F | 3-OCF$_3$ | 2,6-diF | 2,4,6-triF |
| 2-OCH$_3$ | 4-OCF$_3$ | 3,4-diF | 2,3,4,6-tetraF |
| 3-OCH$_3$ | 2-SCF$_3$ | 3,5-diF | 3-CN |
| 4-OCH$_3$ | 3-SCF$_3$ | 2-F-3-CF$_3$ | 4-CN |

The compounds of formula (25) wherein Q is CH$_2$, $R^1$ is 2-propynyl, $R^2$ is methyl, $R^3$ is hydrogen, and the substituent(s) $(R^9)_p$ on the benzene ring are those of Table 14.

TABLE 14

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CH$_2$, $R^1$ is 2-propynyl, $R^2$ and $R^3$ are both methyl, and the substituent(s) $(R^9)_p$ on the benzene ring are those of Table 15.

TABLE 15

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CH$_2$, $R^1$ is 2-propynyl, $R^2$ is hydrogen, $R^3$ is methyl, and the substituent(s) $(R^9)_p$ on the benzene ring are those of Table 16.

TABLE 16

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CH$_2$, $R^1$ is 2-butynyl, $R^2$ and $R^3$ are both hydrogen, and the substituent(s) $(R^9)_p$ on the benzene ring are those of Table 17.

TABLE 17

| H | 3-CN | 2-OPh | 2,6-diCH$_3$ |
|---|---|---|---|
| 2-Cl | 4-CN | 3-OPh | 2-F-3-CF$_3$ |
| 3-Cl | 2-SCH$_3$ | 4-OPh | 2-F-6-CF$_3$ |
| 4-Cl | 3-SCH$_3$ | 2-ethoxy | 2-Cl-3-F |
| 2-F | 4-SCH$_3$ | 3-ethoxy | 2-Cl-4-F |
| 3-F | 2-OCF$_3$ | 4-ethoxy | 2-Cl-5-F |
| 4-F | 3-OCF$_3$ | 2-isopropyl | 2-Cl-6-F |
| 2-Br | 4-OCF$_3$ | 3-isopropyl | 3-Cl-2-F |
| 3-Br | 2-SCF$_3$ | 4-isopropyl | 2-Cl-4,6-diF |
| 4-Br | 3-SCF$_3$ | 2,3-diF | 2,3-diCl |
| 2-I | 4-SCF$_3$ | 2,4-diF | 2,4-diCl |
| 3-I | 2-CH$_2$CH$_3$ | 2,5-diF | 2,5-diCl |
| 4-I | 3-CH$_2$CH$_3$ | 2,6-diF | 2,6-diCl |
| 2-OCH$_3$ | 4-CH$_2$CH$_3$ | 3,4-diF | 3,4-diCl |
| 3-OCH$_3$ | 2-propyl | 3,5-diF | 3,5-diCl |
| 4-OCH$_3$ | 3-propyl | 3,5-diCF$_3$ | 2,3,6-triCl |
| 2-CH$_3$ | 4-propyl | 2,3,6-triF | 2,4,6-triCl |
| 3-CH$_3$ | 2-NO$_2$ | 2,4,6-triF | 2,6-diCl-4-F |
| 4-CH$_3$ | 3-NO$_2$ | 3,4-diCH$_3$ | 2,3-diF-6-CF$_3$ |
| 2-CF$_3$ | 4-NO$_2$ | 3,5-diCH$_3$ | 2,3,4,6-tetraF |
| 3-CF$_3$ | 2-Ph | 2,3-diCH$_3$ | |
| 4-CF$_3$ | 3-Ph | 2,4-diCH$_3$ | |
| 2-CN | 4-Ph | 2,5-diCH$_3$ | |

The compounds of formula (25) wherein Q is CH$_2$, $R^1$ is 2-butynyl, $R^2$ is methyl, $R^3$ is hydrogen, and the substituent(s) $(R^9)_p$ on the benzene ring are those of Table 18.

TABLE 18

| H | 3-Cl | 2,3-diCH$_3$ | 2,6-diF |
|---|---|---|---|
| 2-Cl | 3-Br | 2-Cl-6-F | 2,3-diF |

TABLE 18-continued

| | | | |
|---|---|---|---|
| 2-Br | 3-F | 2-Cl-3-F | 2-Cl-3,6-diF |
| 2-F | 2,3-diCl | 3-Cl-2-F | |

The compounds of formula (25) wherein Q is $CH_2$, $R^1$ is 2-butynyl, $R^2$ and $R^3$ are both methyl, and the substituent(s) $(R^9)_p$ on the benzene ring are those of Table 19.

TABLE 19

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CH_2$, $R^1$ is 2-butynyl, $R^2$ is hydrogen, $R^3$ is methyl, and the substituent(s) $(R^9)_p$ on the benzene ring are those of Table 20.

TABLE 20

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CH_2$, $R^1$ is 2-pentynyl, $R^2$ and $R^3$ are both hydrogen, and the substituent(s) $(R^9)_p$ on the benzene ring are those of Table 21.

TABLE 21

| H | 2-CH$_3$ | 3-SCF$_3$ | 2-Cl-3-F |
|---|---|---|---|
| 2-Cl | 3-CH$_3$ | 4-SCF$_3$ | 2-Cl-6-F |
| 3-Cl | 4-CH$_3$ | 2,3-diF | 2-Cl-4,6-diF |
| 4-Cl | 3-CF$_3$ | 2,4-diF | 2,3-diCl |
| 2-F | 3-CF$_3$ | 2,5-diP | 2,3-diCH$_3$ |
| 3-F | 4-CF$_3$ | 2,6-diF | 2,3,6-triF |
| 4-F | 2-OCF$_3$ | 3,4-diF | 2,4,6-triF |
| 2-OCH$_3$ | 3-OCF$_3$ | 3,5-diF | 2,3,4,6-tetraF |
| 3-OCH$_3$ | 4-OCF$_3$ | 2-F-3-CF$_3$ | |
| 4-OCH$_3$ | 2-SCF$_3$ | 2-F-6-CF$_3$ | |

The compounds of formula (25) wherein Q is $CH_2$, $R^1$ is 1-methyl-2-butynyl, $R^2$ and $R^3$ are both hydrogen, and the substituent(s) $(R^9)_p$ on the benzene ring are those of Table 22.

TABLE 22

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CH_2$, $R^1$ is 1-methyl-2-propynyl, $R^2$ and $R^3$ are both hydrogen, and the substituent(s) $(R^9)_p$ on the benzene ring are those of Table 23.

TABLE 23

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds formula (25) wherein Q is $CH_2$, $R^1$ is 2-butynyl, $R^2$ is hydrogen, $R^3$ is fluorine, and the substituent(s) $(R^9)_p$ on the benzene ring are those of Table 24.

TABLE 24

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CHCH_3$, $R^1$ is 2-propynyl, $R^2$ and $R^3$ are both hydrogen, and the substituent(s) $(R^9)_p$ on the benzene ring are those of Table 25.

TABLE 25

| H | 2-CH$_3$ | 3-SCF$_3$ | 2-Cl-3-F |
|---|---|---|---|
| 2-Cl | 3-CH$_3$ | 4-SCF$_3$ | 2-Cl-6-F |
| 3-Cl | 4-CH$_3$ | 2,3-diF | 2-Cl-4,6-diF |
| 4-Cl | 3-CF$_3$ | 2,4-diF | 2,3-diCl |
| 2-F | 3-CF$_3$ | 2,5-diF | 2,3-diCH$_3$ |
| 3-F | 4-CF$_3$ | 2,6-diF | 2,3,6-triF |
| 4-F | 2-OCF$_3$ | 3,4-diF | 2,4,6-triF |
| 2-OCH$_3$ | 3-OCF$_3$ | 3,5-diF | 2,3,4,6-tetraF |
| 3-OCH$_3$ | 4-OCF$_3$ | 2-F-3-CF$_3$ | |
| 4-OCH$_3$ | 2-SCF$_3$ | 2-F-6-CF$_3$ | |

The compounds of formula (25) wherein Q is $CHCH_3$, $R^1$ is 2-propynyl, $R^2$ is methyl, $R^3$ is hydrogen, and the substituent(s) $(R^9)_p$ on the benzene ring are those of Table 26.

TABLE 26

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CHCH_3$, $R^1$ is 2-propynyl, $R^2$ and $R^3$ are both methyl, and the substituent(s) $(R^9)_p$ on the benzene ring are those of Table 27.

TABLE 27

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CHCH_3$, $R^1$ is 2-propynyl, $R^2$ is hydrogen, $R^3$ is methyl, and the substituent(s) $(R^9)_p$ on the benzene ring are those of Table 28.

TABLE 28

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is $CHCH_3$, $R^1$ is 2-butynyl, $R^2$ and $R^3$ are both hydrogen, and the substituent(s) $(R^9)_p$ on the benzene ring are those of Table 29.

TABLE 29

| H | 3-CN | 2-OPh | 2,6-diCH$_3$ |
|---|---|---|---|
| 2-Cl | 4-CN | 3-OPh | 2-F-3-CF$_3$ |
| 3-Cl | 2-SCH$_3$ | 4-OPh | 2-F-6-CF$_3$ |
| 4-Cl | 3-SCH$_3$ | 2-ethoxy | 2-Cl-3-F |
| 2-F | 4-SCH$_3$ | 3-ethoxy | 2-Cl-4-F |
| 3-F | 2-OCF$_3$ | 4-ethoxy | 2-Cl-5-F |

TABLE 29-continued

| | | | |
|---|---|---|---|
| 4-F | 3-OCF$_3$ | 2-isopropyl | 2-Cl-6-F |
| 2-Br | 4-OCF$_3$ | 3-isopropyl | 3-Cl-2-F |
| 3-Br | 2-SCF$_3$ | 4-isopropyl | 2-Cl-4,6-diF |
| 4-Br | 3-SCF$_3$ | 2,3-diF | 2,3-diCl |
| 2-I | 4-SCF$_3$ | 2,4-diF | 2,4-diCl |
| 3-I | 2-CH$_2$CH$_3$ | 2,5-diF | 2,5-diCl |
| 4-I | 3-CH$_2$CH$_3$ | 2,6-diF | 2,6-diCl |
| 2-OCH$_3$ | 4-CH$_2$CH$_3$ | 3,4-diF | 3,4-diCl |
| 3-OCH$_3$ | 2-propyl | 3,5-diF | 3,5-diCl |
| 4-OCH$_3$ | 3-propyl | 3,5-diCF$_3$ | 2,3,6-triCl |
| 2-CH$_3$ | 4-propyl | 2,3,6-triF | 2,4,6-triCl |
| 3-CH$_3$ | 2-NO$_2$ | 2,4,6-triF | 2,6-diCl-4-F |
| 4-CH$_3$ | 3-NO$_2$ | 3,4-diCH$_3$ | 2,3-diF-6-CF$_3$ |
| 2-CF$_3$ | 4-NO$_2$ | 3,5-diCH$_3$ | 2,3,4,6-tetraF |
| 3-CF$_3$ | 2-Ph | 2,3-diCH$_3$ | |
| 4-CF$_3$ | 3-Ph | 2,4-diCH$_3$ | |
| 2-CN | 4-Ph | 2,5-diCH$_3$ | |

The compounds of formula (25) wherein Q is CHCH$_3$, R$^1$ is 2-butynyl, R$^2$ is methyl, R$^3$ is hydrogen, and the substituent(s) (R$^9$)$_p$ on the benzene ring are those of Table 30.

TABLE 30

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 2-butynyl, R$^2$ and R$^3$ are both methyl, and the substituent(s) (R$^9$)$_p$ on the benzene ring are those of Table 31.

TABLE 31

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 2-butynyl, R$^2$ is hydrogen, R$^3$ is methyl, and the substituent(s) (R$^9$)$_p$ on the benzene ring are those of Table 32.

TABLE 32

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 2-pentynyl, R$^2$ and R$^3$ are both hydrogen, and the substituent(s) (R$^9$)$_p$ on the benzene ring are those of Table 33.

TABLE 33

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 1-methyl-2-butynyl, R$^2$ and R$^3$ are both hydrogen, and the substituent(s) (R$^9$)$_p$ on the benzene ring are those of Table 34.

TABLE 34

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 1-methyl-2-propynyl, R$^2$ and R$^3$ are both hydrogen, and the substituent(s) (R$^9$)$_p$ on the benzene ring are those of Table 35.

TABLE 35

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCH$_3$, R$^1$ is 2-butynyl, R$^2$ is hydrogen, R$^3$ is fluorine, and the substituent(s) (R$^9$)$_p$ on the benzene ring are those of Table 36.

TABLE 36

| | | | |
|---|---|---|---|
| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is NH, R$^1$ is 2-propynyl, R$^2$ and R$^3$ are both hydrogen, and the substituent(s) (R$^9$)$_p$ on the benzene ring are those of Table 37.

TABLE 37

| | | | |
|---|---|---|---|
| H | 2-CH$_3$ | 3-SCF$_3$ | 2-Cl-3-F |
| 2-Cl | 3-CH$_3$ | 4-SCF$_3$ | 2-Cl-6-F |
| 3-Cl | 4-CH$_3$ | 2,3-diF | 2-Cl-4,6-diF |
| 4-Cl | 2-CF$_3$ | 2,4-diF | 2,3-diCl |
| 2-F | 3-CF$_3$ | 2,5-diF | 2,3-diCH$_3$ |
| 3-F | 4-CF$_3$ | 2,6-diF | 2,3,6-triF |
| 4-F | 2-OCF$_3$ | 3,4-diF | 2,4,6-triF |
| 2-OCH$_3$ | 3-OCF$_3$ | 3,5-diF | 2,3,4,6-tetraF |
| 3-OCH$_3$ | 4-OCF$_3$ | 2-F-3-CF$_3$ | |
| 4-OCH$_3$ | 2-SCF$_3$ | 2-F-6-CF$_3$ | |

The compounds of formula (25) wherein Q is NH, R$^1$ is 2-butynyl, R$^2$ and R$^3$ are both hydrogen, and the substituent(s) (R$^9$)$_p$ on the benzene ring are those of Table 38.

TABLE 38

| | | | |
|---|---|---|---|
| H | 2-CH$_3$ | 3-SCF$_3$ | 2-Cl-3-F |
| 2-Cl | 3-CH$_3$ | 4-SCF$_3$ | 2-Cl-6-F |
| 3-Cl | 4-CH$_3$ | 2,3-diF | 2-Cl-4,6-diF |
| 4-Cl | 2-CF$_3$ | 2,4-diF | 2,3-diCl |
| 2-F | 3-CF$_3$ | 2,5-diF | 2,3-diCH$_3$ |
| 3-F | 4-CF$_3$ | 2,6-diF | 2,3,6-triF |
| 4-F | 2-OCF$_3$ | 3,4-diF | 2,4,6-triF |
| 2-OCH$_3$ | 3-OCF$_3$ | 3,5-diF | 2,3,4,6-tetraF |
| 3-OCH$_3$ | 4-OCF$_3$ | 2-F-3-CF$_3$ | |
| 4-OCH$_3$ | 2-SCF$_3$ | 2-F-6-CF$_3$ | |

The compounds of formula (25) wherein Q is NH, R$^1$ is 2-pentynyl, R$^2$ and R$^3$ are both hydrogen, and the substituent(s) (R$^9$)$_p$ on the benzene ring are those of Table 39.

TABLE 39

| H    | 3-Cl    | 2,3-diCH$_3$ | 2,6-diF      |
|------|---------|--------------|--------------|
| 2-Cl | 3-Br    | 2-Cl-6-F     | 2,3-diF      |
| 2-Br | 3-F     | 2-Cl-3-F     | 2-Cl-3,6-diF |
| 2-F  | 2,3-diCl| 3-Cl-2-F     |              |

The compounds of formula (25) wherein Q is NCH$_3$, R$^1$ is 2-propynyl, R$^2$ and R$^3$ are both hydrogen, and the substituent(s) (R$^9$)$_p$ on the benzene ring are those of Table 40.

TABLE 40

| H      | 2-CH$_3$  | 3-SCF$_3$ | 2-Cl-3-F       |
|--------|-----------|-----------|----------------|
| 2-Cl   | 3-CH$_3$  | 4-SCF$_3$ | 2-Cl-6-F       |
| 3-Cl   | 4-CH$_3$  | 2,3-diF   | 2-Cl-4,6-diF   |
| 4-Cl   | 2-CF$_3$  | 2,4-diF   | 2,3-diCl       |
| 2-F    | 3-CF$_3$  | 2,5-diF   | 2,3-diCH$_3$   |
| 3-F    | 4-CF$_3$  | 2,6-diF   | 2,3,6-triF     |
| 4-F    | 2-OCF$_3$ | 3,4-diF   | 2,4,6-triF     |
| 2-OCH$_3$ | 3-OCF$_3$ | 3,5-diF | 2,3,4,6-tetraF |
| 3-OCH$_3$ | 4-OCF$_3$ | 2-F-3-CF$_3$ |           |
| 4-OCH$_3$ | 2-SCF$_3$ | 2-F-6-CF$_3$ |           |

The compounds of formula (25) wherein Q is NCH$_3$, R$^1$ is 2-propynyl, R$^2$ is methyl, R$^3$ is hydrogen, and the substituent(s) (R$^9$)$_p$ on the benzene ring are those of Table 41.

TABLE 41

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-propynyl, R$^2$ and R$^3$ are both methyl, and the substituent(s) (R$^9$)$_p$ on the benzene ring are those of Table 42.

TABLE 42

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-propynyl, R$^2$ is hydrogen, and R$^3$ is methyl, and the substituent(s) (R$^9$)$_p$ on the benzene ring are those of Table 43.

TABLE 43

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-butynyl, R$^2$ and R$^3$ are both hydrogen, and the substituent(s) (R$_9$)$_p$ on the benzene ring are those of Table 44.

TABLE 44

| H         | 2-CH$_3$  | 3-SCF$_3$    | 2-Cl-3-F       |
|-----------|-----------|--------------|----------------|
| 2-Cl      | 3-CH$_3$  | 4-SCF$_3$    | 2-Cl-6-F       |
| 3-Cl      | 4-CH$_3$  | 2,3-diF      | 2-Cl-4,6-diF   |
| 4-Cl      | 2-CF$_3$  | 2,4-diF      | 2,3-diCl       |
| 2-F       | 3-CF$_3$  | 2,5-diF      | 2,3-diCH$_3$   |

TABLE 44-continued

| 3-F       | 4-CF$_3$  | 2,6-diF      | 2,3,6-triF     |
|-----------|-----------|--------------|----------------|
| 4-F       | 2-OCF$_3$ | 3,4-diF      | 2,4,6-triF     |
| 2-OCH$_3$ | 3-OCF$_3$ | 3,5-diF      | 2,3,4,6-tetraF |
| 3-OCH$_3$ | 4-OCF$_3$ | 2-F-3-CF$_3$ |                |
| 4-OCH$_3$ | 2-SCF$_3$ | 2-F-6-CF$_3$ |                |

The compounds of formula (25) wherein Q is NCH$_3$, R$^1$ is 2-butynyl, R$^2$ is methyl, R$^3$ is hydrogen, and the substituent(s) (R$^9$)$_p$ on the benzene ring are those of Table 45.

TABLE 45

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-butynyl, R$^2$ and R$^3$ are both methyl, and the substituent(s) (R$_9$)$_p$ on the benzene ring are those of Table 46.

TABLE 46

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-butynyl, R$^2$ is hydrogen, R$^3$ is methyl, and the substituent(s) (R$^9$)$_p$ on the benzene ring are those of Table 47.

TABLE 47

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 2-pentynyl, R$^2$ and R$^3$ are both hydrogen, and the substituent(s) (R$^9$)$_p$ on the benzene ring are those of Table 48.

TABLE 48

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 1-methyl-2-butynyl, R$^2$ and R$^3$ are both hydrogen, and the substituent(s) (R$^9$)$_p$ on the benzene ring are those of Table 49.

TABLE 49

| H    | 3-Cl     | 2,3-diCH$_3$ | 2,6-diF      |
|------|----------|--------------|--------------|
| 2-Cl | 3-Br     | 2-Cl-6-F     | 2,3-diF      |
| 2-Br | 3-F      | 2-Cl-3-F     | 2-Cl-3,6-diF |
| 2-F  | 2,3-diCl | 3-Cl-2-F     |              |

The compounds of formula (25) wherein Q is NCH$_3$, R$^1$ is 1-methyl-2-propynyl, R$^2$ and R$^3$ are both hydrogen, and the substituent(s) (R$^9$)$_p$ on the benzene ring are those of Table 50.

TABLE 50

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_3$, $R^1$ is 2-butynyl, $R^2$ is hydrogen, $R^3$ is fluorine, and the substituent(s) $(R^9)_p$ on the benzene ring are those of Table 51.

TABLE 51

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-propynyl, $R^2$ and $R^3$ are both hydrogen, and the substituent(s) $(R^9)_p$ on the benzene ring are those of Table 52.

TABLE 52

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-propynyl, $R^2$ is methyl, $R^3$ is hydrogen, and the substituent(s) $(R^9)_p$ on the benzene ring are those of Table 53.

TABLE 53

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-propynyl, $R^2$ and $R^3$ are both methyl, and the substituent(s) $(R^9)_p$ on the benzene ring are those of Table 54.

TABLE 54

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-propynyl, $R^2$ is hydrogen, $R^3$ is methyl, and the substituent(s) $(R^9)_p$ on the benzene ring are those of Table 55.

TABLE 55

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-butynyl, $R^2$ and $R^3$ are both hydrogen, and the substituent(s) $(R^9)_p$ on the benzene ring are those of Table 56.

TABLE 56

| H       | 3-CN                | 2-OPh       | 2,6-diCH₃     |
|---------|---------------------|-------------|---------------|
| 2-Cl    | 4-CN                | 3-OPh       | 2-F-3-CF₃     |
| 3-Cl    | 2-SCH₃              | 4-OPh       | 2-F-6-CF₃     |
| 4-Cl    | 3-SCH₃              | 2-ethoxy    | 2-Cl-3-F      |
| 2-F     | 4-SCH₃              | 3-ethoxy    | 2-Cl-4-F      |
| 3-F     | 2-OCF₃              | 4-ethoxy    | 2-Cl-5-F      |
| 4-F     | 3-OCF₃              | 2-isopropyl | 2-Cl-6-F      |
| 2-Br    | 4-OCF₃              | 3-isopropyl | 3-Cl-2-F      |
| 3-Br    | 2-SCF₃              | 4-isopropyl | 2-Cl-4,6-diF  |
| 4-Br    | 3-SCF₃              | 2,3-diF     | 2,3-diCl      |
| 2-I     | 4-SCF₃              | 2,4-diF     | 2,4-diCl      |
| 3-I     | 2-CH₂CH₃            | 2,5-diF     | 2,5-diCl      |
| 4-I     | 3-CH₂CH₃            | 2,6-diF     | 2,6-diCl      |
| 2-OCH₃  | 4-CH₂CH₃            | 3,4-diF     | 3,4-diCl      |
| 3-OCH₃  | 2-propyl            | 3,5-diF     | 3,5-diCl      |
| 4-OCH₃  | 3-propyl            | 3,5-diCF₃   | 2,3,6-triCl   |
| 2-CH₃   | 4-propyl            | 2,3,6-triF  | 2,4,6-triCl   |
| 3-CH₃   | 2-NO₂               | 2,4,6-triF  | 2,6-diCl-4-F  |
| 4-CH₃   | 3-NO₂               | 3,4-diCH₃   | 2,3-diF-6-CF₃ |
| 2-CF₃   | 4-NO₂               | 3,5-diCH₃   | 2,3,4,6-tetraF|
| 3-CF₃   | 2-Ph                | 2,3-diCH₃   |               |
| 4-CF₃   | 3-Ph                | 2,4-diCH₃   |               |
| 2-CN    | 4-Ph                | 2,5-diCH₃   |               |

The compounds of formula (25) wherein Q is $NCH_2CH_3$, $R^1$ is 2-butynyl, $R^2$ is methyl, $R^3$ is hydrogen, and the substituent(s) $(R^9)_p$ on the benzene ring are those of Table 57.

TABLE 57

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-butynyl, $R^2$ and $R^3$ are both methyl, and the substituent(s) $(R^9)_p$ on the benzene ring are those of Table 58.

TABLE 58

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-butynyl, $R^2$ is hydrogen, $R^3$ is methyl, and the substituent(s) $(R^9)_p$ on the benzene ring are those of Table 59.

TABLE 59

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_3$, $R^1$ is 2-pentynyl, $R^2$ and $R^3$ are both hydrogen, and the substituent(s) $(R^9)_p$ on the benzene ring are those of Table 60.

TABLE 60

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_3$, R$^1$ is 1-methyl-2-butynyl, R$^2$ and R$^3$ are both hydrogen, and the substituent(s) (R$^9$)$_p$ on the benzene ring are those of Table 61.

TABLE 61

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_3$, R$^1$ is 1-methyl-2-propynyl, R$^2$ and R$^3$ are both hydrogen, and the substituent(s) (R$^9$)$_p$ on the benzene ring are those of Table 62.

TABLE 62

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_3$, R$^1$ is 2-butynyl, R$^2$ is hydrogen, R$^3$ is fluorine, and the substituent(s) (R$^9$)$_p$ on the benzene ring are those of Table 63.

TABLE 63

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-propynyl, R$^2$ and R$^3$ are both hydrogen, and the substituent(s) (R$^9$)$_p$ on the benzene ring are those of Table 64.

TABLE 64

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-propynyl, R$^2$ is methyl, and R$^3$ is hydrogen, and the substituent(s) (R$^9$)$_p$ on the benzene ring are those of Table 65.

TABLE 65

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-propynyl, R$^2$ and R$^3$ are both methyl, and the substituent(s) (R$^9$)$_p$ on the benzene ring are those of Table 66.

TABLE 66

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-propynyl, R$^2$ is hydrogen, R$^3$ is methyl, and the substituent(s) (R$^9$)$_p$ on the benzene ring are those of Table 67.

TABLE 67

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-butynyl, R$^2$ and R$^3$ are both hydrogen, and the substituent(s) (R$^9$)$_p$ on the benzene ring are those of Table 68.

TABLE 68

| H       | 3-CN                  | 2-OPh         | 2,6-diCH$_3$      |
|---------|-----------------------|---------------|-------------------|
| 2-Cl    | 4-CN                  | 3-OPh         | 2-F-3-CF$_3$      |
| 3-Cl    | 2-SCH$_3$             | 4-OPh         | 2-F-6-CF$_3$      |
| 4-Cl    | 3-SCH$_3$             | 2-ethoxy      | 2-Cl-3-F          |
| 2-F     | 4-SCH$_3$             | 3-ethoxy      | 2-Cl-4-F          |
| 3-F     | 2-OCF$_3$             | 4-ethoxy      | 2-Cl-5-F          |
| 4-F     | 3-OCF$_3$             | 2-isopropyl   | 2-Cl-6-F          |
| 2-Br    | 4-OCF$_3$             | 3-isopropyl   | 3-Cl-2-F          |
| 3-Br    | 2-SCF$_3$             | 4-isopropyl   | 2-Cl-4,6-diF      |
| 4-Br    | 3-SCF$_3$             | 2,3-diF       | 2,3-diCl          |
| 2-I     | 4-SCF$_3$             | 2,4-diF       | 2,4-diCl          |
| 3-I     | 2-CH$_2$CH$_3$        | 2,5-diF       | 2,5-diCl          |
| 4-I     | 3-CH$_2$CH$_3$        | 2,6-diF       | 2,6-diCl          |
| 2-OCH$_3$ | 4-CH$_2$CH$_3$      | 3,4-diF       | 3,4-diCl          |
| 3-OCH$_3$ | 2-propyl            | 3,5-diF       | 3,5-diCl          |
| 4-OCH$_3$ | 3-propyl            | 3,5-diCF$_3$  | 2,3,6-triCl       |
| 2-CH$_3$  | 4-propyl            | 2,3,6-triF    | 2,4,6-triCl       |
| 3-CH$_3$  | 2-NO$_2$            | 2,4,6-triF    | 2,6-diCl-4-F      |
| 4-CH$_3$  | 3-NO$_2$            | 3,4-diCH$_3$  | 2,3-diF-6-CF$_3$  |
| 2-CF$_3$  | 4-NO$_2$            | 3,5-diCH$_3$  | 2,3,4,6-tetraF    |
| 3-CF$_3$  | 2-Ph                | 2,3-diCH$_3$  |                   |
| 4-CF$_3$  | 3-Ph                | 2,4-diCH$_3$  |                   |
| 2-CN      | 4-Ph                | 2,5-diCH$_3$  |                   |

The compounds of formula (25) wherein Q is NCH$_2$CH$_2$CH$_3$, R$^1$ is 2-butynyl, R$^2$ is methyl, R$^3$ is hydrogen, and the substituent(s) (R$^9$)$_p$ on the benzene ring are those of Table 69.

TABLE 69

| H    | 3-Cl     | 2,3-diCH$_3$ | 2,6-diF       |
|------|----------|--------------|---------------|
| 2-Cl | 3-Br     | 2-Cl-6-F     | 2,3-diF       |
| 2-Br | 3-F      | 2-Cl-3-F     | 2-Cl-3,6-diF  |
| 2-F  | 2,3-diCl | 3-Cl-2-F     |               |

The compounds of formula (25) wherein Q is NCH$_2$CH$_2$CH$_3$, R$^1$ is 2-butynyl, R$^2$ and R$^3$ are both methyl, and the substituent(s) (R$^9$)$_p$ on the benzene ring are those of Table 70.

TABLE 70

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_2CH_3$, $R^1$ is 2-butynyl, $R^2$ is hydrogen, $R^3$ is methyl, and the substituent(s) $(R^9)_p$ on the benzene ring are those of Table 71.

TABLE 71

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_2CH_3$, $R^1$ is 2-pentynyl, $R^2$ and $R^3$ are both hydrogen, and the substituent(s) $(R^9)_p$ on the benzene ring are those of Table 72.

TABLE 72

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_2CH_3$, $R^1$ is 1-methyl-2-butynyl, $R^2$ and $R^3$ are both hydrogen, and the substituent(s) $(R^9)_p$ on the benzene ring are those of Table 73.

TABLE 73

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_2CH_3$, $R^1$ is 1-methyl-2-propynyl, $R^2$ and $R^3$ are both hydrogen, and the substituent(s) $(R^9)_p$ on the benzene ring are those of Table 74.

TABLE 74

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is $NCH_2CH_2CH_3$, $R^1$ is 2-butynyl, $R^2$ is hydrogen, $R^3$ is fluorine, and the substituent(s) $(R^9)_p$ on the benzene ring are those of Table 75.

TABLE 75

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is sulfur, $R^1$ is 2-propynyl, $R^2$ and $R^3$ are both hydrogen, and the substituent(s) $(R^9)_p$ on the benzene ring are those of Table 76.

TABLE 76

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is sulfur, $R^1$ is 2-propynyl, $R^2$ is methyl, $R^3$ is hydrogen, and the substituent(s) $(R^9)_p$ on the benzene ring are those of Table 77.

TABLE 77

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is sulfur, $R^1$ is 2-propynyl, $R^2$ and $R^3$ are both methyl, and the substituent(s) $(R^9)_p$ on the benzene ring are those of Table 78.

TABLE 78

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is sulfur, $R^1$ is 2-propynyl, $R^2$ is hydrogen, $R^3$ is methyl, and the substituent(s) $(R^9)_p$ on the benzene ring are those of Table 79.

TABLE 79

| H    | 3-Cl     | 2,3-diCH₃ | 2,6-diF      |
|------|----------|-----------|--------------|
| 2-Cl | 3-Br     | 2-Cl-6-F  | 2,3-diF      |
| 2-Br | 3-F      | 2-Cl-3-F  | 2-Cl-3,6-diF |
| 2-F  | 2,3-diCl | 3-Cl-2-F  |              |

The compounds of formula (25) wherein Q is sulfur, $R^1$ is 2-butynyl, $R^2$ and $R^3$ are both hydrogen, and the substituent(s) $(R^9)_p$ on the benzene ring are those of Table 80.

TABLE 80

| H       | 2-CH₃    | 3-SCF₃    | 2-Cl-3-F       |
|---------|----------|-----------|----------------|
| 2-Cl    | 3-CH₃    | 4-SCF₃    | 2-Cl-6-F       |
| 3-Cl    | 4-CH₃    | 2,3-diF   | 2-Cl-4,6-diF   |
| 4-Cl    | 2-CF₃    | 2,4-diF   | 2,3-diCl       |
| 2-F     | 3-CF₃    | 2,5-diF   | 2,3-diCH₃      |
| 3-F     | 4-CF₃    | 2,6-diF   | 2,3,6-triF     |
| 4-F     | 2-OCF₃   | 3,4-diF   | 2,4,6-triF     |
| 2-OCH₃  | 3-OCF₃   | 3,5-diF   | 2,3,4,6-tetraF |
| 3-OCH₃  | 4-OCF₄   | 2-F-3-CF₃ |                |
| 4-OCH₄  | 2-SCF₃   | 2-F-6-CF₃ |                |

The compounds of formula (25) wherein Q is sulfur, $R^1$ is 2-butynyl, $R^2$ is methyl, $R^3$ is hydrogen, and the substituent(s) $(R^9)_p$ on the benzene ring are those of Table 81.

TABLE 81

| H    | 3-Cl | 2,3-diCH₃ | 2,6-diF |
|------|------|-----------|---------|
| 2-Cl | 3-Br | 2-Cl-6-F  | 2,3-diF |

TABLE 81-continued

| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 2-butynyl, $R^2$ and $R^3$ are both methyl, and the substituent(s) $(R^9)_p$ on the benzene ring are those of Table 82.

TABLE 82

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 2-butynyl, $R^2$ is hydrogen, $R^3$ is methyl, and the substituent(s) $(R^9)_p$ on the benzene ring are those of Table 83.

TABLE 83

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 2-pentynyl, $R^2$ and $R^3$ are both hydrogen, and the substituent(s) $(R^9)_p$ on the benzene ring are those of Table 84.

TABLE 84

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 1-methyl-2-butynyl, $R^2$ and $R^3$ are both hydrogen, and the substituent(s) $(R^9)_p$ on the benzene ring are those of Table 85.

TABLE 85

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 1-methyl-2-propynyl, $R^2$ and $R^3$ are both hydrogen, and the substituent(s) $(R^9)_p$ on the benzene ring are those of Table 86.

TABLE 86

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is sulfur, $R^1$ is 2-butynyl, $R^2$ is hydrogen, $R^3$ is fluorine, and the substituent(s) $(R^9)_p$ on the benzene ring are those of Table 87.

TABLE 87

| H | 3-Cl | 2,3-diCH$_3$ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (25) wherein Q is CHCN, $R^1$ is 2-propynyl, $R^2$ and $R^3$ are both hydrogen, and the substituent(s) $(R^9)_p$ on the benzene ring are those of Table 88.

TABLE 88

| H | 2-Cl | 2,3-diF | 2,6-diF |
| 2-F | 3-F | 2-Cl-6-F | 2,3-diCl |

The compounds of formula (25) wherein Q is CHCN, $R^1$ is 2-butynyl, $R^2$ and $R^3$ are both hydrogen, and the substituent(s) $(R^9)_p$ on the benzene ring are those of Table 89.

TABLE 89

| H | 2-Cl | 2,3-diF | 2,6-diF |
| 2-F | 3-F | 2-Cl-6-F | 2,3-diCl |

The compounds of formula (25) wherein Q is carbonyl, $R^1$ is 2-propynyl, $R^2$ and $R^3$ are both hydrogen, and the substituent(s) $(R^9)_p$ on the benzene ring are those of Table 90.

TABLE 90

| H | 2-Cl | 2,3-diF | 2,6-diF |
| 2-F | 3-F | 2-Cl-6-F | 2,3-diCl |

The compounds of formula (25) wherein Q is carbonyl, $R^1$ is 2-butynyl, $R^2$ and $R^3$ are both hydrogen, and the substituent(s) $(R^9)_p$ on the benzene ring are those of Table 91.

TABLE 91

| H | 2-Cl | 2,3-diF | 2,6-diF |
| 2-F | 3-F | 2-Cl-6-F | 2,3-diCl |

The compounds of formula (26):

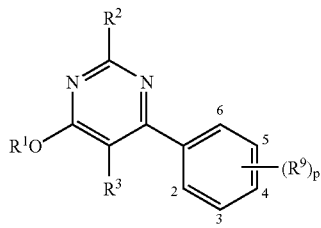

(26)

wherein $R^1$ is 2-propynyl, $R^2$ and $R^3$ are both hydrogen, and the substituent(s) $(R^9)_p$ on the benzene ring are selected from those of Table 92.

TABLE 92

| | | | |
|---|---|---|---|
| H | 2-CH₃ | 3-SCF₃ | 2-Cl-3-F |
| 2-Cl | 3-CH₃ | 4-SCF₃ | 2-Cl-6-F |
| 3-Cl | 4-CH₃ | 2,3-diF | 2-Cl-4,6-diF |
| 4-Cl | 2-CF₃ | 2,4-diF | 2,3-diCl |
| 2-F | 3-CF₃ | 2,5-diF | 2,3-diCH₃ |
| 3-F | 4-CF₃ | 2,6-diF | 2,3,6-triF |
| 4-F | 2-OCF₃ | 3,4-diF | 2,4,6-triF |
| 2-OCH₃ | 3-OCF₃ | 3,5-diF | 2,3,4,6-tetraF |
| 3-OCH₃ | 4-OCF₄ | 2-F-3-CF₃ | |
| 4-OCH₄ | 2-SCF₃ | 2-F-6-CF₃ | |

The compounds of formula (26) wherein $R^1$ is 2-propynyl, $R^2$ is methyl, $R^3$ is hydrogen, and the substituent(s) $(R^9)_p$ on the benzene ring are selected from those of Table 93.

TABLE 93

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-propynyl, $R^2$ and $R^3$ are both methyl, and the substituent(s) $(R^9)_p$ on the benzene ring are selected from those of Table 94.

TABLE 94

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-propynyl, $R^2$ is hydrogen, $R^3$ is methyl, and the substituent(s) $(R^9)_p$ on the benzene ring are selected from those of Table 95.

TABLE 95

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-butynyl, $R^2$ and $R^3$ are both hydrogen, and the substituent(s) $(R^9)_p$ on the benzene ring are selected from those of Table 96.

TABLE 96

| | | | |
|---|---|---|---|
| H | 3-CN | 2-OPh | 2,6-diCH₃ |
| 2-Cl | 4-CN | 3-OPh | 2-F-3-CF₃ |
| 3-Cl | 2-SCH₃ | 4-OPh | 2-F-6-CF₃ |
| 4-Cl | 3-SCH₃ | 2-ethoxy | 2-Cl-3-F |
| 2-F | 4-SCH₃ | 3-ethoxy | 2-Cl-4-F |
| 3-F | 2-OCF₃ | 4-ethoxy | 2-Cl-5-F |
| 4-F | 3-OCF₃ | 2-isopropyl | 2-Cl-6-F |
| 2-Br | 4-OCF₃ | 3-isopropyl | 3-Cl-2-F |
| 3-Br | 2-SCF₃ | 4-isopropyl | 2-Cl-4,6-diF |
| 4-Br | 3-SCF₃ | 2,3-diF | 2,3-diCl |
| 2-I | 4-SCF₃ | 2,4-diF | 2,4-diCl |
| 3-I | 2-CH₂CH₃ | 2,5-diF | 2,5-diCl |
| 4-I | 3-CH₂CH₃ | 2,6-diF | 2,6-diCl |
| 2-OCH₃ | 4-CH₂CH₃ | 3,4-diF | 3,4-diCl |
| 3-OCH₃ | 2-propyl | 3,5-diF | 3,5-diCl |
| 4-OCH₃ | 3-propyl | 3,5-diCF₃ | 2,3,6-triCl |
| 2-CH₃ | 4-propyl | 2,3,6-triF | 2,4,6-triCl |
| 3-CH₃ | 2-NO₂ | 2,4,6-triF | 2,6-diCl-4-F |
| 4-CH₃ | 3-NO₂ | 3,4-diCH₃ | 2,3-diF-6-CF₃ |

TABLE 96-continued

| | | | |
|---|---|---|---|
| 2-CF₃ | 4-NO₂ | 3,5-diCH₃ | 2,3,4,6-tetraF |
| 3-CF₃ | 2-Ph | 2,3-diCH₃ | |
| 4-CF₃ | 3-Ph | 2,4-diCH₃ | |
| 2-CN | 4-Ph | 2,5-diCH₃ | |

The compounds of formula (26) wherein $R^1$ is 2-butynyl, $R^2$ is methyl, $R^3$ is hydrogen, and the substituent(s) $(R^9)_p$ on the benzene ring are those of Table 97.

TABLE 97

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-butynyl, $R^2$ and $R^3$ are both methyl, and the substituent(s) $(R^9)_p$ on the benzene ring are those of Table 98.

TABLE 98

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-butynyl, $R^2$ is hydrogen, $R^3$ is methyl, and the substituent(s) $(R^9)_p$ on the benzene ring are those of Table 99.

TABLE 99

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-pentynyl, $R^2$ and $R^3$ are both hydrogen, and the substituent(s) $(R^9)_p$ on the benzene ring are those of Table 100.

TABLE 100

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 3-butynyl, $R^2$ and $R^3$ are both hydrogen, and the substituent(s) $(R^9)_p$ on the benzene ring are those of Table 101.

TABLE 101

| | | | |
|---|---|---|---|
| H | 3-Cl | 2,3-diCH₃ | 2,6-diF |
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 1-methyl-2-butynyl, $R^2$ and $R^3$ are both hydrogen, and the substituent(s) $(R^9)_p$ on the benzene ring are those of Table 102.

TABLE 102

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 1-methyl-2-propynyl, $R^2$ and $R^3$ are both hydrogen, and the substituent(s) $(R^9)_p$ on the benzene ring are those of Table 103.

TABLE 103

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 3-pentynyl, $R^2$ and $R^3$ are both hydrogen, and the substituent(s) $(R^9)_p$ on the benzene ring are those of Table 104.

TABLE 104

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 3-chloro-2-propynyl, $R^2$ and $R^3$ are both hydrogen, and the substituent(s) $(R^9)$ on the benzene ring are those of Table 105.

TABLE 105

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 4-fluoro-2-butynyl, $R^2$ and $R^3$ are both hydrogen, and the substituent(s) $(R^9)_p$ on the benzene ring are those of Table 106.

TABLE 106

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-heptynyl, $R^1$ and $R^3$ are both hydrogen, and the substituent(s) $(R^9)_p$ on the benzene ring are those of Table 107.

TABLE 107

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (26) wherein $R^1$ is 2-butynyl, $R^2$ is hydrogen, $R^3$ is fluorine, and the substituent(s) $(R^9)_p$ on the benzene ring are those of Table 108.

TABLE 108

| H | 3-Cl | 2,3-diCH$_3$ | 2,6-diF |
|---|---|---|---|
| 2-Cl | 3-Br | 2-Cl-6-F | 2,3-diF |
| 2-Br | 3-F | 2-Cl-3-F | 2-Cl-3,6-diF |
| 2-F | 2,3-diCl | 3-Cl-2-F | |

The compounds of formula (27):

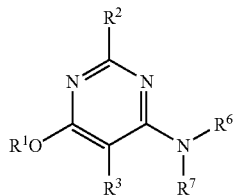

(27)

wherein $R^1$ is 2-propynyl, $R^2$, $R^3$, and $R^7$ are all hydrogen, and $R^6$ is selected from those of Table 109.

TABLE 109

| H | CH$_3$ | 1-CH$_3$-2-propenyl | 2-CH$_3$-2-propenyl |
|---|---|---|---|
| CH$_2$CH$_3$ | (CH$_2$)$_2$CH$_3$ | 3-Cl-2-propenyl | 2-Cl-2-propenyl |
| CH(CH$_3$)$_2$ | (CH$_2$)$_3$CH$_3$ | 3,3-diCl-2-propenyl | 3,3-diF-2-propenyl |
| CH$_2$CH(CH$_3$)$_2$ | C(CH$_3$)$_3$ | 2-propynyl | 2-butynyl |
| allyl | 2-butenyl | 2-pentynyl | 2,2,2-trifluoroethyl |

The compounds of formula (27) wherein $R^1$ is 2-butynyl, $R^2$, $R^3$, and $R^7$ are all hydrogen, and $R^6$ is selected from those of Table 110.

TABLE 110

| H | CH$_3$ | 1-CH$_3$-2-propenyl | 2-CH$_3$-2-propenyl |
|---|---|---|---|
| CH$_2$CH$_3$ | (CH$_2$)$_2$CH$_3$ | 3-Cl-2-propenyl | 2-Cl-2-propenyl |
| CH(CH$_3$)$_2$ | (CH$_2$)$_3$CH$_3$ | 3,3-diCl-2-propenyl | 3,3-diF-2-propenyl |
| CH$_2$CH(CH$_3$)$_2$ | C(CH$_3$)$_3$ | 2-propynyl | 2-butynyl |
| allyl | 2-butenyl | 2-pentynyl | 2,2,2-trifluoroethyl |

The compounds of formula (27) wherein $R^1$ is 2-pentynyl, $R^2$, $R^3$, and $R^7$ are all hydrogen, and $R^6$ is selected from those of Table 111.

TABLE 111

| H | CH$_3$ | 1-CH$_3$-2-propenyl | 2-CH$_3$-2-propenyl |
|---|---|---|---|
| CH$_2$CH$_3$ | (CH$_2$)$_2$CH$_3$ | 3-Cl-2-propenyl | 2-Cl-2-propenyl |
| CH(CH$_3$)$_2$ | (CH$_2$)$_3$CH$_3$ | 3,3-diCl-2-propenyl | 3,3-diF-2-propenyl |
| CH$_2$CH(CH$_3$)$_2$ | C(CH$_3$)$_3$ | 2-propynyl | 2-butynyl |
| allyl | 2-butenyl | 2-pentynyl | 2,2,2-trifluoroethyl |

The compounds of formula (27) wherein $R^1$ is 2-propynyl, $R^2$ and $R^3$ are both hydrogen, $R^7$ is methyl, and $R^6$ is selected from those of Table 112.

TABLE 112

| CH$_2$CH$_3$ | CH$_3$ | 1-CH$_3$-2-propenyl | 2-CH$_3$-2-propenyl |
|---|---|---|---|
| CH(CH$_3$)$_2$ | (CH$_2$)$_2$CH$_3$ | 3-Cl-2-propenyl | 2-Cl-2-propenyl |
| CH$_2$CH(CH$_3$)$_2$ | (CH$_2$)$_3$CH$_3$ | 3,3-diCl-2-propenyl | 3,3-diF-2-propenyl |
| allyl | C(CH$_3$)$_3$ | 2-propynyl | 2-butynyl |
| 2-butenyl | 2-pentynyl | 2,2,2-trifluoroethyl | |

The compounds of formula (27) wherein $R^1$ is 2-butynyl, $R^2$ and $R^3$ are both hydrogen, $R^7$ is methyl, and $R^6$ is selected from those of Table 113.

TABLE 113

| | | | |
|---|---|---|---|
| CH$_2$CH$_3$ | CH$_3$ | 1-CH$_3$-2-propenyl | 2-CH$_3$-2-propenyl |
| CH(CH$_3$)$_2$ | (CH$_2$)$_2$CH$_3$ | 3-Cl-2-propenyl | 2-Cl-2-propenyl |
| CH$_2$CH(CH$_3$)$_2$ | (CH$_2$)$_3$CH$_3$ | 3,3-diCl-2-propenyl | 3,3-diF-2-propenyl |
| allyl | C(CH$_3$)$_3$ | 2-propynyl | 2-butynyl |
| 2-butenyl | 2-pentynyl | 2,2,2-trifluoroethyl | |

The compounds of formula (27) wherein $R^1$ is 2-pentynyl, $R^2$ and $R^3$ are both hydrogen, $R^7$ is methyl, and $R^6$ is selected from those of Table 114.

TABLE 114

| | | | |
|---|---|---|---|
| CH$_2$CH$_3$ | CH$_3$ | 1-CH$_3$-2-propenyl | 2-CH$_3$-2-propenyl |
| CH(CH$_3$)$_2$ | (CH$_2$)$_2$CH$_3$ | 3-Cl-2-propenyl | 2-Cl-2-propenyl |
| CH$_2$CH(CH$_3$)$_2$ | (CH$_2$)$_3$CH$_3$ | 3,3-diCl-2-propenyl | 3,3-diF-2-propenyl |
| allyl | C(CH$_3$)$_3$ | 2-propynyl | 2-butynyl |
| 2-butenyl | 2-pentynyl | 2,2,2-trifluoroethyl | |

The compounds of formula (27) wherein $R^1$ is 2-propynyl, $R^2$ and $R^3$ are both hydrogen, $R^7$ is ethyl, and $R^6$ is selected from those of Table 115.

TABLE 115

| | | | |
|---|---|---|---|
| CH$_2$CH$_3$ | (CH$_2$)$_2$CH$_3$ | 1-CH$_3$-2-propenyl | 2-CH$_3$-2-propenyl |
| CH(CH$_3$)$_2$ | (CH$_2$)$_3$CH$_3$ | 3-Cl-2-propenyl | 2-Cl-2-propenyl |
| CH$_2$CH(CH$_3$)$_2$ | C(CH$_3$)$_3$ | 3,3-diCl-2-propenyl | 3,3-diF-2-propenyl |
| allyl | 2-pentynyl | 2-propynyl | 2,2,2-trifluoroethyl |
| 2-butenyl | 2-butynyl | | |

The compounds of formula (27) wherein $R^1$ is 2-butynyl, $R^2$ and $R^3$ are both hydrogen, $R^7$ is ethyl, and $R^6$ is selected from those of Table 116.

TABLE 116

| | | | |
|---|---|---|---|
| CH$_2$CH$_3$ | (CH$_2$)$_2$CH$_3$ | 1-CH$_3$-2-propenyl | 2-CH$_3$-2-propenyl |
| CH(CH$_3$)$_2$ | (CH$_2$)$_3$CH$_3$ | 3-Cl-2-propenyl | 2-Cl-2-propenyl |
| CH$_2$CH(CH$_3$)$_2$ | C(CH$_3$)$_3$ | 3,3-diCl-2-propenyl | 3,3-diF-2-propenyl |
| allyl | 2-pentynyl | 2-propynyl | 2,2,2-trifluoroethyl |
| 2-butenyl | 2-butynyl | | |

The compounds of formula (27) wherein $R^1$ is 2-pentynyl, $R^2$ and $R^3$ are both hydrogen, $R^7$ is ethyl, and $R^6$ is selected from those of Table 117.

TABLE 117

| | | | |
|---|---|---|---|
| CH$_2$CH$_3$ | (CH$_2$)$_2$CH$_3$ | 1-CH$_3$-2-propenyl | 2-CH$_3$-2-propenyl |
| CH(CH$_3$)$_2$ | (CH$_2$)$_3$CH$_3$ | 3-Cl-2-propenyl | 2-Cl-2-propenyl |
| CH$_2$CH(CH$_3$)$_2$ | C(CH$_3$)$_3$ | 3,3-diCl-2-propenyl | 3,3-diF-2-propenyl |
| allyl | 2-pentynyl | 2-propynyl | 2,2,2-trifluoroethyl |
| 2-butenyl | 2-butynyl | | |

The compounds of formula (27) wherein $R^1$ is 2-pentynyl, $R^2$ and $R^3$ are both hydrogen, $R^7$ is propyl, and $R^6$ is selected from those of Table 118.

TABLE 118

| | | | |
|---|---|---|---|
| CH(CH$_3$)$_2$ | (CH$_2$)$_2$CH$_3$ | 1-CH$_3$-2-propenyl | 2-CH$_3$-2-propenyl |
| CH$_2$CH(CH$_3$)$_2$ | (CH$_2$)$_3$CH$_3$ | 3-Cl-2-propenyl | 2-Cl-2-propenyl |
| allyl | C(CH$_3$)$_3$ | 3,3-diCl-2-propenyl | 3,3-diF-2-propenyl |
| 2-butenyl | 2-pentynyl | 2-propynyl | 2,2,2-trifluoroethyl |
| 2-butynyl | | | |

The compounds of formula (27) wherein $R^1$ is 2-butynyl, $R^2$ and $R^3$ are both hydrogen, $R^7$ is propyl, and $R^6$ is selected from those of Table 119.

TABLE 119

| | | | |
|---|---|---|---|
| CH(CH$_3$)$_2$ | (CH$_2$)$_2$CH$_3$ | 1-CH$_3$-2-propenyl | 2-CH$_3$-2-propenyl |
| CH$_2$CH(CH$_3$)$_2$ | (CH$_2$)$_3$CH$_3$ | 3-Cl-2-propenyl | 2-Cl-2-propenyl |
| allyl | C(CH$_3$)$_3$ | 3,3-diCl-2-propenyl | 3,3-diF-2-propenyl |
| 2-butenyl | 2-pentynyl | 2-propynyl | 2,2,2-trifluoroethyl |
| 2-butynyl | | | |

The compounds of formula (27) wherein $R^1$ is 2-pentynyl, $R^2$ and $R^3$ are both hydrogen, $R^7$ is propyl, and $R^6$ is selected from those of Table 120.

TABLE 120

| | | | |
|---|---|---|---|
| CH(CH$_3$)$_2$ | (CH$_2$)$_2$CH$_3$ | 1-CH$_3$-2-propenyl | 2-CH$_3$-2-propenyl |
| CH$_2$CH(CH$_3$)$_2$ | (CH$_2$)$_3$CH$_3$ | 3-Cl-2-propenyl | 2-Cl-2-propenyl |
| allyl | C(CH$_3$)$_3$ | 3,3-diCl-2-propenyl | 3,3-diF-2-propenyl |
| 2-butenyl | 2-pentynyl | 2-propynyl | 2,2,2-trifluoroethyl |
| 2-butynyl | | | |

The compounds of formula (27) wherein $R^1$ is 2-propynyl, $R^2$ and $R^3$ are both hydrogen, $R^7$ is propyl, and $R^6$ is selected from those of Table 121.

TABLE 121

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | 2,2,2-trifluoroethyl |

The compounds of formula (27) wherein $R^1$ is 2-butynyl, $R^2$ and $R^3$ are both hydrogen, $R^7$ is 1-methylethyl, and $R^6$ is selected from those of Table 122.

TABLE 122

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | 2,2,2-trifluoroethyl |

The compounds of formula (27) wherein $R^1$ is 2-pentynyl, $R^2$ and $R^3$ are both hydrogen, $R^7$ is 1-methylethyl, and $R^6$ is selected from those of Table 123.

TABLE 123

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | 2,2,2-trifluoroethyl |

The compounds of formula (27) wherein $R^1$ is 2-propynyl, $R^2$ and $R^3$ are both hydrogen, $R^7$ is 2,2,2-trifluoroethyl, and $R^6$ is selected from those of Table 124.

TABLE 124

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | |

The compounds of formula (27) wherein $R^1$ is 2-butynyl, $R^2$ and $R^3$ are both hydrogen, $R^7$ is 2,2,2-trifluoroethyl, and $R^6$ is selected from those of Table 125.

TABLE 125

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | |

The compounds of formula (27) wherein $R^1$ is 2-pentynyl, $R^2$ and $R^3$ are both hydrogen, $R^7$ is 2,2,2-trifluoroethyl, and $R^6$ is selected from those of Table 126.

TABLE 126

| | | | |
|---|---|---|---|
| CH$_2$CH(CH$_3$)$_2$ | (CH$_2$)$_2$CH$_3$ | 1-CH$_3$-2-propenyl | 2-CH$_3$-2-propenyl |
| allyl | (CH$_2$)$_3$CH$_3$ | 3-Cl-2-propenyl | 2-Cl-2-propenyl |
| 2-butenyl | C(CH$_3$)$_3$ | 3,3-diCl-2-propenyl | 3,3-diF-2-propenyl |
| 2-butynyl | 2-pentynyl | 2-propynyl | |

The compounds of formula (28):

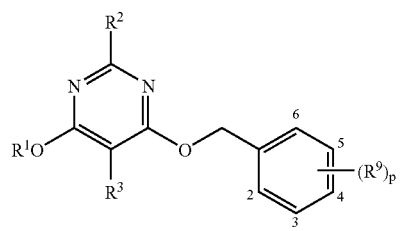

(28)

wherein $R^1$ is 2-propynyl, $R^2$ and $R^3$ are both hydrogen, and the substituent(s) $(R^9)_p$ on the benzene ring are selected from those of Table 127.

TABLE 127

| | | | |
|---|---|---|---|
| H | 2-Cl | 2,3-diF | 2,6-diF |
| 2-F | 3-F | 2-Cl-6-F | 2,3-diCl |

The compounds of formula (28) wherein $R^1$ is 2-butynyl, $R^2$ and $R^3$ are both hydrogen, and the substituent(s) $(R^9)_p$ on the benzene ring are selected from those of Table 128.

TABLE 128

| | | | |
|---|---|---|---|
| H | 2-Cl | 2,3-diF | 2,6-diF |
| 2-F | 3-F | 2-Cl-6-F | 2,3-diCl |

The compounds of formula (29):

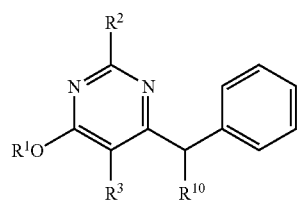

(29)

wherein $R^1$ is 2-butynyl, $R^2$ and $R^3$ are both hydrogen, and $R^{10}$ is selected from those of Table 129.

TABLE 129

| F | OCH$_3$ | OC$_2$H$_5$ |
|---|---|---|

The compounds of formula (30):

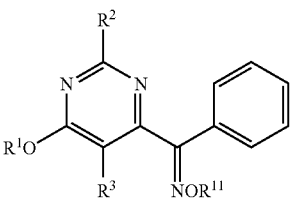

(30)

wherein $R^1$ is 2-butynyl, $R^2$ and $R^3$ are both hydrogen, and $R^{11}$ is selected from those of Table 130.

TABLE 130

| CH$_3$ | C$_2$H$_5$ | CH(CH$_3$)$_2$ |
|---|---|---|

The compounds of formula (31):

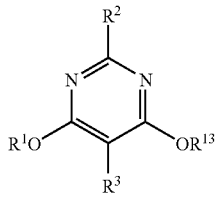

(31)

wherein $R^2$ and $R^3$ are both hydrogen and $R^1$ and $R^{13}$ make a combination as defined in Table 131.

TABLE 131

| $R^1$ | $R^{13}$ |
|---|---|
| 2-propynyl | 2-propynyl |
| 2-propynyl | 2-butynyl |
| 2-propynyl | 2-pentynyl |
| 2-butynyl | 2-butynyl |
| 2-propynyl | 3-butynyl |
| 2-butynyl | 2-pentynyl |
| 2-propynyl | 1-methyl-2-propynyl |
| 2-butynyl | 1-methyl-2-propynyl |
| 2-butynyl | 4,4-diemthyl-2-pentynyl |
| 4,4-dimethyl-2-pentynyl | 4,4-dimethyl-2-pentynyl |

Production Process 1

A production process for the present compounds wherein $R^4$ is C$_3$-C$_7$ alkynyloxy optionally substituted with halogen or a group of formula -A$^{1-1}$R$^5$ wherein A$^{1-1}$ is oxygen or sulfur; and R$^5$ is optionally substituted phenyl or optionally substituted C$_7$-C$_9$ aralkyl.

The present compounds of formula (4) can be produced from the 4,6-dichloropyrimidine compounds of formula (2) though step (1-1) and step (1-2) according to the following scheme.

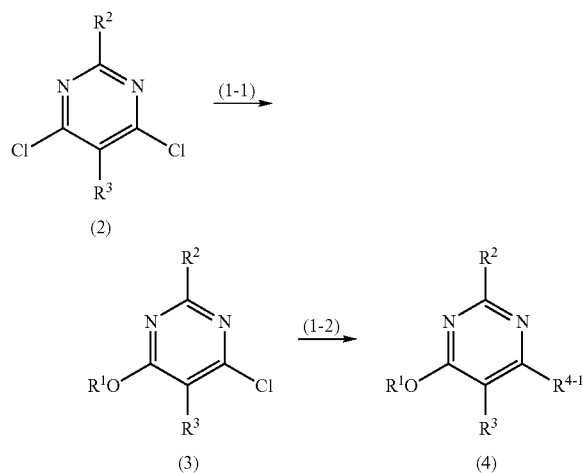

wherein $R^1$ is $C_3$-$C_7$ alkynyl optionally substituted with halogen; $R^2$ and $R^3$ are the same or different and are independently hydrogen, halogen or $C_1$-$C_4$ alkyl; and $R^{4-1}$ is $C_3$-$C_7$ alkynyloxy optionally substituted with halogen or a group of formula $A^{1-1}R^{5-1}$ wherein $A^{1-1}$ is oxygen or sulfur; and $R^{5-1}$ is optionally substituted phenyl or optionally substituted $C_7$-$C_9$ aralkyl.

Step (1-1)

The compounds of formula (3) can be produced by reacting the 4,6-dichloropyrimidine compounds of formula (2) with the compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; dimethylsulfoxide; and mixtures thereof.

The base used in the reaction may include inorganic bases such as sodium hydride. The amount of the base used in the reaction is usually in the range of 1 to 1.5 moles, relative to 1 mole of the 4,6-dichloropyrimidine compound of formula (2).

The amount of the alcohol compound of formula $R^1OH$ used in the reaction is usually in the range of 1 to 1.2 moles, relative to 1 mole of the 4,6-dichloropyrimidine compound of formula (2).

The reaction temperature is usually in the range of 0° C. to 80° C.

The reaction time is usually in the range of 0.1 to 12 hours.

After completion of the reaction, the reaction mixture is subjected to the ordinary post-treatment including extraction with an organic solvent and concentration for isolation of the compounds of formula (3). The compounds of formula (3) thus isolated may be purified by chromatography or other techniques.

Step (1-2)

The present compounds of formula (4) can be produced by reacting the compounds of formula (3) with the compounds of formula $R^{4-1}H$ wherein $R^{4-1}$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; dimethylsulfoxide; acetonitrile; and mixtures thereof.

The base used in the reaction may include inorganic bases such as sodium hydride and potassium carbonate; tertiary amines such as triethylamine and diisopropylethylamine; and nitrogen-containing aromatic compounds such as pyridine. The amount of the base used in the reaction is usually in the range of 1 to 1.5 moles, relative to 1 mole of the compound of formula (3).

The amount of the compound of formula $R^{4-1}H$ used in the reaction is usually in the range of 1 to 1.2 moles, relative to 1 mole of the compound of formula (3).

The reaction temperature is usually in the range of 0° C. to 80° C.

The reaction time is usually in the range of 0.1 to 12 hours.

After completion of the reaction, the reaction mixture is subjected to the ordinary post-treatment including extraction with an organic solvent and concentration for isolation of the compounds of formula (4). The compounds of formula (4) thus isolated may be purified by chromatography or other techniques.

Production Process 2

A production process for the present compounds wherein $R^4$ is a group of formula -$A^1R^5$; $A^1$ is oxygen; and $R^5$ is optionally substituted $C_7$-$C_9$ aralkyl.

The present compounds of formula (8) can be produced from the 4,6-dichloropyrimidine compounds of formula (2) through step (2-1) to step (2-4) according to the following scheme.

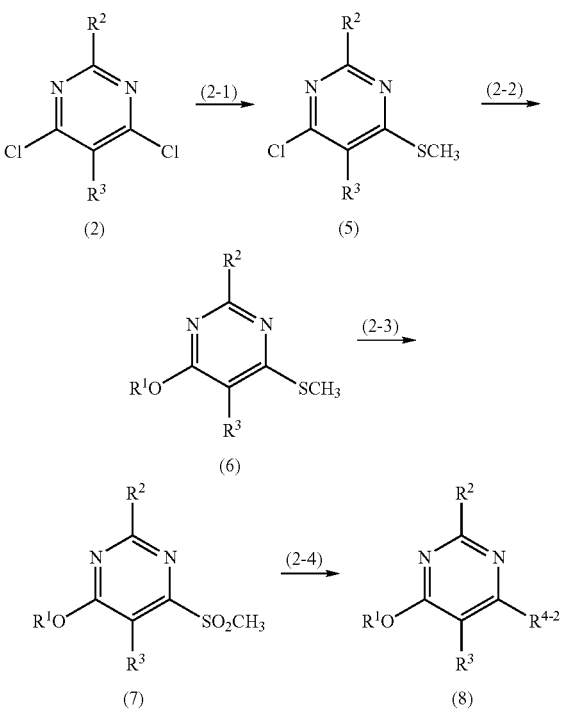

wherein $R^1$, $R^2$, and $R^3$ are as defined above and $R^{4-2}$ is a group of formula —$OR^{5-2}$ wherein $R^{5-2}$ is optionally substituted $C_7$-$C_9$ aralkyl.

Step (2-1)

The compounds of formula (5) can be produced by reacting the compounds of formula (2) with sodium thiomethoxide.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; alcohols such as methanol and ethanol; dimethylsulfoxide; acetonitrile; and mixtures thereof.

The amount of methanethiol sodium salt used in the reaction is usually in the range of 1 to 1.5 moles, relative to 1 mole of the compound of formula (2).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (5). The compounds of formula (5) thus isolated may be purified by chromatography or other techniques.

Step (2-2)

The compounds of formula (6) can be produced by reacting the compounds of formula (5) with the compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (5).

The amount of the alcohol compound of formula $R^1OH$ used in the reaction is usually in the range of 1 to 1.2 moles, relative to 1 mole of the compound of formula (5).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (6). The compounds of formula (6) thus isolated may be purified by chromatography or other techniques.

Step (2-3)

The compounds of formula (7) can be produced by oxidation reaction of the compounds of formula (6).

The oxidation reaction is usually carried out in a solvent. The solvent used in the reaction may include halogenated hydrocarbons such as chloroform and methylene chloride; nitrites such as acetonitrile; aromatic hydrocarbons such as benzene and toluene; and mixtures thereof.

The oxidizing agent used in the reaction may include peracids such as 3-chloroperbenzoic acid and peracetic acid. The amount of the oxidizing agent is usually in the range of 2 to 2.5 moles, relative to 1 mole of the compound of formula (6).

The reaction temperature is usually in the range of 0° C. to 80° C.

The reaction time is usually in the range of 1 to 12 hours.

After completion of the reaction, the reaction mixture is treated with a reducing agent such as an aqueous sodium thiosulfate solution and then subjected to the ordinary post-treatment including extraction with an organic solvent and concentration for isolation of the compounds of formula (7). The compounds of formula (7) thus isolated may be purified by chromatography or other techniques.

Step (2-4)

The compounds of formula (8) can be produced by reacting the compounds of formula (7) with the compounds of formula $R^{5-2}OH$ wherein $R^{5-2}$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium carbonate and potassium carbonate. The amount of the base used in the reaction is usually in the range of 1 to 1.5 moles, relative to 1 mole of the compound of formula (7).

The amount of the compound of formula $R^{5-2}OH$ used in the reaction is usually in the range of 1 to 1.2 moles, relative to 1 mole of the compound of formula (7).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (8). The compounds of formula (8) thus isolated may be purified by chromatography or other techniques.

Production Process 3

A production process for the present compounds wherein $R^4$ is a group of formula $A^1R^5$; $A^1$ is oxygen; and $R^5$ is optionally substituted $C_7$-$C_9$ aralkyl, or $R^4$ is $C_3$-$C_8$ cycloalkoxy optionally substituted with halogen, hydroxy, $C_1$-$C_4$ alkyl or $C_1$-$C_4$ alkoxy.

The present compounds of formula (10) can be produced from the 4,6-dichloropyrimidine compounds of formula (2) thought step (3-1) and step (3-2) according to the following scheme.

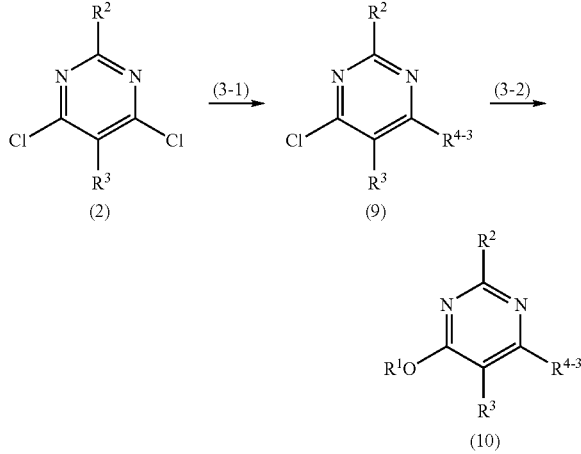

wherein $R^1$, $R^2$, and $R^3$ are as defined above and $R^{4-3}$ is a group of formula $A^1R^{5-3}$; $A^1$ is oxygen; and $R^{5-3}$ is optionally substituted $C_7$-$C_9$ aralkyl, or $R^{4-3}$ is $C_3$-$C_8$ cycloalkoxy optionally substituted with halogen, hydroxy, $C_1$-$C_4$ alkyl or $C_1$-$C_4$ alkoxy.

Step (3-1)

The compounds of formula (9) can be produced by reacting the 4,6-dichlorophyrimidine compounds of formula (2) with the alcohol compounds of formula $R^{4-1}H$ wherein $R^{4-3}$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; dimethylsulfoxide; and mixtures thereof.

The base used in the reaction may include inorganic bases such as sodium hydride. The amount of the base used in the reaction is usually in the range of 1 to 1.5 moles, relative to 1 mole of the 4,6-dichlorophyrimidine compound of formula (2).

The amount of the alcohol compound of formula $R^{4-3}H$ used in the reaction is usually in the range of 1 to 1.2 moles, relative to 1 mole of the 4,6-dichlorophyrimidine compound of formula (2).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (9). The compounds of formula (9) thus isolated may be purified by chromatography or other techniques.

Step (3-2)

The compounds of formula (10) can be produced by reacting the compounds of formula (9) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (9).

The amount of the alcohol compound of formula $R^1OH$ used in the reaction is usually in the range of 1 to 1.2 moles, relative to 1 mole of the compound of formula (9).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (10). The compounds of formula (10) thus isolated may be purified by chromatography or other techniques.

Production Process 4

A production process for the present compounds wherein $R^4$ is optionally substituted phenyl.

The present compounds of formula (12) can be produced thought step (41-) and step (4-2) according to the following scheme.

wherein $R^1$, $R^2$, and $R^3$ are as defined above and $R^{4-4}$ is optionally substituted phenyl.

Step (4-1)

The compounds of formula (11) can be produced by reacting the 4,6-dichloropyrimidine compounds of formula (2) with the phenylboronic acid compounds of formula $R^{4-4}B(OH)_2$ wherein $R^{4-4}$ is as defined above in the presence of a transition metal compound under an atmosphere of a gas inert to the reaction, such as argon.

The reaction is usually carried out in a solvent. The solvent used in the reaction may include alcohols such as methanol, ethanol, and 2-propanol; ethers such as 1,4-dioxane, tetrahydrofuran, 1,2-dimethoxyethane, and methyl t-butyl ether; aliphatic hydrocarbons such as hexane and heptane; acid amides such as N,N-dimethylformamide; water; and mixtures thereof.

The transition metal compound used in the reaction may include palladium compounds, specific examples of which are palladium acetate, tetrakis(triphenylphosphine)palladium, {1,1'-bis(diphenylphosphino)ferrocene}-dichloropalladium(II)methylene chloride complex, and bis(triphenylphosphine)palladium (II) chloride. The amount of the transition metal compound used in the reaction, although it may be altered within the range to attain the purpose, is usually in the range of 0.01 to 0.1 mole, relative to 1 mole of the 4,6-dichloropyrimidine compound of formula (2).

The amount of the phenylboronic acid of formula $R_{4-4}B(OH)_2$ used in the reaction is usually in the range of 0.9 to 1.2 moles, relative to 1 mole of the 4,6-dichlorophenylphyrimidine compound of formula (2).

The reaction temperature is usually in the range of 0° C. to 80° C.

The reaction may also be carried out in the presence of a base and a phase transfer catalyst, if necessary. The base which can be used in the reaction may include inorganic bases such as barium hydroxide, potassium carbonate, sodium hydrogencarbonate, and tripotassium phosphate; and alkali metal salts such as sodium acetate and potassium acetate. The phase transfer catalyst may include quaternary ammonium salts such as tetrabutylammonium bromide and benzyltrimethyl ammonium bromide.

After completion of the reaction, the reaction mixture is subjected to the ordinary post-treatment including extraction with an organic solvent and concentration for isolation of the compounds of formula (11). The compounds of formula (11) thus isolated may be purified by chromatography or other techniques.

The phenylboronic acid compounds of formula $R^{4-4}B(OH)_2$ can be produced, for example, by reacting Grignard compounds such as $R^{4-4}MgBr$ or organic lithium compounds such as $R^{4-4}Li$ with boronic acid esters such as trimethoxyborane or triethoxyborane. The Grignard compounds of formula $R^{4-4}MgBr$ can be produced by reacting the corresponding halides, i.e., $R^{4-4}Br$ with magnesium. The organic lithium compounds of formula $R^{4-4}Li$ can be produced by reacting $R^{4-4}Br$ with n-butyl lithium.

Step (4-2)

The compounds of formula (12) can be produced by reacting the compounds of formula (11) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitriles such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (11).

The amount of the alcohol compound of formula $R^1OH$ used in the reaction is usually in the range of 1 to 1.2 moles, relative to 1 mole of the compound of formula (11).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (12). The compounds of formula (12) thus isolated may be purified by chromatography or other techniques.

Production Process 5

A production process for the present compounds wherein $R^4$ is a group of formula $NR^6R^7$; $R^6$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl; and $R^7$ is hydrogen, $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl.

The compounds of formula (15) can be produced from the 4,6-dichloropyrimidine compounds of formula (2) through step (5-1) and step (5-2) or through step (5-3) and step (5-4) according to the following scheme.

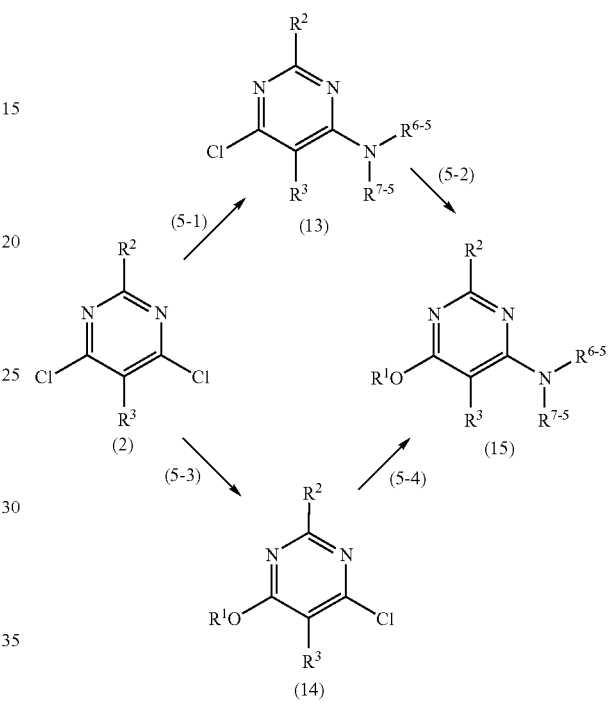

wherein $R^1$, $R^2$, and $R^3$ are as defined above; $R^{6-5}$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl; and $R^{7-5}$ is hydrogen, $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl.

Step (5-1)

The compounds of formula (13) can be produced by reacting the 4,6-dichloropyrimidine compounds of formula (2) with the amine compounds of formula $R^{6-5}R^{7-5}NH$ wherein $R^{6-5}$ and $R^{7-5}$ are as defined above.

The reaction is usually carried out in the presence or absence of a base in a solvent.

The solvent used in the reaction may include ethers such as tetrahydrofuran, diethyl ether, and methyl t-butyl ether; acid amides such as N,N-dimethylformamide; alcohols such as methanol and ethanol; and mixtures thereof.

The base used in the reaction may include inorganic bases such as sodium hydride; and organic bases such as triethylamine, and the base may suitable be selected depending upon the kind of solvent used in the reaction. When a base is used in the reaction, the amount of the base used in the reaction is usually in the range of 1 to 2.5 moles, relative to 1 mole of the 4,6-dichloropyrimidine compound of formula (2).

The amine of the amine compound of formula $R^{6-5}R^{7-5}NH$ used in the reaction is usually in the range of 1 to 1.2 moles, relative to 1 mole of the 4,6-dichloropyrimidine compound of formula (2).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (13). The compounds of formula (13) thus isolated may be purified by chromatography or other techniques.

Step (5-2)

The compounds of formula (15) can be produced by reacting the compounds of formula (13) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (13).

The amount of the alcohol compound of formula $R^1OH$ used in the reaction is usually in the range of 1 to 1.2 moles, relative to 1 mole of the compound of formula (13).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (15). The compounds of formula (15) thus isolated may be purified by chromatography or other techniques.

Step (5-3)

The compounds of formula (14) can be produced by reacting the 4,6-dichlroropyrimidine compounds of formula (2) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitriles such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the 4,6-dichloropyrimidine compound of formula (2).

The amount of the alcohol compound of formula $R^1OH$ used in the reaction is usually in the range of 1 to 1.2 moles, relative to 1 mole of the 4,6-dichloropyrimidine compound of formula (2).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (14). The compounds of formula (14) thus isolated may be purified by chromatography or other techniques.

Step (5-4)

The compounds of formula (15) can be produced by reacting the compounds of formula (14) with the amine compounds of formula $R^{6-5}R^{7-5}NH$ wherein $R^{6-5}$ and $R^{7-5}$ are as defined above.

The reaction is usually carried out in the presence or absence of a base in a solvent.

The solvent used in the reaction may include ethers such as tetrahydrofuran, diethyl ether, and methyl t-butyl ether; acid amides such as N,N-dimethylformamide; alcohols such as methanol and ethanol; and mixtures thereof.

The base used in the reaction may include inorganic bases such as sodium hydride; and organic bases such as triethylamine, and the base may suitable be selected depending upon the kind of solvent used in the reaction. When a base is used in the reaction, the amount of the base used in the reaction is usually in the range of 1 to 5 moles, relative to 1 mole of the compound of formula (14).

The amine of the amine compound of formula $R^{6-5}R^{7-5}NH$ used in the reaction is usually in the range of 1 to 4 moles, relative to 1 mole of the compound of formula (14).

The reaction temperature is usually in the range of 0° C. to 80° C.

The reaction time is usually in the range of 1 to 48 hours.

After completion of the reaction, the reaction mixture is treated, for example, by the following method for isolation of the desired product.

1) Method involving extraction of the reaction mixture with an organic solvent and the subsequent concentration; or 2) Method involving direct concentration of the reaction mixture without any treatment.

The compounds of formula (15) thus isolated may be purified by chromatography or other techniques.

Production Process 6

A production process for the present compounds wherein $R^4$ is a group of formula $NR^6R^7$; $R^6$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl; and $R^7$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, or optionally substituted $C_7$-$C_9$ aralkyl.

The compounds of formula (19) can be produced from the 4,6-dichloropyrimidine compounds of formula (2) according to the following scheme.

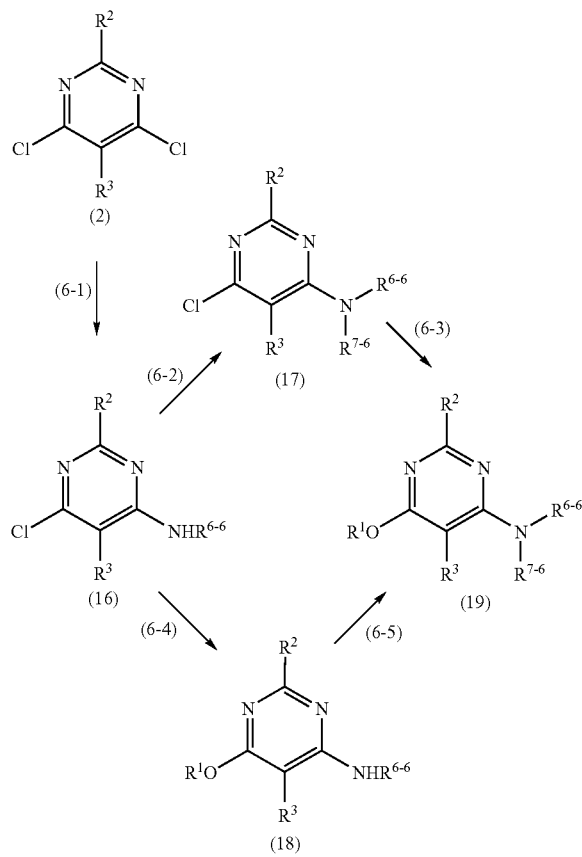

wherein $R^1$, $R^2$, and $R^3$ are as defined above; $R^{6-6}$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, optionally substituted phenyl, or optionally substituted $C_7$-$C_9$ aralkyl; and $R^{7-6}$ is $C_1$-$C_7$ alkyl, $C_1$-$C_3$ haloalkyl, $C_2$-$C_4$ (alkoxymethyl), $C_2$-$C_4$ (haloalkoxymethyl), $C_3$-$C_6$ alkenyl, $C_3$-$C_6$ haloalkenyl, $C_3$-$C_7$ alkynyl, cyanomethyl, or optionally substituted $C_7$-$C_9$ aralkyl.

Step (6-1)

The compounds of formula (16) can be produced by reacting the 4,6-dichloropyrimidine compounds of formula (2) with the amine compounds of formula $R^{6-6}NH_2$ wherein $R^{6-6}$ is as defined above.

The reaction is usually carried out in the presence or absence of a base in a solvent.

The solvent used in the reaction may include ethers such as tetrahydrofuran, diethyl ether, and methyl t-butyl ether; acid amides such as N,N-dimethylformamide; alcohols such as methanol and ethanol; and mixtures thereof.

The base used in the reaction may include inorganic bases such as sodium hydride; and organic bases such as triethylamine, and the base may suitable be selected depending upon the kind of solvent used in the reaction. When a base is used in the reaction, the amount of the base used in the reaction is usually in the range of 1 to 2 moles, relative to 1 mole of the 4,6-dichloropyrimidine compound of formula (2).

The amine compound of formula $R^{6-6}NH_2$ used in the reaction is usually in the range of 1 to 1.2 moles, relative to 1 mole of the 4,6-dichloropyrimidine compound of formula (2).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (16). The compounds of formula (16) thus isolated may be purified by chromatography or other techniques.

Step (6-2)

The compounds of formula (17) can be produced by reacting the compounds of formula (16) with the compounds of formula $R^{7-6}L$ wherein $R^{7-6}$ is as defined above and L is chlorine, bromine, iodine, methanesulfonyloxy, 4-toluenesulfonyloxy, or trifluoromethanesulfonyloxy in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium hydride and potassium hydride; and tertiary amines such as triethylamine and diisopropylethylamine. The amount of the base used in the reaction is usually in the range of 1 to 1.5 moles, relative to 1 mole of the compound of formula (16).

The amount of the compound of formula $R^{7-6}L$ used in the reaction is usually in the range of 1 to 1.2 moles, relative to 1 mole of the compound of formula (16).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (17). The compounds of formula (17) thus isolated may be purified by chromatography or other techniques.

Step (6-3)

The compounds of formula (19) can be produced by reacting the compounds of formula (17) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (17).

The amount of the alcohol compound of formula $R^1OH$ used in the reaction is usually in the range of 1 to 1.2 moles, relative to 1 mole of the compound of formula (17).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (19). The compounds of formula (19) thus isolated may be purified by chromatography or other techniques.

Step (6-4)

The compounds of formula (18) can be produced by reacting the compounds of formula (16) with the alcohol compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (16).

The amount of the alcohol compound of formula $R^1OH$ used in the reaction is usually in the range of 1 to 1.2 moles, relative to 1 mole of the compound of formula (16).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (18). The compounds of formula (18) thus isolated may be purified by chromatography or other techniques.

Step (6-5)

The compounds of formula (19) can be produced by reacting the compounds of formula (18) with the compounds of formula $R^{7-6}L$ wherein $R^{7-6}$ is as defined above and L is chlorine, bromine, iodine, methanesulfonyloxy, 4-toluenesulfonyloxy, or trifluoromethanesulfonyloxy in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitrites such as acetonitrile; dimethylsulfoxide; and mixtures thereof.

The base used in the reaction may include inorganic bases such as sodium hydride and potassium hydride. The amount of the base used in the reaction is usually in the range of 1 to 1.5 moles, relative to 1 mole of the compound of formula (18).

The amount of the compound of formula $R^{7-6}L$ used in the reaction is usually in the range of 1 to 1.2 moles, relative to 1 mole of the compound of formula (18).

The reaction temperature is usually in the range of 0° C. to 80° C.

The reaction time is usually in the range of 1 to 12 hours. After completion of the reaction, the reaction mixture is subjected to the ordinary post-treatment including extraction with an organic solvent and concentration for isolation of the compounds of formula (18). The compounds of formula (18) thus isolated may be purified by chromatography or other techniques.

Production Process 7

A production process for the present compounds wherein $R^4$ is optionally substituted $C_7$-$C_9$ aralkyl.

The compounds for formula (21) can be produced from the 4,6-dichloropyrimidine compounds of formula (2) through step (7-1) and step (7-2) according to the following scheme.

wherein $R^1$, $R^2$, and $R^3$ are as defined above and $R^{4-7}$ is optionally substituted $C_7$-$C_9$ aralkyl.

Step (7-1)

The compounds of formula (20) can be produced by reacting the 4,6-dichloropyrimidine compounds of formula (2) with zinc compounds of formula $R^{4-7}ZnX$ wherein X is chlorine, bromine, or iodine in the presence of a transition metal compound.

The reaction is usually carried out in a solvent. The solvent used in the reaction may include ethers such as tetrahydrofuran and diethyl ether; acid amides such as N,N-dimethylformamide; nitrites such as acetonitrile; and mixtures thereof.

The transition metal compound used in the reaction may include palladium compounds, specific examples of which are tetrakis(triphenylphosphine)palladium and bis(triphenylphosphine)palladium chloride. The amount of the transition metal compound used in the reaction is usually in the range of 0.01 to 0.1 mole, relative to 1 mole of the 4,6-dichloropyrimidine compound of formula (2).

The amount of the zinc compound of formula $R^{4-7}ZnX$ used in the reaction is usually in the range of 1 to 1.2 moles, relative to 1 mole of the 4,6-dichlorophenylphyrimidine compound of formula (2).

The reaction temperature is usually in the range of 0° C. to 100° C. (or the boiling point of a solvent used in the reaction, when it is 80° C. or lower).

After completion of the reaction, the reaction mixture is subjected to the ordinary post-treatment including extraction with an organic solvent and concentration for isolation of the compounds of formula (20). The compounds of formula (20) thus isolated may be purified by chromatography or other techniques.

The zinc compounds of formula $R^{4-7}ZnX$ are usually formed in the system from the compounds of formula $R^{4-7}X$, zinc, trimethylsilane chloride, and dibromomethane, and they are used in the reaction.

Step (7-2)

The compounds of formula (21) can be produced by reacting the compounds of formula (20) with the compounds of formula $R^1OH$ wherein $R^1$ is as defined above in the presence of a base.

The reaction is usually carried out in a solvent. The solvent used in the reaction may include ethers such as tetrahydrofuran, diethyl ether, and methyl t-butyl ether; acid amides such as N,N-dimethylformamide; nitriles such as acetonitrile; dimethylsulfoxide; and mixtures thereof.

The base used in the reaction may include inorganic bases such as sodium hydride. The amount of the base used in the reaction is usually in the range of 1 to 1.5 moles, relative to 1 mole of the compound of formula (20).

The amount of the alcohol compound of formula $R^1OH$ used in the reaction is usually in the range of 1 to 1.2 moles, relative to 1 mole of the compound of formula (20).

The reaction temperature is usually in the range of 0° C. to 80° C.

The reaction time is usually in the range of 0.5 to 12 hours.

After completion of the reaction, the reaction mixture is subjected to the ordinary post-treatment including extraction with an organic solvent and concentration for isolation of the compounds of formula (21). The compounds of formula (21) thus isolated may be purified by chromatography or other techniques.

Production Process 8

A production process for the present compounds wherein $R^4$ is a group of formula —(C=O)—$R^{5-8}$ and $R^{5-8}$ is optionally substituted phenyl as well as for the present compounds wherein $R^4$ is a group of formula —(C=NOR$^{8-8}$)—$R^{5-8}$; $R^{5-8}$ is optionally substituted phenyl; and $R^{18}$ is $C_1$-$C_4$ alkyl.

The compounds of formula (23) can be produced from the compounds of formula (3) through step (8-1) and step (8-2) according to the following scheme, and the compounds of formula (24) can further be produced through step (8-3).

The base used in the reaction may include inorganic bases such as sodium hydride and potassium hydride; lithium amides such as lithium diisopropylamide; alkali metal carbonates such as potassium carbonate and sodium carbonate; and alkali metal alkoxides such as potassium t-butoxide. The amount of the base used in the reaction is usually in the range of 1 to 2 moles, relative to 1 mole of the compound of formula (3).

The amount of the nitrile compound of formula $R^{5-8}CH_2CN$ used in the reaction is usually in the range of 1 to 1.2 moles, relative to 1 mole of the compound of formula (3).

The reaction temperature is usually in the range of 0° C. to 80° C.

The reaction time is usually in the range of 1 to 12 hours.

After completion of the reaction, the reaction mixture is subjected to the ordinary post-treatment including extraction with an organic solvent and concentration for isolation of the compounds of formula (22). The compounds of formula (22) thus isolated may be purified by chromatography or other techniques.

Step (8-2)

The compounds of formula (23) can be produced by oxidation reaction of the compounds of formula (22) with an oxygen gas in the presence of a base.

The oxidation reaction is usually carried out in a solvent. The solvent used in the reaction may include ethers such as tetrahydrofuran and diethyl ether.

The base used in the reaction may include alkali metal hydrides such as sodium hydride and potassium hydride;

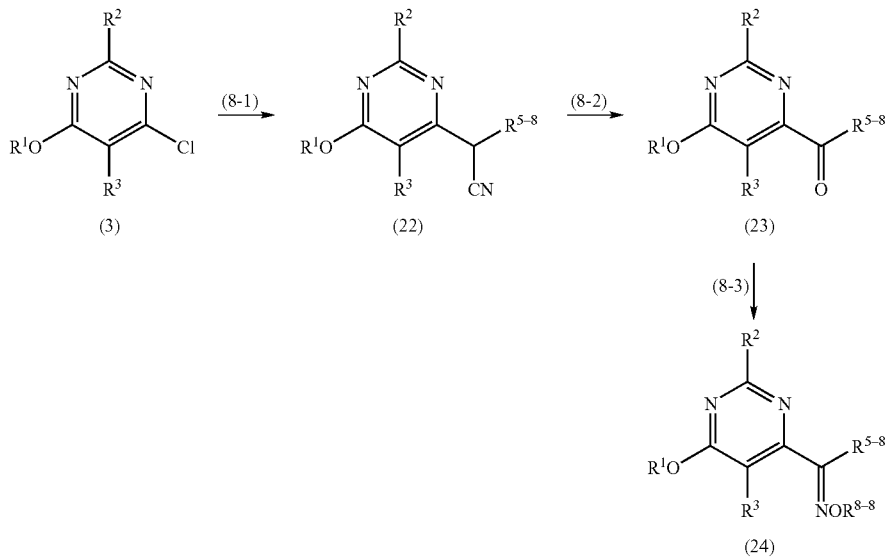

wherein $R^1$, $R^2$, and $R^3$ are as defined above; $R^{5-8}$ is optionally substituted phenyl; and $R^{8-8}$ is $C_1$-$C_4$ alkyl.

Step (8-1)

The compounds of formula (22) can be produced by reacting the compounds of formula (3) with the nitrile compounds of formula $R^{5-8}CH_2CN$ wherein $R^{5-8}$ is as defined above in the presence of a base.

The reaction is usually carried out in a solvent. The solvent used in the reaction may include ethers such as tetrahydrofuran, diethyl ether, and methyl t-butyl ether.

alkali metal carbonates such as potassium carbonate; and alkali metal alkoxides such as potassium t-butoxide. The amount of the base used in the reaction is usually in the range of 1 to 2 moles, relative to 1 mole of the compound of formula (22).

The reaction temperature is usually in the range of 0° C. to 80° C.

The reaction time is usually in the range of 12 to 48 hours.

After completion of the reaction, the reaction mixture is subjected to the ordinary post-treatment including extraction with an organic solvent and concentration for isolation of the compounds of formula (23). The compounds of formula (23) thus isolated may be purified by chromatography or other techniques.

Step (8-3)

The compounds of formula (24) can be produced by reacting the compounds of formula (23) with the hydroxylamine compounds of formula $R^{8-8}O\text{—}NH_2$ wherein $R^{6-8}$ is as defined above or salts thereof.

The reaction is usually carried out in a solvent or without any solvent, and if necessary, in the presence of a base. The solvent used in the reaction may include alcohols such as ethanol, ethers such as tetrahydrofuran, diethyl ether, and methyl t-butyl ether; pyridine; water; and mixtures thereof.

The base used in the reaction may include tertiary amines such as triethylamine; nitrogen-containing aromatic compounds such as pyridine; and carboxylic acid alkali metal salts such as sodium acetate. When a base is used in the reaction, the amount of the base is usually 1 mole to excess, relative to 1 mole of the compound of formula (23).

The amount of the compound of formula $R^{8-8}ONH_2$ used in the reaction is usually in the range of 1 to 1.2 moles, relative to 1 mole of the compound of formula (23).

The reaction temperature is usually in the range of 0° C. to 150° C.

The reaction time is usually in the range of 1 to 12 hours.

After completion of the reaction, the reaction mixture is subjected to the ordinary post-treatment including extraction with an organic solvent and concentration for isolation of the compounds of formula (24). The compounds of formula (24) thus isolated may be purified by chromatography or other techniques.

The pests against which the present compounds have an effect may include arthropods (e.g., insects, acarines) and nemathelminthes, specific examples of which are as follows:

Hemiptera:

Delphacidae such as *Laodelphax striatellus*, *Nilaparvata lugens*, and *Sogatella furcifera*, Deltocephalidae such as *Nephotettix cincticeps* and *Empoasca onukii*, Aphididae such as *Aphis gossypii* and *Myzus persicae*, Pentatomidae, Aleyrodidae such as *Trialeurodes vaporariorum*, *Bemisia tabaci*, and *Bemisia argentifolii*, Coccidae, Tingidae, Psyllidae, etc.

Lepidoptera:

Pyralidae such as *Chilo suppressalis*, *Cnaphalocrocis medinalis*, *Ostrinia nubilalis*, and *Parapediasia teterrella*, Noctuidae such as *Spodoptera litura*, *Spodoptera exigua*, *Pseudaletia separata*, *Mamestra brassicae*, *Agrotis ipsilon*, *Trichoplusia* spp., *Heliothis* spp., *Helicoverpa* spp., and *Earias* spp., Pieridae such as *Pieris rapae crucivora*, Tortricidae such as *Adoxophyes orana fasciata*, *Grapholita molesta*, and *Cydia pomonella*, Carposinidae such as *Carposina niponensis*, Lyonetiidae such as *Lyonetia clerkella*, Gracllariidae such as *Phyllonorycter ringoniella*, Phyllocnistidae such as *Phyllocnistis citrella*, Yponomeutidae such as *Plutella xylostella*, Gelechiidae such as *Pectinophora gossypiella*, Arctiidae, Tineidae, etc.

Diptera:

Calicidae such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Anthomyiidae, Cecidomyiidae such as *Delia platura* and *Delia antiqua*, Tephritidae, Drosophilidae, Psychodidae, Tabanidae, Simuliidae, Stomoxyidae, Agromyzidae, etc.

Coleoptera:

*Diabrotica* spp. such as *Diabrotica virgifera virgifera* and *Diabrotica undecimpunctata howardi*; Scarabaeidae such as *Anomala cuprea* and *Anomala rufocuprea*, Curculionidae such as *Sitophilus zeamais*, *Lissorhoptrus oryzophilus*, and *Callosobruchuys chienensis*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Anobiidae, *Epilachna* spp. such as *Epilachna vigintioctopunctata*, Lyctidae, Bostrychidae, Cerambycidae, *Paederus fuscipes*, etc.

Thysanoptera:

Thripidae such as *Thrips* spp., e.g., *Thrips palmi*, *Frankliniella* spp., e.g., *Frankliniella occidentalis*, and *Sciltothrips* spp., e.g., *Sciltothrips dorsalis*, and Phlaeotheripidae, etc.

Hymenoptera:

Tenthredinidae, Formicidae, Vespidae, etc.

Dictyoptera:

Blattidae, Blattellidae, etc.

Orthoptera:

Acrididae, Gryllotalpidae, etc.

Aphaniptera:

*Purex irritans* etc.

Anoplura:

*Pediculus humanus capitis* etc.

Isoptera:

Termitidae etc.

Acarina:

Tetranychidae such as *Tetranychus urticae*, *Tetranychus kanzawai*, *Panonychus citri*, *Panonychus ulmi*, and *Oligonychus*, Eriophyidae such as *Aculops pelekassi* and *Aculus schlechtendali*, Tarsonemidae such as *Polyphagotarsonemus latus*, Tenuipalpidae, Tuckerellidae, Ixodidae such as *Haemaphysalis longicornis*, *Haemaphysalis flava*, *Dermacentor taiwanicus*, *Ixodes ovatus*, *Ixodes persulcatus*, and *Boophilus microplus*, Acaridae such as *Tyrophagus putrescentiae*, Epidermoptidae such as *Dermatophagoides farinae* and *Dermatophagoides ptrenyssnus*, Cheyletidae such as *Cheyletus eruditus* and *Cheyletus malaccensis*, *Dermanyssus* spp., etc.

Nematodes:

*Pratylenchus coffeae*, *Pratylenchus fallax*, *Heterodera glycines*, *Globadera rostochiensis*, *Meloidogyne hapla*, *Meloidogyne incognita*, etc.

When the present compounds are used as pesticides, they may be used as such; however, they are usually used after formulation into oil sprays, emulsifiable concentrates, flowables, granules, dusts, poison baits, microcapsules, or application forms by mixing with solid carriers, liquid carriers, gaseous carriers, or baits, and if necessary, by addition of surfactants or other auxiliaries and processing.

These formulations may usually contain the present compounds in 0.01% to 95% by weight.

The solid carrier used in the formulation may include fine powder or granules of clay materials such as kaolin clay, diatomaceous earth, synthetic hydrated silicon oxide, bentonite, Fubasami clay, and acid clay; various kinds of talc, ceramics, and other inorganic minerals such as sericite, quartz, sulfur, activated charcoal, calcium carbonate, and hydrated silica; and chemical fertilizers such as ammonium sulfate, ammonium phosphate, ammonium nitrate, urea, and ammonium chloride.

The liquid carrier may include water; alcohols such as methanol and ethanol; ketones such as acetone and methyl ethyl ketone; aromatic hydrocarbons such as benzene, toluene, xylene, ethylbenzene, and methylnaphthalene; aliphatic hydrocarbons such as hexane, cyclohexane, kerosene, and light oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane, and carbon tetrachloride; dimethyl sulfoxide; and vegetable oils such as soybean oil and cottonseed oil.

The gaseous carrier or propellant may include Freon gas, butane gas, LPG (liquefied petroleum gas), dimethyl ether, and carbon dioxide.

The surfactant may include alkyl sulfates, alkyl sulfonates, alkyl arylsulfonates, alkyl aryl ethers and their polyoxyethylene derivatives, polyethylene glycol ethers, polyhydric alcohol esters, and sugar alcohol derivatives.

The auxiliaries may include fixing agents, dispersing agents, and stabilizers, specific examples of which are casein, gelatin, polysaccharides such as starch, gum arabic, cellulose derivatives, and alginic acid; lignin derivatives, bentonite, sugars, synthetic water-soluble polymers such as polyvinyl alcohol, polyvinyl pyrrolidone, and polyacrylic acid; PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, and fatty acids and their esters.

The base material for poison baits may include bait materials such as grain powder, vegetable oils, sugars, and crystalline cellulose; antioxidants such as dibutylhydroxytoluene and nordihydroguaiaretic acid; preservatives such as dehydroacetic acid; substances for preventing erroneous eating, such as red pepper powder; pest attractant flavors such as cheese flavor, onion flavor, and peanut oil.

When the present compounds are used as pesticides, their application amounts are usually 0.1 to 1000 g in amounts of the present compounds per 1000 m². For emulsifiable concentrates, wettable powders, flowables, or microcapsules, these formulations are usually applied after water dilution so that the concentrations of active ingredients come to 10 to 10000 ppm, and for granules or dusts, these formulations are usually applied as such.

These formulations or their water dilutions may be used in the foliar treatment of plants such as crop plants to be protected against pests, or may be applied to the nursery beds before planting of crop plant seedlings or to the planting holes or the bases of plants at the time of planting. For the purpose of controlling pests inhabiting the soil of a cultivated land, they may be applied to the soil. In addition, resin formulations processed into a sheet, string or other shapes may be applied by directly winding around crop plants, extending in the neighborhood of crop plants, or laying on the soil surface at the bases of plants.

Furthermore, they may be used in admixture with or separately but simultaneously with other insecticides, nematocides, acaricides, bactericides, fungicides, herbicides, plant growth regulators, synergists, fertilizers, soil conditioners and/or animal feeds.

The insecticide and/or nematocide and/or acaricide which can be used may include organophosphorus compounds such as Fenitrothion, Fenthion, Pyridaphenthion, Diazinon, Chlorpyriphos, Chlorpyriphos-methyl, Acephate, Methidathion, Disulfoton, DDVP, Sulprofos, Profenofos, Cyanophos, Dioxabenzofos, Dimethoate, Phenthoate, Malathion, Trichlorfon, Azinphos-methyl, Monocrotophos, Dicrotophos, Ethion and Fosthiazate; carbamate compounds such as BPMC, Benfuracarb, Propoxur, Carbosulfan, Carbaryl, Methomyl, Ethiofencarb, Aldicarb, Oxamyl, Fenothiocarb, Thiodicarb, and Alanycarb; pyrethroid compounds such as Etofenprox, Fenvalerate, Esfenvalerate, Fenpropathrin, Cypermethrin, α-Cypermethrin, Z-Cypermethrin, Permethrin, Cyhalothrin, λ-Cyhalothrin, Cyfluthrin, β-Cyfluthrin, Deltamethrin, Cycloprothrin, τ-Fluvalinate, Flucythrinate, Bifenthrin, Acrinathrin, Tralomethrin, Silafluofen, and Halfenprox; neonicotinoid compounds such as Acetamiprid, Clothianidin, Nitenpyram, Thiamethoxam, Dinotefuran, Imidacloprid, and Thiacloprid; benzoylphenylurea compounds such as Chlorfluazuron, Teflubenzuron, Fulfenoxuron, and Lufenuron; benzoylhydrazide compounds such as Tebufenozide, Halofenozide, Methoxyfenozide, and Chromafenozide; thiadiazine derivatives such as Buprofezin; Nereistoxin derivatives such as Cartap, Thiocyclam, and Bensultap; chlorinated hydrocarbon compounds such as Endosulfan, γ-BHC, and 1,1-bis(chlorophenyl)-2,2,2-trichloroethanol; formamidine derivatives such as Amitraz and Chlordimeform; thiourea derivatives such as Diafenthiuron; phenylpyrazole compounds; Chlorfenapyr, Pymetrozine, Spinosad, Indoxacarb, Pyridalyl, Pyriproxyfen, Fenoxycarb, Diofenolan, Cyromazine, Bromopropylate, Tetradifon, Quinomethionate, Propargate, Fenbutatin oxide, Hexythiazox, Etoxazole, Chlofentezine, Pyridaben, Fenpyroximate, Tebfenpyrad, Pyrimidifen, Fenazaquin, Acequinocyl, Bifenazate, Fluacrypyrim, Spirodiclofen, Milbemectin, Avermectin, Emamectin benzoate, Azadilactin [AZAD], and polynactin complexes [e.g., tetranactin, dinactin, trinactin].

The present invention will hereinafter be further illustrated by many production examples, formulation examples, and test examples; however, the present invention is not limited to these examples.

In the production examples and reference production examples, $^1$H-NMR shows, unless otherwise indicated, data measured using tetramethylsilane as an internal standard in a deuterated chloroform solvent.

In the production examples, the present compound numbers stand for the numbers shown in Tables 124 to 129.

First, the production examples for the present compounds will be described below.

PRODUCTION EXAMPLE 1

In 4 ml of tetrahydrofuran was suspended 0.27 g of sodium hydride (60% in oil), to which 0.7 ml of a tetrahydrofuran solution containing 0.41 g of 2-butyn-1-ol was slowly added dropwise with stirring at room temperature. The mixture was then stirred at room temperature for 20 minutes, to which 0.7 ml of a tetrahydrofuran solution containing 0.4 g of 4,6-dichloropyrimidine was slowly added dropwise. After completion of the dropwise addition, the mixture was stirred at room temperature for 40 minutes. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.39 g of 4,6-bis(2-butynyloxy)pyrimidine (the present compound (1)), m.p.: 82.9° C.

PRODUCTION EXAMPLE 2

In 4 ml of tetrahydrofuran was suspended 0.12 g of sodium hydride (60% in oil), to which 0.7 ml of a tetrahydrofuran solution containing 0.18 g of 2-butyn-1-ol was slowly added dropwise with stirring at room temperature. The mixture was stirred at room temperature for 20 minutes and then cooled to 0° C., to which 0.7 ml of a tetrahydrofuran solution containing 0.4 g of 4-chloro-6-(2-propynyloxy)pyrimidine was slowly added dropwise. The mixture was further stirred at 0° C. for 4.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.9 g of 4-(2-butynyloxy)-6-(2-propynyloxy)pyrimidine (the present compound (2)).

$^1$H-NMR: 1.87 (t, 3H), 2.54 (t, 1H), 4.95 (q, 2H), 5.00 (d, 2H), 6.19 (s, 1H), 8.48 (s, 1H)

PRODUCTION EXAMPLE 3

In 5 ml of tetrahydrofuran was suspended 0.34 g of sodium hydride (60% in oil), to which 0.9 ml of a tetrahydrofuran solution containing 0.62 g of 2-pentyn-1-ol was slowly added dropwise with stirring at room temperature. The mixture was then stirred at room temperature for 20 minutes, to which 0.9 ml of a tetrahydrofuran solution containing 0.5 g of 4,6-dichloropyrimidine was slowly added dropwise. After completion of the dropwise addition, the mixture was stirred at room temperature for 40 minutes. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.81 g of 4,6-bis(2-pentynyloxy)pyrimidine (the present compound (3)).

$^1$H-NMR: 1.15 (t, 6H), 2.16-2.35 (m, 4H), 4.97 (t, 4H), 6.18 (s, 1H), 8.46 (s, 1H)

PRODUCTION EXAMPLE 4

In 14 ml of tetrahydrofuran was suspended 0.57 g of sodium hydride (60% in oil), to which 2.5 ml of a tetrahydrofuran solution containing 0.8 g of 2-pentyn-1-ol was slowly added dropwise with stirring at room temperature. The mixture was stirred at room temperature for 20 minutes and then cooled to 0° C., to which 2.5 ml of a tetrahydrofuran solution containing 1.6 g of 4-chloro-6-(2-propynyloxy)pyrimidine was slowly added dropwise. The mixture was further stirred at 0° C. for 3.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.98 g of 4-(2-pentynyloxy)-6-(2-propynyloxy)pyrimidine (the present compound (5)).

$^1$H-NMR: 1.15 (t, 3H), 2.04-2.29 (m, 2H), 2.53 (t, 1H), 4.97-5.01 (m, 4H), 6.19 (s, 1H), 8.47 (s, 1H)

PRODUCTION EXAMPLE 5

In 2 ml of tetrahydrofuran was suspended 0.1 g of sodium hydride (60% in oil), to which 0.6 ml of a tetrahydrofuran solution containing 0.15 g of 2-pentyn-1-ol was slowly added dropwise with stirring at room temperature. The mixture was stirred at room temperature for 20 minutes and then cooled to 0° C., to which 0.6 ml of a tetrahydrofuran solution containing 0.3 g of 4-chloro-6-(2-butynyloxy)pyrimidine was slowly added dropwise. The mixture was further stirred at 0° C. for 3.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.33 g of 4-(2-butynyloxy)-6-(2-pentynyloxy)pyrimidine (the present compound (6)), m.p.: 67.4° C.

PRODUCTION EXAMPLE 6

In 2 ml of tetrahydrofuran was suspended 0.1 g of sodium hydride (60% in oil), to which 0.6 ml of a tetrahydrofuran solution containing 0.2 g of 4,4-dimethyl-2-pentyn-1-ol was slowly added dropwise with stirring at room temperature. The mixture was stirred at room temperature for 20 minutes and then cooled to 0° C., to which 0.6 ml of a tetrahydrofuran solution containing 0.3 g of 4-chloro-6-(2-butynyloxy)pyrimidine was slowly added dropwise. The mixture was further stirred at 0° C. for 3.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.15 g of 4-(2-butynyloxy)-6-(4,4-dimethyl-2-pentynyloxy)pyrimidine (the present compound (7)) and 0.074 g of 4,6-bis(4,4-dimethyl-2-pentynyloxy)pyrimidine (the present compound (8)).

The melting point of 4-(2-butynyloxy)-6-(4,4-dimethyl-2-pentynyloxy)pyrimidine: 113° C.

The melting point of 4,6-bis(4,4-dimethyl-2-pentynyloxy)pyrimidine: 83.5° C.

PRODUCTION EXAMPLE 7

To 2 ml of N,N-dimethylformamide were added 0.2 g of 4-chloro-6-(2-butynyloxy)pyrimidine, 0.38 g of potassium carbonate, and 0.1 g of phenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water. The organic layer was dried over anhydrous magnesium sulfate and concentrated. The residue was subjected to silica gel column chromatography to give 0.16 g of 4-(2-butynyloxy)-6-phenoxypyrimidine (the present compound (9)).

$^1$H-NMR: 1.86 (t, 3H), 4.97 (q, 2H), 6.17 (s, 1H), 7.14 (d, 2H), 7.25 (t, 1H), 7.42 (t, 2H), 8.47 (s, 1H)

PRODUCTION EXAMPLE 8

In 2 ml of tetrahydrofuran was suspended 0.1 g of sodium hydride (60% in oil), to which 0.6 ml of a tetrahydrofuran solution containing 0.12 g of 3-butyn-2-ol was slowly added dropwise with stirring at room temperature. The mixture was stirred at room temperature for 20 minutes and then cooled to 0° C., to which 0.6 ml of a tetrahydrofuran solution containing 0.4 g of 4-chloro-6-(2-propynyloxy)pyrimidine was slowly added dropwise. The mixture was further stirred at 0° C. for 4.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.14 g of 4-(1-methyl-2-propynyloxy)-6-(2-propynyloxy)pyrimidine (the present compound (11)).

$^1$H-NMR: 1.63 (d, 3H), 2.47 (d, 1H), 2.51 (t, 1H), 5.00 (d, 2H), 5.72-5.81 (m, 1H), 6.17 (s, 1H), 8.49 (s, 1H)

PRODUCTION EXAMPLE 9

In 2 ml of tetrahydrofuran was suspended 0.1 g of sodium hydride (60% in oil), to which 0.6 ml of a tetrahydrofuran solution containing 0.13 g of 3-butyn-1-ol was slowly added dropwise with stirring at room temperature. The mixture was stirred at room temperature for 20 minutes and then cooled to 0° C., to which 0.6 ml of a tetrahydrofuran solution containing 0.3 g of 4-chloro-6-(2-propynyloxy)pyrimidine was slowly added dropwise. The mixture was further stirred at 0° C. for 4.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.14 g of 4-(3-butynyloxy)-6-(2-propynyloxy)pyrimidine (the present compound (12)).

$^1$H-NMR: 2.02 (t, 1H), 2.50 (t, 1H), 2.64-2.70 (m, 2H), 4.46 (t, 2H), 5.00 (d, 2H), 6.15 (s, 1H), 8.44 (s, 1H)

PRODUCTION EXAMPLE 10

In 4 ml of tetrahydrofuran was suspended 0.13 g of sodium hydride (60% in oil), to which 0.7 ml of a tetrahydrofuran solution containing 0.12 g of 2-propyn-1-ol was slowly added dropwise with stirring at room temperature. The mixture was stirred at room temperature for 20 minutes and then cooled to 0° C., to which 0.7 ml of a tetrahydrofuran solution containing 0.4 g of 4-chloro-6-benzyloxypyrimidine was slowly added dropwise. The mixture was further stirred at 0° C. for 4.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.17 g of 4-benzyloxy-6-(2-propynyloxy)pyrimidine (the present compound (13)).

$^1$H-NMR: 2.49 (t, 1H), 4.96 (d, 2H), 5.38 (s, 2H), 6.17 (s, 1H), 7.30-7.41 (m, 5H), 8.46 (s, 1H)

PRODUCTION EXAMPLE 11

To 5 ml of N,N-dimethylformamide were added 0.2 g of 4-chloro-6-(2-propynyloxy)pyrimidine, 0.23 g of potassium carbonate and 0.4 g of 4-chlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.1 g of 4-(4-chlorophenoxy)-6-(2-propynyloxy)pyrimidine (the present compound (14)), m.p.: 100.3° C.

PRODUCTION EXAMPLE 12

To 5 ml of N,N-dimethylformamide were added 0.19 g of 4-chloro-6-(2-propynyloxy)pyrimidine, 0.22 g of potassium carbonate, and 0.13 g of 3-chlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(3-chlorophenoxy)-6-(2-propynyloxy)pyrimidine (the present compound (15)), m.p.: 71.6° C.

PRODUCTION EXAMPLE 13

To 5 ml of N,N-dimethylformamide were added 0.3 g of 4-chloro-6-(2-butynyloxy)pyrimidine, 0.34 g of potassium carbonate, and 0.24 g of 2-chloro-4-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.53 g of 4-(2-chloro-4-fluorophenoxy)-6-(2-butynyloxy)pyrimidine (the present compound (16)).

$^1$H-NMR: 1.87 (t, 3H), 4.98 (q, 2H), 6.28 (s, 1H), 7.00-7.23 (m, 3H), 8.41 (s, 1H)

PRODUCTION EXAMPLE 14

To 5 ml of N,N-dimethylformamide were added 0.2 g of 4-chloro-6-(2-propynyloxy)pyrimidine, 0.25 g of potassium carbonate, and 0.19 g of 3-trifluoromethylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(3-trifluoromethylphenoxy)-6-(2-propynyloxy)pyrimidine (the present compound (17)).

$^1$H-NMR: 2.52 (t, 1H), 5.04 (d, 2H), 6.30 (s, 1H), 7.28-7.54 (m, 4H), 8.47 (s, 1H)

PRODUCTION EXAMPLE 15

To 5 ml of N,N-dimethylformamide were added 0.2 g of 4-chloro-6-(2-propynyloxy)pyrimidine, 0.25 g of potassium carbonate, and 0.19 g of 2-trifluoromethylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.14 g of 4-(2-trifluoromethylphenoxy)-6-(2-propynyloxy)pyrimidine (the present compound (18)).

$^1$H-NMR: 2.54 (t, 1H), 5.04 (d, 2H), 6.35 (s, 1H), 7.24 (d, 1H), 7.34 (t, 1H), 7.61 (t, 1H), 7.72 (d, 1H), 8.45 (s, 1H)

PRODUCTION EXAMPLE 16

To 5 ml of N,N-dimethylformamide were added 0.2 g of 4-chloro-6-(2-propynyloxy)pyrimidine, 0.25 g of potassium carbonate, and 0.15 g of 2-chlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.14 g of 4-(2-chlorophenoxy)-6-(2-propynyloxy)pyrimidine (the present compound (19)), m.p.: 76.2° C.

PRODUCTION EXAMPLE 17

To 5 ml of N,N-dimethylformamide were added 0.2 g of 4-chloro-6-(2-propynyloxy)pyrimidine, 0.25 g of potassium carbonate, and 0.19 g of 4-trifluoromethylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.21 g of 4-(4-trifluoromethylphenoxy)-6-(2-propynyloxy)pyrimidine (the present compound (20)).

$^1$H-NMR: 2.53 (t, 1H), 5.04 (d, 2H), 6.32 (s, 1H), 7.26 (d, 2H), 7.78 (d, 2H), 8.47 (s, 1H)

PRODUCTION EXAMPLE 18

To 5 ml of N,N-dimethylformamide were added 0.43 g of 4-chloro-6-(2-propynyloxy)pyrimidine, 0.52 g of potassium carbonate, and 0.4 g of 2,6-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.53 g of 4-(2,6-difluorophenoxy)-6-(2-propynyloxy)pyrimidine (the present compound (21)), m.p.: 67.2° C.

PRODUCTION EXAMPLE 19

To 5 ml of N,N-dimethylformamide were added 0.2 g of 4-chloro-6-(2-propynyloxy)pyrimidine, 0.25 g of potassium carbonate, and 0.21 g of 2,4-dichlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.24 g of 4-(2,4-dichlorophenoxy)-6-(2-propynyloxy)pyrimidine (the present compound (22)), m.p.: 106.7° C.

PRODUCTION EXAMPLE 20

To 5 ml of N,N-dimethylformamide were added 0.2 g of 4-chloro-6-(2-propynyloxy)pyrimidine, 0.25 g of potassium carbonate, and 0.21 g of 3,4-dichlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.14 g of 4-(3,4-dichlorophenoxy)-6-(2-propynyloxy)pyrimidine (the present compound (23)), m.p.: 109.2° C.

PRODUCTION EXAMPLE 21

To 5 ml of N,N-dimethylformamide were added 0.2 g of 4-chloro-6-(2-propynyloxy)pyrimidine, 0.25 g of potassium carbonate, and 0.21 g of 3,5-dichlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.24 g of 4-(3,5-dichlorophenoxy)-6-(2-propynyloxy)pyrimidine (the present compound (24)), m.p.: 136.5° C.

PRODUCTION EXAMPLE 22

To 5 ml of N,N-dimethylformamide were added 0.2 g of 4-chloro-6-(2-propynyloxy)pyrimidine, 0.25 g of potassium carbonate, and 0.21 g of 2,5-dichlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.19 g of 4-(2,5-dichlorophenoxy)-6-(2-propynyloxy)pyrimidine (the present compound (25)), m.p.: 87.7° C.

PRODUCTION EXAMPLE 23

To 5 ml of N,N-dimethylformamide were added 0.2 g of 4-chloro-6-(2-propynyloxy)pyrimidine, 0.25 g of potassium carbonate, and 0.21 g of 2,3-dichlorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.25 g of 4-(2,3-dichlorophenoxy)-6-(2-propynyloxy)pyrimidine (the present compound (26)), m.p.: 91.9° C.

PRODUCTION EXAMPLE 24

To 5 ml of N,N-dimethylformamide were added 0.2 g of 4-chloro-6-(2-propynyloxy)pyrimidine, 0.25 g of potassium carbonate, and 0.14 g of 2-methylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.15 g of 4-(2-methylphenoxy)-6-(2-propynyloxy)pyrimidine (the present compound (27)), m.p.: 64.8° C.

PRODUCTION EXAMPLE 25

To 5 ml of N,N-dimethylformamide were added 0.2 g of 4-chloro-6-(2-propynyloxy)pyrimidine, 0.25 g of potassium carbonate, and 0.14 g of 4-methylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.28 g of 4-(4-methylphenoxy)-6-(2-propynyloxy)pyrimidine (the present compound (28)).

$^1$H-NMR: 2.37 (s, 3H), 2.51 (t, 1H), 5.00 (d, 2H), 6.18 (s, 1H), 7.01 (d, 2H), 7.21 (d, 2H), 8.47 (s, 1H)

PRODUCTION EXAMPLE 26

To 5 ml of N,N-dimethylformamide were added 0.2 g of 4-chloro-6-(2-propynyloxy)pyrimidine, 0.25 g of potassium carbonate, and 0.14 g of 3-methylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.27 g of 4-(3-methylphenoxy)-6-(2-propynyloxy)pyrimidine (the present compound (29)).

$^1$H-NMR: 2.36 (s, 3H), 2.52 (t, 1H), 5.01 (d, 2H), 6.17 (s, 1H), 6.93-6.94 (m, 2H), 7.07 (d, 1H), 7.29 (t, 1H), 8.47 (s, 1H)

PRODUCTION EXAMPLE 27

To 5 ml of N,N-dimethylformamide were added 0.2 g of 4-chloro-6-(2-propynyloxy)pyrimidine, 0.25 g of potassium carbonate, and 0.18 g of 3-methoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.23 g of 4-(3-methoxyphenoxy)-6-(2-propynyloxy)pyrimidine (the present compound (30)).

$^1$H-NMR: 2.51 (t, 1H), 3.80 (s, 3H), 5.02 (d, 2H), 6.19 (s, 1H), 6.67-6.83 (m, 3H), 7.32 (t, 1H), 8.49 (s, 1H)

PRODUCTION EXAMPLE 28

To 5 ml of N,N-dimethylformamide were added 0.2 g of 4-chloro-6-(2-propynyloxy)pyrimidine, 0.25 g of potassium carbonate, and 0.18 g of 4-methoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.14 g of 4-(4-methoxyphenoxy)-6-(2-propynyloxy)pyrimidine (the present compound (31)), m.p.: 72.0° C.

PRODUCTION EXAMPLE 29

To 5 ml of N,N-dimethylformamide were added 0.2 g of 4-chloro-6-(2-propynyloxy)pyrimidine, 0.25 g of potassium carbonate, and 0.18 g of 2-methoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.3 g of 4-(2-methoxyphenoxy)-6-(2-propynyloxy)pyrimidine (the present compound (32)).

$^1$H-NMR: 2.52 (t, 1H), 3.77 (s, 3H), 6.20 (s, 1H), 6.96-7.26 (m, 4H), 8.44 (s, 1H)

PRODUCTION EXAMPLE 30

To 2 ml of N,N-dimethylformamide were added 0.2 g of 4-chloro-6-(2-butynyloxy)pyrimidine, 0.23 g of potassium carbonate, and 0.17 g of 2,6-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.15 g of 4-(2-butynyloxy)-6-(2,6-difluorophenoxy)pyrimidine (the present compound (33)), m.p.: 79.8° C.

PRODUCTION EXAMPLE 31

To 5 ml of N,N-dimethylformamide were added 0.2 g of 4-chloro-6-(2-propynyloxy)pyrimidine, 0.25 g of potassium carbonate, and 0.16 g of 2-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.21 g of 4-(2-fluorophenoxy)-6-(2-propynyloxy)pyrimidine (the present compound (34)).

$^1$H-NMR: 2.53 (t, 1H), 5.02 (d, 2H), 6.32 (s, 1H), 7.16-7.29 (m, 4H), 8.44 (s, 1H)

PRODUCTION EXAMPLE 32

To 5 ml of N,N-dimethylformamide were added 0.2 g of 4-chloro-6-(2-propynyloxy)pyrimidine, 0.25 g of potassium carbonate, and 0.16 g of 4-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.15 g of 4-(4-fluorophenoxy)-6-(2-propynyloxy)pyrimidine (the present compound (35)), m.p.: 81.4° C.

PRODUCTION EXAMPLE 33

To 5 ml of N,N-dimethylformamide were added 0.2 g of 4-chloro-6-(2-propynyloxy)pyrimidine, 0.25 g of potassium carbonate, and 0.16 g of 3-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(3-fluorophenoxy)-6-(2-propynyloxy)pyrimidine (the present compound (36)).

$^1$H-NMR: 2.53 (t, 1H), 5.03 (d, 2H), 6.25 (s, 1H), 6.87-6.98 (m, 3H), 7.34-7.42 (m, 1H), 8.48 (s, 1H)

PRODUCTION EXAMPLE 34

In 5 ml of tetrahydrofuran were dissolved 194 mg of 4-chloro-6-phenylpyrimidine and 68 mg of 2-propyn-1-ol, to which 50 mg of sodium hydride (60% in oil) was added with stirring at room temperature, followed by further stirring for 3 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 190 mg of 4-phenyl-6-(2-propynyloxy)pyrimidine (the present compound (37)), m.p.: 65.1° C.

PRODUCTION EXAMPLE 35

In 5 ml of tetrahydrofuran were dissolved 186 mg of 4-chloro-6-phenylpyrimidine and 82 mg of 2-butyn-1-ol, to which 47 mg of sodium hydride (60% in oil) was added with stirring at room temperature, followed by further stirring for 3 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 190 mg of 4-(2-butynyloxy)-6-phenylpyrimidine (the present compound (38)), m.p.: 59.6° C.

PRODUCTION EXAMPLE 36

To 2 ml of N,N-dimethylformamide were added 0.2 g of 4-chloro-6-(2-butynyloxy)pyrimidine, 0.23 g of potassium carbonate, and 0.17 g of 2,3-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.17 g of 4-(2-butynyloxy)-6-(2,3-difluorophenoxy)pyrimidine (the present compound (39)).

$^1$H-NMR: 1.89 (t, 3H), 5.00 (q, 2H), 6.35 (s, 1H), 6.96-7.14 (m, 3H), 8.43 (s, 1H)

PRODUCTION EXAMPLE 37

To 2 ml of N,N-dimethylformamide were added 0.2 g of 4-chloro-6-(2-butynyloxy)pyrimidine, 0.23 g of potassium carbonate, and 0.16 g of 3-cyanophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.2 g of 4-(2-butynyloxy)-6-(3-cyanophenoxy)pyrimidine (the present compound (40)), m.p.: 121.2° C.

PRODUCTION EXAMPLE 38

To 2 ml of N,N-dimethylformamide were added 0.2 g of 4-chloro-6-(2-butynyloxy)pyrimidine, 0.23 g of potassium carbonate and 0.16 g of 4-cyanophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.2 g of 4-(2-butynyloxy)-6-(4-cyanophenoxy)pyrimidine (the present compound (41)), m.p.: 162.0° C.

PRODUCTION EXAMPLE 39

To 2 ml of N,N-dimethylformamide were added 0.2 g of 4-chloro-6-(2-butynyloxy)pyrimidine, 0.23 g of potassium carbonate and 0.16 g of 2-cyanophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.2 g of 4-(2-butynyloxy)-6-(2-cyanophenoxy) pyrimidine (the present compound (42)).

$^1$H-NMR: 1.89 (t, 3H), 5.01 (q, 2H), 6.43 (s, 1H), 7.23-7.39 (m, 2H), 7.63-7.74 (m, 2H), 8.44 (s, 1H)

PRODUCTION EXAMPLE 40

To 2 ml of N,N-dimethylformamide were added 0.2 g of 4-chloro-6-(2-butynyloxy)pyrimidine, 0.23 g of potassium carbonate, and 0.17 g of 2,5-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(2-butynyloxy)-6-(2,5-difluorophenoxy)pyrimidine (the present compound (43)).

$^1$H-NMR: 1.88 (t, 3H), 5.00 (q, 2H), 6.35 (s, 1H), 6.89-7.02 (m, 2H), 7.10-7.20 (m, 1H), 8.43 (s, 1H)

PRODUCTION EXAMPLE 41

To 2 ml of N,N-dimethylformamide were added 0.2 g of 4-chloro-6-(2-butynyloxy)pyrimidine, 0.23 g of potassium carbonate, and 0.17 g of 2,4-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.27 g of 4-(2-butynyloxy)-6-(2,4-difluorophenyl)pyrimidine (the present compound (44)), m.p.: 63.9° C.

PRODUCTION EXAMPLE 42

To 2 ml of N,N-dimethylformamide were added 0.2 g of 4-chloro-6-(2-butynyloxy)pyrimidine, 0.23 g of potassium carbonate, and 0.19 g of 2,4,6-trifluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.3 g of 4-(2-butynyloxy)-6-(2,4,6-trifluorophenoxy)pyrimidine (the present compound (45)), m.p.: 60.3° C.

PRODUCTION EXAMPLE 43

To 2 ml of N,N-dimethylformamide were added 0.2 g of 4-chloro-6-(2-butynyloxy)pyrimidine, 0.23 g of potassium carbonate, and 0.19 g of 2,3,6-trifluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.21 g of 4-(2-butynyloxy)-6-(2,3,6-trifluorophenoxy)pyrimidine (the present compound (46)).

$^1$H-NMR: 1.88 (t, 3H), 5.01 (q, 2H), 6.46 (s, 1H), 6.91-7.11 (m, 2H), 8.41 (s, 1H)

PRODUCTION EXAMPLE 44

To 2 ml of N,N-dimethylformamide were added 0.2 g of 4-chloro-6-(2-butynyloxy)pyrimidine, 0.23 g of potassium carbonate, and 0.22 g of 2-chloro-4,6-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.34 g of 4-(2-butynyloxy)-6-(2-chloro-4,6-difluorophenoxy)pyrimidine (the present compound (47)).

$^1$H-NMR: 1.88 (t, 3H), 5.01 (q, 2H), 6.43 (s, 1H), 6.87-6.95 (m, 1H), 7.03-7.08 (m, 1H), 8.40 (s, 1H)

PRODUCTION EXAMPLE 45

To 2 ml of N,N-dimethylformamide were added 0.2 g of 4-chloro-6-(2-butynyloxy)pyrimidine, 0.23 g of potassium carbonate and 0.24 g of 4-fluoro-3-trifluoromethylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.35 g of 4-(2-butynyloxy)-6-(4-fluoro-3-trifluoromethylphenoxy)pyrimidine (the present compound (48)), m.p.: 90.1° C.

PRODUCTION EXAMPLE 46

To 2 ml of N,N-dimethylformamide were added 0.2 g of 4-chloro-6-(2-butynyloxy)pyrimidine, 0.23 g of potassium carbonate, and 0.23 g of 3-trifluoromethoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.33 g of 4-(2-butynyloxy)-6-(3-trifluoromethoxy)pyrimidine (the present compound (49)), m.p.: 63.1° C.

PRODUCTION EXAMPLE 47

To 2 ml of N,N-dimethylformamide were added 0.2 g of 4-chloro-6-(2-butynyloxy)pyrimidine, 0.23 g of potassium carbonate, and 0.23 g of 4-trifluoromethoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.32 g of 4-(2-butynyloxy)-6-(4-trifluoromethoxy)pyrimidine (the present compound (50)), m.p.: 87.7° C.

PRODUCTION EXAMPLE 48

To 6 ml of N,N-dimethylformamide were added 0.2 g of 4-chloro-6-(2-propynyloxy)pyrimidine, 0.25 g of potassium carbonate, and 0.13 g of phenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.15 g of 4-phenoxy-6-(2-propynyloxy)pyrimidine (the present compound (51)), m.p.: 71.1° C.

PRODUCTION EXAMPLE 49

In 4 ml of tetrahydrofuran was suspended 0.27 g of sodium hydride (60% in oil), to which 0.7 ml of a tetrahydrofuran solution containing 0.33 g of 2-propyn-1-ol was slowly added dropwise with stirring at room temperature. The mixture was stirred at room temperature for 20 minutes and then cooled to 0° C., to which 0.7 ml of a tetrahydrofuran solution containing 0.4 g of 4,6-dichloropyrimidine was slowly added dropwise. After completion of the dropwise addition, the mixture was stirred at room temperature for 40 minutes. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.35 g of 4,6-bis(2-propynyloxy)pyrimidine (the present compound (52)), m.p.: 74.0° C.

PRODUCTION EXAMPLE 50

To 2 ml of N,N-dimethylformamide were added 0.2 g of 4-chloro-6-(2-butynyloxy)pyrimidine, 0.23 g of potassium carbonate and 0.19 g of 4-chloro-2-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.29 g of 4-(2-butynyloxy)-6-(4-chloro-2-fluorophenoxy)pyrimidine (the present compound (4)), m.p.: 117.7° C.

PRODUCTION EXAMPLE 51

To 2 ml of N,N-dimethylformamide were added 0.2 g of 4-chloro-6-(2-butynyloxy)pyrimidine, 0.23 g of potassium carbonate, and 0.17 g of 3,4-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.2 g of 4-(2-butynyloxy)-6-(3,4-difluorophenoxy)pyrimidine (the present compound (10)), m.p.: 109.7° C.

PRODUCTION EXAMPLE 52

In 1.1 ml of ethanol were dissolved 0.2 g of 4-chloro-6-(2-butynyloxy)pyrimidine and 0.15 g of aniline, followed by heating under reflux for 7 hours. The reaction mxiture was then left for cooling to room temperature and concentrated under reduced pressure. The residue was subjected to silica gel column chromatography to give 0.13 g of 4-anilino-6-(2-butynyloxy)pyrimidine (the present compound (53)), m.p.: 159.3° C.

PRODUCTION EXAMPLE 53

In 5 ml of N,N-dimethylformamide were dissolved 212 mg of 4-chloro-6-(2-fluorophenyl)pyrimidine and 68 mg of 2-propyn-1-ol, to which 49 mg of sodium hydride (60% in oil) was added, followed by stirring at room temperature for 8 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 170 mg of 4-(2-fluorophenyl)-6-(2-propynyloxy)pyrimidine (the present compound (54)).
$^1$H-NMR: 2.53 (t, 1H), 5.08 (d, 2H), 7.14-7.24 (m, 1H), 7.26-7.36 (m, 2H), 7.28 (s, 1H), 8.02 (dt, 1H), 8.88 (s, 1H)

PRODUCTION EXAMPLE 54

In 5 ml of N,N-dimethylformamide were dissolved 207 mg of 4-chloro-6-(2-fluorophenyl)pyrimidine and 83 mg of 2-butyn-1-ol, to which 48 mg of sodium hydride (60% in oil) was added, followed by stirring at room temperature for 8 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 160 mg of 4-(2-fluorophenyl)-6-(2-butynyloxy)pyrimidine (the present compound (55)).
$^1$H-NMR: 1.89 (t, 3H), 5.03 (q, 2H), 7.13-7.36 (m, 2H), 7.31 (s, 1H), 7.38-7.50 (m, 1H), 8.02 (dt, 1H), 8.87 (s, 1H)

PRODUCTION EXAMPLE 55

In 7 ml of N,N-dimethylformamide were dissolved 207 mg of 4-chloro-6-(3-fluorophenyl)pyrimidine and 67 mg of 2-propyn-1-ol, to which 48 mg of sodium hydride (60% in oil) was added, followed by stirring at room temperature for 6 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 170 mg of 4-(3-fluorophenyl)-6-(2-propynyloxy)pyrimidine (the present compound (56)).
$^1$H-NMR: 2.53 (t, 1H), 5.09 (d, 2H), 7.15 (s, 1H), 7.15-7.25 (m, 1H), 7.49-7.51 (m, 1H), 7.73-7.83 (m, 2H), 8.86 (s, 1H)

PRODUCTION EXAMPLE 56

In 7 ml of N,N-dimethylformamide were dissolved 204 mg of 4-chloro-6-(3-fluorophenyl)pyrimidine and 82 mg of 2-butyn-1-ol, to which 47 mg of sodium hydride (60% in oil)

was added, followed by stirring at room temperature for 6 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 151 mg of 4-(3-fluorophenyl)-6-(2-butynyloxy)pyrimidine (the present compound (57)).

$^1$H-NMR: 1.89 (t, 3H), 5.04 (q, 21), 7.13-7.26 (m, 1H), 7.13 (s, 1H), 7.40-7.52 (m, 1H), 7.70-7.83 (m, 2H), 8.85 (s, 1H)

PRODUCTION EXAMPLE 57

In 7 ml of N,N-dimethylformamide were dissolved 199 mg of 4-chloro-6-(4-fluorophenyl)pyrimidine and 64 mg of 2-propyn-1-ol, to which 46 mg of sodium hydride (60% in oil) was added, followed by stirring at room temperature for 9 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 150 mg of 4-(4-fluorophenyl)-6-(2-propynyloxy)pyrimidine (the present compound (58)).

$^1$H-NMR: 2.53 (t, 1H), 5.08 (d, 2H), 7.12 (s, 1H), 7.14-7.20 (m, 21), 8.01-8.05 (m, 2H), 8.84 (s, 1H)

PRODUCTION EXAMPLE 58

In 8 ml of N,N-dimethylformamide were dissolved 207 mg of 4-chloro-6-(4-fluorophenyl)pyrimidine and 83 mg of 2-butyn-1-ol, to which 48 mg of sodium hydride (60% in oil) was added, followed by stirring at room temperature for 9 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 138 mg of 4-(4-fluorophenyl)-6-(2-butynyloxy)pyrimidine (the present compound (59)).

$^1$H-NMR: 1.89 (t, 3H), 5.04 (q, 2H), 7.10 (s, 1H), 7.15-7.23 (m, 2H), 7.99-8.09 (m, 2H), 8.83 (s, 1H)

PRODUCTION EXAMPLE 59

To 2 ml of N,N-dimethylformamide were added 0.2 g of 4-chloro-6-(2-pentynyloxy)pyrimidine, 0.21 g of potassium carbonate, and 0.16 g of 2,3-difluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(2,3-difluorophenoxy)-6-(2-pentynyloxy)pyrimidine (the present compound (60)).

$^1$H-NMR: 1.57 (t, 3H), 2.04-2.30 (qt, 2H), 5.02 (t, 2H), 6.35 (s, 1H), 6.97-7.13 (m, 3H), 8.42 (s, 1H)

PRODUCTION EXAMPLE 60

To 2 ml of N,N-dimethylformamide were added 0.2 g of 4-chloro-6-(2-butynyloxy)pyrimidine, 0.23 g of potassium carbonate, and 0.15 g of 3-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.23 g of 4-(3-fluorophenoxy)-6-(2-butynyloxy)pyrimidine (the present compound (61)), m.p.: 60.1° C.

PRODUCTION EXAMPLE 61

To 2 ml of N,N-dimethylformamide were added 0.2 g of 4-chloro-6-(2-butynyloxy)pyrimidine, 0.23 g of potassium carbonate, and 0.15 g of 4-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.19 g of 4-(4-fluorophenoxy)-6-(2-butynyloxy)pyrimidine (the present compound (62)), m.p.: 115.8° C.

PRODUCTION EXAMPLE 62

To 2 ml of N,N-dimethylformamide were added 0.2 g of 4-chloro-6-(2-butynyloxy)pyrimidine, 0.23 g of potassium carbonate, and 0.15 g of 2-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.26 g of 4-(2-fluorophenoxy)-6-(2-butynyloxy)pyrimidine (the present compound (63)).

$^1$H-NMR: 1.88 (t, 3H), 4.99 (q, 2H), 6.31 (s, 1H), 7.16-7.27 (m, 4H), 8.44 (s, 1H)

PRODUCTION EXAMPLE 63

To 2 ml of N,N-dimethylformamide were added 183 mg of 4-chloro-6-(2-butynyloxy)pyrimidine, 166 mg of potassium carbonate, and 138 mg of 2,3-methylenedioxyphenol, followed by stirring at 80° C. for 7 hours and then at 120° C. for 3 hours. The reaction mixture was then left for cooling to room temperature and subjected to phase separation three times between ethyl acetate and an aqueous sodium chloride solution. The organic layers were dried over anhydrous magnesium sulfate and then concentrated. The residue was subjected to silica gel column chromatography to give 193 mg of 4-(2-butynyloxy)-6-(2,3-methylenedioxyphenoxy)pyrimidine (the present compound (64)).

$^1$H-NMR: 1.88 (t, 3H), 4.98 (q, 2H), 5.97 (s, 2H), 6.28 (s, 1H), 6.70 (d, 1H), 6.77 (d, 1H), 6.87 (t, 1H), 8.47 (s, 1H)

PRODUCTION EXAMPLE 64

To 2 ml of N,N-dimethylformamide were added 0.2 g of 4-chloro-6-(2-butynyloxy)pyrimidine, 0.23 g of potassium carbonate, and 0.21 g of 2-fluoro-4-nitrophenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.07 g of 4-(2-fluoro-4-nitrophenoxy)-6-(2-butynyloxy)pyrimidine (the present compound (65)), m.p.: 132.1° C.

PRODUCTION EXAMPLE 65

In 2 ml of tetrahydrofuran was suspended 0.04 g of sodium hydride (60% in oil), to which 0.6 ml of a tetrahydrofuran solution containing 0.05 g of 2-butyn-1-ol was slowly added dropwise with stirring at room temperature. The mixture was stirred at room temperature for 20 minutes and then cooled to 0° C., to which 0.6 ml of a tetrahydrofuran solution containing 0.16 g of 4-chloro-6-(N-methyl-N-(2,3-difluorophenyl)amino)pyrimidine was slowly added dropwise, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.14 g of 4-(N-methyl-N-(2,3-difluorophenyl)amino)-6-(2-butynyloxy)pyrimidine (the present compound (66)), m.p.: 77.5° C.

PRODUCTION EXAMPLE 66

To 2 ml of N,N-dimethylformamide were added 0.2 g of 4-chloro-6-(2-butynyloxy)pyrimidine, 0.23 g of potassium carbonate, and 0.16 g of 2,3-dimethylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water. The organic layer was dried over anhydrous magnesium sulfate and then concentrated. The residue was subjected to silica gel column chromatography to give 0.26 g of 4-(2,3-dimethylphenoxy)-6-(2-butynyloxy)pyrimidine (the present compound (67)).
$^1$H-NMR: 1.87 (t, 3H), 2.06 (s, 3H), 2.31 (s, 3H), 4.96 (q, 2H), 6.07 (s, 1H), 6.87-7.16 (m, 3H), 8.46 (s, 1H)

PRODUCTION EXAMPLE 67

To 2 ml of N,N-dimethylformamide were added 0.15 g of 4-(2-butynyloxy)-6-methanesulfonylpyrimidine, 0.14 g of potassium carbonate, and 0.16 g of 2,6-difluorobenzylalcohol, followed by stirring at 50° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.14 g of 4-(2,6-difluorobenzyloxy)-6-(2-butynyloxy)pyrimidine (the present compound (68)).
$^1$H-NMR: 1.87 (t, 3H), 4.95 (q, 2H), 5.47 (s, 2H), 6.13 (s, 1H), 6.91-6.98 (m, 2H), 7.28-7.40 (m, 1H), 8.50 (s, 1H)

PRODUCTION EXAMPLE 68

To 2 ml of N,N-dimethylformamide were added 0.2 g of 4-chloro-6-(2-butynyloxy)pyrimidine, 0.23 g of potassium carbonate, and 0.22 g of 3-phenylphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water. The organic layer was dried over anhydrous magnesium sulfate and then concentrated. The residue was subjected to silica gel column chromatography to give 0.25 g of 4-(3-phenylphenoxy)-6-(2-butynyloxy)pyrimidine (the present compound (69)).
$^1$H-NMR: 1.86 (t, 3H), 4.97 (q, 2H), 6.22 (s, 1H), 7.11-7.14 (m, 1H), 7.34-7.59 (m, 8H), 8.49 (s, 1H)

PRODUCTION EXAMPLE 69

To 2 ml of N,N-dimethylformamide were added 0.2 g of 4-chloro-6-(2-butynyloxy)pyrimidine, 0.23 g of potassium carbonate, and 0.24 g of 3-phenoxyphenol, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water. The organic layer was dried over anhydrous magnesium sulfate and then concentrated. The residue was subjected to silica gel column chromatography to give 0.33 g of 4-(2-butynyloxy)-6-(3-phenoxyphenoxy)pyrimidine (the present compound (70)).
$^1$H-NMR: 1.86 (t, 3H), 4.97 (q, 2H), 6.19 (s, 1H), 6.77-6.90 (m, 3H), 7.04-7.15 (m, 3H), 7.31-7.38 (m, 3H), 8.47 (s, 1H)

PRODUCTION EXAMPLE 70

To 2 ml of N,N-dimethylformamide were added 0.2 g of 4-chloro-6-(2-butynyloxy)pyrimidine, 0.23 g of potassium carbonate, and 0.18 g of 3'-hydroxyacetophenone, followed by stirring at 60° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.25 g of 4-(2-butynyloxy)-6-(3-acetylphenoxy)pyrimidine (the present compound (71)), m.p.: 94.0° C.

PRODUCTION EXAMPLE 71

In 5 ml of tetrahydrofuran was suspended 0.41 g of potassium t-butoxide, to which 0.56 g of (2,3-difluorophenyl)acetonitrile and 0.5 g of 4-chloro-6-(2-butynyloxy)pyrimidine were added, followed by stirring at room temperature for 4 hours. The reaction mixture was then poured into a saturated aqueous ammonium chloride solution and extracted three times with chloroform. The chloroform layers were combined and washed with a saturated aqueous sodium chloride solution. The organic layer was dried over anhydrous magnesium sulfate and then concentrated. The residue was subjected to silica gel column chromatography to give 0.26 g of 4-(α-cyano-2,3-difluorobenzyl)-6-(2-butynyloxy)pyrimidine (the present compound (72)).

$^1$H-NMR: 1.87 (t, 3H), 5.00 (q, 2H), 5.46 (s, 1H), 6.88 (s, 1H), 6.88-7.35 (m, 3H), 8.77 (s, 1H)

PRODUCTION EXAMPLE 72

In 4 ml of tetrahydrofuran was suspended 0.33 g of sodium hydride (60% in oil), to which 0.6 ml of a tetrahydrofuran solution containing 0.42 g of 2,3-difluoroaniline were slowly added dropwise with stirring at room temperature. The mixture was stirred at room temperature for 20 minutes, to which 1 ml of a tetrahydrofuran solution containing 0.5 g of 4-chloro-6-(2-butynyloxy)pyrimidine was slowly added dropwise, followed by stirring at room temperature for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.25 g of 4-(N-(2,3-difluorophenyl)amino)-6-(2-butynyloxy)pyrimidine (the present compound (73)), m.p.: 147.6° C.

PRODUCTION EXAMPLE 73

In 5 ml of tetrahydrofuran was suspended 0.46 g of potassium t-butoxide, to which 0.39 g of phenylacetonitrile and 0.5 g of 4-chloro-6-(2-butynyloxy)pyrimidine were added, followed by stirring at room temperature for 8 hours. The reaction mixture was then poured into a saturated aqueous ammonium chloride solution and extracted three times with chloroform. The chloroform layers were combined and washed with a saturated aqueous sodium chloride solution. The organic layer was dried over anhydrous magnesium sulfate and then concentrated. The residue was subjected to silica gel column chromatography to give 0.16 g of 4-(α-cyanobenzyl)-6-(2-butynyloxy)pyrimidine (the present compound (74)) and 0.19 g of 4-benzoyl-6-(2-butynyloxy)pyrimidine (the present compound (75)).

The present compound (74):

$^1$H-NMR: 1.86 (t, 3H), 4.98 (q, 2H), 5.17 (s, 1H), 6.84 (s, 1H), 7.35-7.46 (m, 5H), 8.77 (s, 1H)

The present compound (75):

$^1$H-NMR: 1.88 (t, 3H), 5.06 (q, 2H), 7.32 (s, 1H), 7.48 (t, 2H), 7.61 (t, 1H), 8.06 (d, 2H), 8.93 (s, 1H)

PRODUCTION EXAMPLE 74

To 2 ml of N,N-dimethylformamide were added 0.15 g of 4-(2-butynyloxy)-6-methanesulfonylpyrimidine, 0.14 g of potassium carbonate, and 0.16 g of 2,3-difluorobenzylalcohol, followed by stirring at 50° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.13 g of 4-(2,3-difluorobenzyloxy)-6-(2-butynyloxy)pyrimidine (the present compound (76)), m.p.: 84.9° C.

PRODUCTION EXAMPLE 75

In 10 ml of N,N-dimethylformamide were dissolved 304 mg of 4-chloro-2-methyl-6-phenylpyrimidine and 92 mg of 2-propyn-1-ol, to which 66 mg of sodium hydride (60% in oil) was added, followed by stirring at room temperature for 12 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 256 mg of 2-methyl-4-phenyl-6-(2-propynyloxy)pyrimidine (the present compound (77)).

$^1$H-NMR: 2.53 (t, 1H), 2.68 (s, 3H), 5.07 (d, 2H), 6.97 (s, 1H), 7.46 (m, 3H), 8.00 (m, 2H)

PRODUCTION EXAMPLE 76

In 10 ml of N,N-dimethylformamide were dissolved 313 mg of 4-chloro-2-methyl-6-phenylpyrimidine and 118 mg of 2-butyn-1-ol, to which 67 mg of sodium hydride (60% in oil) was added, followed by stirring at room temperature for 12 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 260 mg of 2-methyl-4-phenyl-6-(2-butynyloxy)pyrimidine (the present compound (78)).

$^1$H-NMR: 1.90 (t, 3H), 2.68 (s, 3H), 5.03 (q, 2H), 6.98 (s, 1H), 7.46 (m, 3H), 8.00 (m, 2H)

PRODUCTION EXAMPLE 77

In 2 ml of tetrahydrofuran was suspended 0.03 g of sodium hydride (60% in oil), to which 0.6 ml of a tetrahydrofuran solution containing 0.04 g of 2-butyn-1-ol were slowly added dropwise with stirring at room temperature. The mixture was stirred at room temperature for 20 minutes, to which 0.6 ml of a tetrahydrofuran solution containing 0.16 g of 4-chloro-6-(N-methoxymethyl-N-(2,3-difluorophenyl)amino)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.14 g of 4-(N-methoxymethyl-N-(2,3-difluorophenyl)amino)-6-(2-butynyloxy)pyrimidine (the present compound (79)).

$^1$H-NMR: 1.85 (t, 3H), 3.42 (s, 3H), 4.91 (q, 2H), 5.28 (s, 2H), 5.72 (s, 1H), 7.09-7.25 (m, 3H), 8.43 (s, 1H)

PRODUCTION EXAMPLE 78

In 2 ml of tetrahydrofuran was suspended 0.05 g of sodium hydride (60% in oil), to which 0.6 ml of a tetrahydrofuran solution containing 0.07 g of 2-butyn-1-ol were slowly added dropwise with stirring at room temperature. The mixture was stirred at room temperature for 20 minutes, to which 0.6 ml of a tetrahydrofuran solution containing 0.2 g of 4-chloro-6-(2,6-difluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.24 g of 4-(2,6-difluorobenzyl)-6-(2-butynyloxy)pyrimidine (the present compound (80)), m.p.: 57.6° C.

PRODUCTION EXAMPLE 79

In 0.8 ml of tetrahydrofuran was suspended 0.04 g of sodium hydride (60% in oil), to which 0.6 ml of a tetrahydrofuran solution containing 0.15 g of 4-anilino-6-(2-butynyloxy)pyrimidine were slowly added dropwise with stirring at room temperature. The mixture was stirred at room temperature for 20 minutes, to which 0.4 ml of a tetrahydrofuran solution containing 0.12 g of iodoethane was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.12 g of 4-(N-ethyl-N-phenylamino)-6-(2-butynyloxy)pyrimidine (the present compound (81)).

$^1$H-NMR: 1.20 (t, 3H), 1.83 (t, 3H), 3.98 (q, 2H), 4.85 (q, 2H), 5.54 (s, 1H), 7.19 (d, 2H), 7.32 (t, 1H), 7.44 (t, 2H), 8.38 (s, 1H)

PRODUCTION EXAMPLE 80

In 6 ml of N,N-dimethylformamide were dissolved 96 mg of 4-chloro-6-(2,3-difluorophenyl)pyrimidine and 26 mg of 2-propyn-1-ol, to which 19 mg of sodium hydride. (60% in oil) was added, followed by stirring at room temperature for 8 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 42 mg of 4-(2,3-difluorophenyl)-6-(2-propynyloxy)pyrimidine (the present compound (82)).

$^1$H-NMR: 2.54 (t, 1H), 5.10 (d, 2H), 7.15-7.34 (m, 2H), 7.32 (s, 1H), 7.89 (s, 1H), 8.90 (s, 1H)

PRODUCTION EXAMPLE 81

In 10 ml of N,N-dimethylformamide were dissolved 280 mg of 4-chloro-6-(2,3-difluorophenyl)pyrimidine and 96 mg of 2-butyn-1-ol, to which 55 mg of sodium hydride (60% in oil) was added, followed by stirring at room temperature for 8 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 212 mg of 4-(2,3-difluorophenyl)-6-(2-butynyloxy)pyrimidine (the present compound (83)).

$^1$H-NMR: 1.90 (t, 3H), 5.06 (q, 2H), 7.15-7.34 (m, 21), 7.30 (s, 1H), 7.88 (t, 1H), 8.89 (s, 1H)

PRODUCTION EXAMPLE 82

In 5 ml of tetrahydrofuran was suspended 0.46 g of potassium t-butoxide, to which 0.56 g of 2-chloro-6-fluorobenzylcyanide of formula

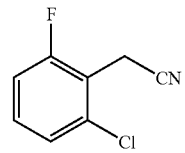

and 0.5 g of 4-chloro-6-(2-butynyloxy)pyrimidine were added, followed by stirring at room temperature 8 hours. The reaction mixture was then poured into a saturated aqueous ammonium chloride solution and extracted three times with chloroform. The chloroform layers were combined and washed with a saturated aqueous sodium chloride solution. The organic layer was dried over anhydrous magnesium sulfate and then concentrated. The residue was subjected to silica gel column chromatography to give 0.25 g of 4-(α-cyano-2-chloro-6-fluorobenzyl)-6-(2-butynyloxy)pyrimidine (the present compound (84)).

$^1$H-NMR: 1.88 (t, 3H), 5.00 (q, 2H), 5.82 (s, 1H), 6.97 (s, 1H), 7.07-7.14 (m, 1H), 7.28-7.42 (m, 2H), 8.75 (s, 1H)

PRODUCTION EXAMPLE 83

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.24 g of 4-chloro-6-(N-cyanomethyl-N-(2,3-difluorophenyl)amino)pyrimidine was slowly added dropwise, followed by stirring at room temperature for 4 hours. The reaction mixture was then poured into a saturated aqueous ammonium chloride solution and extracted three times with chloroform. The chloroform layers were combined, washed with a saturated aqueous sodium chloride solution, dried over anhydrous magnesium sulfate, and then concentrated. The residue was subjected to silica gel column chromatography to give 0.22 g of 4-(2-butynyloxy)-6-(N-cyanomethyl-N-(2,3-difluorophenyl)amino)pyrimidine (the present compound (85)).

$^1$H-NMR: 1.85 (t, 3H), 4.84 (s, 2H), 4.91 (q, 2H), 5.66 (s, 1H), 7.16-7.30 (m, 3H), 8.51 (s, 1H)

PRODUCTION EXAMPLE 84

In 10 ml of N,N-dimethylformamide were dissolved 522 mg of 4-chloro-6-(2-fluorophenyl)pyrimidine and 231 mg of 2-pentyn-1-ol, to which 110 mg of sodium hydride (60% in oil) was added, followed by stirring at room temperature for 6 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 470 mg of 4-(2-fluorophenyl)-6-(2-pentynyloxy)pyrimidine (the present compound (86)).

$^1$H-NMR: 1.19 (t, 3H), 2.22-2.36 (m, 2H), 5.05 (q, 2H), 7.11-7.30 (m, 2H), 7.34 (s, 1H), 7.40-7.50 (m, 1H), 8.02 (dt, 1H), 8.89 (s, 1H)

PRODUCTION EXAMPLE 85

In 10 ml of N,N-dimethylformamide were dissolved 226 mg of 4-chloro-6-(2,6-difluorophenyl)pyrimidine and 84 mg of 2-butyn-1-ol, to which 48 mg of sodium hydride (60% in oil) was added, followed by stirring at room temperature for 9 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 114 mg of 4-(2,6-difluorophenyl)-6-(2-butynyloxy)pyrimidine (the present compound (87)).

$^1$H-NMR: 1.89 (t, 3H), 5.05 (q, 2H), 6.98-7.10 (m, 2H), 7.29 (s, 1H), 7.33-7.46 (m, 1H), 8.92 (s, 1H)

PRODUCTION EXAMPLE 86

In 2 ml of tetrahydrofuran was suspended 0.05 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-fluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.19 g of 4-(2-fluorobenzyl)-6-(2-butynyloxy)pyrimidine (the present compound (88)).

$^1$H-NMR: 1.85 (t, 3H), 4.07 (s, 2H), 4.95 (q, 2H), 6.54 (s, 1H), 7.02-7.12 (m, 2H), 7.21-7.30 (m, 2H), 8.72 (s, 1H)

PRODUCTION EXAMPLE 87

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-chlorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.19 g of 4-(2-chlorobenzyl)-6-(2-butynyloxy)pyrimidine (the present compound (89)).

$^1$H-NMR: 1.85 (t, 3H), 4.18 (s, 2H), 4.94 (q, 2H), 6.48 (s, 1H), 7.21-7.31 (m, 3H), 7.37-7.40 (m, 1H), 8.73 (s, 1H)

PRODUCTION EXAMPLE 88

To 2 ml of N,N-dimethylformamide were added 0.2 g of 4-chloro-6-(2-butynyloxy)pyrimidine, 0.23 g of potassium carbonate, and 0.22 g of 2,3,5,6-tetrafluorophenol, followed by stirring at 60° C. for 7 hours. The reaction mixture was then left for cooling to room temperature and poured into a saturated aqueous ammonium chloride solution, which was extracted three times with chloroform. The chloroform layers were combined and washed with diluted hydrochloric acid and then with water. The organic layer was dried over anhydrous magnesium sulfate and then concentrated. The residue was subjected to silica gel column chromatography to give 0.10 g of 4-(2,3,5,6-tetrafluorophenoxy)-6-(2-butynyloxy)pyrimidine (the present compound (90)).

$^1$H-NMR: 1.89 (t, 3H), 5.02 (q, 2H), 6.48 (s, 1H), 6.97-7.06 (m, 1H), 8.40 (s, 1H)

PRODUCTION EXAMPLE 89

In 2 ml of tetrahydrofuran was suspended 0.06 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-benzylpyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.21 g of 4-(2-butynyloxy)-6-benzylpyrimidine (the present compound (91)).

$^1$H-NMR: 1.84 (t, 3H), 4.02 (s, 2H), 4.94 (q, 2H), 6.52 (s, 1H), 7.23-7.34 (m, 5H), 8.72 (s, 1H)

PRODUCTION EXAMPLE 90

In 2 ml of tetrahydrofuran was suspended 0.06 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-methylbenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.25 g of 4-(2-butynyloxy)-6-(2-methylbenzyl)pyrimidine (the present compound (92)).

$^1$H-NMR: 1.84 (t, 3H), 2.23 (s, 3H), 4.05 (s, 2H), 4.93 (q, 2H), 6.36 (s, 1H), 7.16-7.19 (m, 4H), 8.72 (s, 1H)

PRODUCTION EXAMPLE 91

In 3 ml of tetrahydrofuran was suspended 0.10 g of sodium hydride (60% in oil), to which 0.6 ml of a tetrahydrofuran solution containing 0.14 g of 2-butyn-1-ol was slowly added dropwise with stirring at room temperature. The mixture was stirred at room temperature for 20 minutes, to which 0.6 ml of a tetrahydrofuran solution containing 0.36 g of 4-chloro-6-(N-methyl-N-phenylamino)pyrimidine was slowly added dropwise at room temperature, followed by stirring for 6 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.18 g of 4-(N-methyl-N-phenylamino)-6-(2-butynyloxy)pyrimidine (the present compound (93)), m.p.: 57.6° C.

PRODUCTION EXAMPLE 92

In 2 ml of tetrahydrofuran was suspended 0.06 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(α-methylbenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.16 g of 4-(2-butynyloxy)-6-(α-methylbenzyl)pyrimidine (the present compound (94)).

$^1$H-NMR: 1.66 (d, 3H), 1.84 (t, 3H), 4.14 (q, 1H), 4.94 (q, 2H), 6.57 (s, 1H), 7.18-7.33 (m, 5H), 8.73 (s, 1H)

PRODUCTION EXAMPLE 93

In 2 ml of tetrahydrofuran was suspended 0.04 g of sodium hydride (60% in oil), to which 0.6 ml of a tetrahydrofuran solution containing 0.06 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-trifluoromethylbenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.24 g of 4-(2-butynyloxy)-6-(2-trifluoromethylbenzyl)pyrimidine (the present compound (95)).

$^1$H-NMR: 1.84 (t, 3H), 4.25 (s, 2H), 4.94 (q, 2H), 6.38 (s, 1H), 7.38 (t, 2H), 7.49 (t, 1H), 7.69 (d, 1H), 8.73 (s, 1H)

PRODUCTION EXAMPLE 94

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2,3-difluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.22 g of 4-(2-butynyloxy)-6-(2,3-difluorobenzyl)pyrimidine (the present compound (96)).

$^1$H-NMR: 1.85 (t, 3H), 4.09 (s, 2H), 4.96 (q, 2H), 6.56 (s, 1H), 7.01-7.10 (m, 3H), 8.72 (s, 1H)

PRODUCTION EXAMPLE 95

To 5 ml of chloroform were added 0.57 ml of triethylamine and 0.5 g of 4-chloro-6-(2-butynyloxy)pyrimidine, to which 0.6 ml of a chloroform solution containing 0.33 g of thiophenol was slowly added dropwise, followed by stirring at room temperature for 8 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.22 g of 4-(2-butynyloxy)-6-(thiophenoxy)pyrimidine (the present compound (97)).

$^1$H-NMR: 1.84 (t, 3H), 4.90 (q, 2H), 6.14 (s, 1H), 7.45-7.47 (m, 3H), 7.57-7.60 (m, 2H), 8.54 (s, 1H)

PRODUCTION EXAMPLE 96

In 1.5 ml of tetrahydrofuran was suspended 0.05 g of sodium hydride (60% in oil), to which 0.6 ml of a tetrahydrofuran solution containing 0.2 g of 4-(2-butynyloxy)-6-anilinopyrimidine was slowly added dropwise with stirring at room temperature. The mixture was stirred at room temperature for 20 minutes, to which 0.3 ml of a tetrahydrofuran solution containing 0.17 g of iodopropane was slowly added dropwise at room temperature, followed by stirring for 8 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.12 g of 4-(N-propyl-N-phenylamino)-6-(2-butynyloxy)pyrimidine (the present compound (98)).

$^1$H-NMR: 0.91 (t, 3H), 1.63 (dt, 31), 1.84 (t, 3H), 3.88 (t, 3H), 4.85 (q, 2H), 5.53 (s, 1H), 7.19 (d, 2H), 7.32 (t, 1H), 7.44 (t, 21), 8.37 (s, 1H)

PRODUCTION EXAMPLE 97

In 2 ml of tetrahydrofuran was suspended 0.05 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2,4-difluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.21 g of 4-(2-butynyloxy)-6-(2,4-difluorobenzyl)pyrimidine (the present compound (99)).

$^1$H-NMR: 1.86 (t, 3H), 4.02 (s, 2H), 4.96 (q, 2H), 6.54 (s, 1H), 6.78-6.89 (m, 2H), 7.20-7.31 (m, 1H), 8.72 (s, 1H)

PRODUCTION EXAMPLE 98

In 2 ml of tetrahydrofuran was suspended 0.05 g of sodium hydride (60% in oil), to which 0.6 ml of a tetrahydrofuran solution containing 0.08 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(3-fluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.21 g of 4-(2-butynyloxy)-6-(3-fluorobenzyl)pyrimidine (the present compound (100)), m.p. 51.5° C.

PRODUCTION EXAMPLE 99

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-chloro-6-fluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.26 g of 4-(2-butynyloxy)-6-(2-chloro-6-fluorobenzyl)pyrimidine (the present compound (101)).

$^1$H-NMR: 1.85 (t, 3H), 4.25 (s, 2H), 4.94 (q, 2H), 6.43 (s, 1H), 7.00-7.07 (m, 1H), 7.21-7.24 (m, 2H), 8.72 (s, 1H)

PRODUCTION EXAMPLE 100

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(3-chloro-2-fluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.23 g of 4-(2-butynyloxy)-6-(3-chloro-2-fluorobenzyl)pyrimidine (the present compound (102)).

$^1$H-NMR: 1.86 (t, 3H), 4.07 (s, 2H), 4.95 (q, 2H), 6.56 (s, 1H), 7.02 (t, 1H), 7.15-7.35 (m, 2H), 8.72 (s, 1H)

PRODUCTION EXAMPLE 101

In 2 ml of tetrahydrofuran was suspended 0.04 g of sodium hydride (60% in oil), to which 0.6 ml of a tetrahydrofuran solution containing 0.06 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-bromobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.22 g of 4-(2-butynyloxy)-6-(2-bromobenzyl)pyrimidine (the present compound (103)).

$^1$H-NMR: 1.86 (t, 3H), 4.20 (s, 2H), 4.94 (q, 2H), 6.50 (s, 1H), 7.11-7.17 (m, 1H), 7.28-7.30 (m, 2H), 7.57-7.60 (m, 1H), 8.73 (s, 1H)

PRODUCTION EXAMPLE 102

To 2 ml of N,N-dimethylformamide were added 183 mg of 4-chloro-6-(2-butynyloxy)pyrimidine, 166 mg of potassium carbonate, and 87 mg of N-ethylpropylamine, followed by stirring at 60° C. for 7 hours. Then, 166 mg of potassium carbonate and 87 mg of N-ethylpropylamine were added, and the mixture was stirred at a bath temperature of 60° C. for 6 hours. The reaction mixture was then left for cooling to room temperature and subjected to phase separation three times between ethyl acetate and an aqueous sodium chloride solution. The organic layer was dried over anhydrous magnesium sulfate and then concentrated. The residue was subjected to silica gel thin layer chromatography to give 136 mg of 4-(2-butynyloxy)-6-(N-ethyl-N-propylamino)pyrimidine (the present compound (104)).

$^1$H-NMR: 0.92 (t, 3H), 1.16 (t, 3H), 1.63 (m, 2H), 1.87 (t, 3H), 3.35 (t, 2H), 3.48 (q, 2H), 4.91 (q, 2H), 5.74 (s, 1H), 8.29 (s, 1H)

PRODUCTION EXAMPLE 103

To 2 ml of N,N-dimethylformamide were added 183 mg of 4-chloro-6-(2-butynyloxy)pyrimidine, 166 mg of potassium carbonate, and 87 mg of N-ethylisopropylamine, followed by stirring at 60° C. for 7 hours. Then, 166 mg of potassium carbonate and 435 mg of N-ethylisopropylamine were added, and the mixture was stirred at 80° C. for 8 hours. Then, 166 mg of potassium carbonate and 435 mg of N-ethylisopropylamine were added, and the mixture was stirred at 120° C. for 5 hours. The reaction mixture was then left for cooling to room temperature and subjected to phase separation three times between ethyl acetate and an aqueous sodium chloride solution. The organic layer was dried over anhydrous magnesium sulfate and then concentrated. The residue was subjected to preparative silica gel thin layer chromatography to give 79 mg of 4-(2-butynyloxy)-6-(N-ethyl-N-isopropylamino)pyrimidine (the present compound (105)).

$^1$H-NMR: 1.17 (t, 3H), 1.19 (d, 6H), 1.88 (t, 3H), 3.33 (q, 2H), 4.80 (br, 1H), 4.91 (q, 2H), 5.76 (s, 1H), 8.31 (s, 1H)

PRODUCTION EXAMPLE 104

To 4 ml of dimethylsulfoxide were added 365 mg of 4-chloro-6-(2-butynyloxy)pyrimidine, 332 mg of potassium carbonate, and 591 mg of isopropylamine, followed by stirring at 70° C. for 6 hours. The reaction mixture was then left for cooling to room temperature, diluted with tert-butyl methyl ether, and washed twice with an aqueous sodium chloride solution. The organic layer was dried over anhydrous magnesium sulfate and concentrated. The residue was subjected to silica gel thin layer chromatography to give 339 mg of 4-(2-butynyloxy)-6-(isopropylamino)pyrimidine (the present compound (106)).

$^1$H-NMR: 1.22 (d, 6H), 1.87 (t, 3H), 3.76 (m, 1H), 4.88 (br, 1H), 4.91 (q, 2H), 5.68 (s, 1H), 8.22 (s, 1H)

PRODUCTION EXAMPLE 105

In 5 ml of tetrahydrofuran were dissolved 164 mg of 4-(2-butynyloxy)-6-(isopropylamino)pyrimidine and 106 mg of 1-bromo-2-butyne, to which 40 mg of sodium hydride (60% in oil) was added, followed by stirring at room temperature for 6 hours. Then, ice water was added to the reaction mixture, which was extracted with ethyl acetate. The organic layer was washed with an aqueous sodium chloride solution, dried over anhydrous magnesium sulfate, and then concentrated. The residue was subjected to preparative silica gel thin layer chromatography to give 155 mg of 4-(2-butynyloxy)-6-(N-(2-butynyl)-N-isopropylamino)pyrimidine (the present compound (107)).

$^1$H-NMR: 1.24 (d, 6H), 1.76 (t, 3H), 1.88 (t, 3H), 3.99 (d, 2H), 4.80 (br, 1H), 4.92 (q, 2H), 5.93 (s, 1H), 8.35 (s, 1H)

PRODUCTION EXAMPLE 106

To 20 ml of dimethylsulfoxide were added 1.83 g of 4-chloro-6-(2-butynyloxy)pyrimidine, 2.20 g of potassium carbonate, and 20 ml of ethylamine (2.0 M tetrahydrofuran solution), followed by stirring at 50° C. for 8 hours. The reaction mixture was then left for cooling to room temperature, diluted with tert-butyl methyl ether, and washed twice with an aqueous sodium chloride solution. The organic layer was dried over anhydrous magnesium sulfate and concentrated. The residue was recrystallized from tert-butyl methyl ether to give 1.14 g of 4-(2-butynyloxy)-6-(ethylamino)pyrimidine (the present compound (108)).

$^1$H-NMR: 1.25 (t, 3H), 1.87 (t, 3H), 3.23 (m, 2H), 4.90 (br, 1H), 4.92 (q, 2H), 5.69 (s, 1H), 8.24 (s, 1H)

PRODUCTION EXAMPLE 107

In 5 ml of tetrahydrofuran were dissolved 153 mg of 4-(2-butynyloxy)-6-(ethylamino)pyrimidine and 117 mg of 1-bromo-2-butyne, to which 40 mg of sodium hydride (60% in oil) was added, followed by stirring at room temperature for 7 hours. Then, 2 ml of N,N-dimethylformamide was further added, and the mixture was stirred at room temperature for 3 hours. Then, ice water was added to the reaction mixture, which was extracted with ethyl acetate. The organic layer was washed twice with an aqueous sodium chloride solution, dried over anhydrous magnesium sulfate, and then concentrated. The residue was subjected to preparative silica gel thin layer chromatography to give 176 mg of 4-(2-butynyloxy)-6-(N-ethyl-N-(2-butynyl)amino)pyrimidine (the present compound (109)).

$^1$H-NMR: 1.20 (t, 3H), 1.79 (t, 3H), 1.88 (t, 3H), 3.56 (q, 2H), 4.21 (d, 2H), 4.92 (q, 2H), 5.87 (s, 1H), 8.35 (s, 1H)

PRODUCTION EXAMPLE 108

In 2 ml of N,N-dimethylformamide were dissolved 153 mg of 4-(2-butynyloxy)-6-(ethylamino)pyrimidine and 67 mg of allyl chloride, to which 40 mg of sodium hydride (60% in oil) was added, followed by stirring at room temperature for 3 hours. Then, ice water was added to the reaction mixture, which was extracted with ethyl acetate. The organic layer was washed twice with an aqueous sodium chloride solution, dried over anhydrous magnesium sulfate, and then concentrated. The residue was subjected to preparative silica gel thin layer chromatography to give 157 mg of 4-(2-butynyloxy)-6-(N-ethyl-N-allylamino)pyrimidine (the present compound (110)).

$^1$H-NMR: 1.16 (t, 3H), 1.87 (t, 3H), 3.48 (q, 2H), 4.06 (d, 2H), 4.91 (q, 2H), 5.05-5.2 (m, 2H), 5.79 (s, 1H), 5.7-5.9 (m, 1H), 8.31 (s, 1H)

PRODUCTION EXAMPLE 109

In 2 ml of tetrahydrofuran was suspended 0.05 g of sodium hydride (60% in oil), to which 0.6 ml of a tetrahydrofuran solution containing 0.07 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(1-(3-fluorophenyl)ethyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.21 g of 4-(2-butynyloxy)-6-(1-(3-fluorophenyl)ethyl)pyrimidine (the present compound (116)).

$^1$H-NMR: 1.61 (d, 3H), 1.85 (t, 3H), 4.13 (q, 1H), 4.96 (q, 2H), 6.58 (s, 1H), 6.88-7.04 (m, 3H), 7.22-7.30 (m, 1H), 8.74 (s, 1H)

PRODUCTION EXAMPLE 110

To 4 ml of dimethylsulfoxide were added 365 mg of 4-chloro-6-(2-butynyloxy)pyrimidine, 442 mg of potassium carbonate, and 495 mg of 2,2,3,3,3-pentafluoropropylamine, followed by stirring at 80° C. for 4 hours. Then, 596 mg of 2,2,3,3,3-pentafluoropropylamine was further added, and the mixture was stirred at 100° C. for 6 hours. The reaction mixture was then left for cooling to room temperature, diluted with ethyl acetate, and washed twice with an aqueous sodium chloride solution. The organic layer was dried over anhydrous magnesium sulfate and concentrated. The residue was subjected to silica gel column chromatography to give 73 mg of 4-(2-butynyloxy)-6-(2,2,3,3,3-pentafluoropropylamino)pyrimidine (the present compound (111)).

$^1$H-NMR: 1.87 (t, 3H), 4.12 (dt, 2H), 4.93 (q, 2H), 5.13 (br, 1H), 5.86 (s, 1H), 8.33 (s, 1H)

PRODUCTION EXAMPLE 111

In 2 ml of N,N-dimethylformamide were dissolved 73 mg of 4-(2-butynyloxy)-6-(2,2,3,3,3-pentafluoropropylamino)pyrimidine and 47 mg of ethyl iodide, to which 12 mg of sodium hydride (60% in oil) was added, followed by stirring at room temperature for 3.5 hours. Then, ice water was added to the reaction mixture, which was extracted with ethyl acetate. The organic layer was washed twice with an aqueous sodium chloride solution, dried over anhydrous magnesium sulfate, and then concentrated. The residue was subjected to preparative silica gel thin layer chromatography to give 43 mg of 4-(2-butynyloxy)-6-(N-ethyl-N-(2,2,3,3,3-pentafluoropropyl)amino)pyrimidine (the present compound (112)).

$^1$H-NMR: 1.21 (t, 3H), 1.88 (t, 3H), 3.52 (q, 2H), 4.33 (q, 2H), 4.93 (q, 2H), 5.93 (s, 1H), 8.34 (s, 1H)

PRODUCTION EXAMPLE 112

To 2 ml of dimethylsulfoxide were added 183 mg of 4-chloro-6-(2-butynyloxy)pyrimidine, 166 mg of potassium carbonate, and 152 mg of dipropylamine, followed by stirring at 80° C. for 8 hours. The reaction mixture was then left for cooling to room temperature, diluted with ethyl acetate, and washed twice with an aqueous sodium chloride solution. The organic layer was dried over anhydrous magnesium sulfate and concentrated. The residue was subjected to silica gel thin layer chromatography to give 179 mg of 4-(2-butynyloxy)-6-(dipropylamino)pyrimidine (the present compound (113)).

$^1$H-NMR: 0.91 (t, 6H), 1.60 (m, 4H), 1.88 (t, 3H), 3.35 (t, 4H), 4.91 (q, 2H), 5.73 (s, 1H), 8.29 (s, 1H)

PRODUCTION EXAMPLE 113

To 2 ml of dimethylsulfoxide were added 183 mg of 4-chloro-6-(2-butynyloxy)pyrimidine, 220 mg of potassium carbonate, and 495 mg of 2,2,2-trifluoroethylamine, followed by stirring at a bath temperature of 60° C. for 9 hours. Then, 495 mg of 2,2,2-trifluoroethylamine was further added, and the mixture was stirred at 80° C. for 8 hours. Then, 495 mg of 2,2,2-trifluoroethylamine and 2 ml of dimethylsulfoxide were further added, and the mixture was stirred at 80° C. for 8 hours. The reaction mixture was then left for cooling to room temperature, diluted with ethyl acetate, and washed twice with an aqueous sodium chloride solution. The organic layer was dried over anhydrous magnesium sulfate and concentrated. The residue was subjected to silica gel thin layer chromatography to give 60 mg of 4-(2-butynyloxy)-6-(2,2,2-trifluoroethylamino)pyrimidine (the present compound (114)).

$^1$H-NMR: 1.87 (t, 3H), 4.08 (dq, 2H), 4.93 (q, 2H), 5.02 (br, 1H), 5.85 (s, 1H), 8.39 (s, 1H)

PRODUCTION EXAMPLE 114

In 2 ml of N,N-dimethylformamide were dissolved 40 mg of 4-(2-butynyloxy)-6-(2,2,2-trifluoroethylamino)pyrimidine and 31 mg of ethyl iodide, to which 8 mg of sodium hydride (60% in oil) was added, followed by stirring at room temperature for 1 hour. Then, 6 ml of tetrahydrofuran was added, and the mixture was further stirred at room temperature for 4.5 hours. Then, ice water was added to the reaction mixture, from which the tetrahydrofuran was distilled out under reduced pressure. The residue was extracted with tert-butyl methyl ether. The organic layer was washed twice with an aqueous sodium chloride solution, dried over anhydrous magnesium sulfate, and then concentrated. The residue was subjected to silica gel thin layer chromatography to give 37 mg of 4-(2-butynyloxy)-6-(N-ethyl-N-2,2,2-trifluoroethylamino)pyrimidine (the present compound (115)).

$^1$H-NMR: 1.20 (t, 31), 1.88 (t, 3H), 3.51 (q, 2H), 4.24 (q, 2H), 4.93 (q, 2H), 5.93 (s, 1H), 8.35 (s, 1H)

PRODUCTION EXAMPLE 115

In 9 ml of N,N-dimethylformamide were dissolved 202 mg of 4-chloro-6-(2,3-difluorophenyl)pyrimidine and 112 mg of 2-pentyn-1-ol, to which 54 mg of sodium hydride (60% in oil) was added, followed by stirring at room temperature for 5 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 211 mg of 4-(2,3-difluorophenyl)-6-(2-pentynyloxy)pyrimidine (the present compound (117)).

$^1$H-NMR: 1.19 (t, 3H), 2.28 (q, 2H), 5.06 (t, 2H), 7.15-7.34 (m, 2H), 7.30 (s, 1H), 7.86 (t, 1H), 8.88 (s, 1H)

PRODUCTION EXAMPLE 116

In 9 ml of N,N-dimethylformamide were dissolved 217 mg of 4-chloro-6-(2,3-difluorophenyl)pyrimidine and 141 mg of 2-hexyn-1-ol, to which 58 mg of sodium hydride (60% in oil) was added, followed by stirring at room temperature for 7 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 247 mg of 4-(2,3-difluorophenyl)-6-(2-hexynyloxy)pyrimidine (the present compound (118)).

$^1$H-NMR: 0.98 (t, 3H), 1.55 (sextet, 2H), 2.23 (quintet, 2H), 5.06 (t, 2H), 7.15-7.34 (m, 2H), 7.30 (s, 1H), 7.87 (t, 1H), 8.88 (s, 1H)

PRODUCTION EXAMPLE 117

In 6 ml of N,N-dimethylformamide were dissolved 199 mg of 4-chloro-6-(2,3-difluorophenyl)pyrimidine and 118 mg of 4,4-dimethyl-2-pentyn-1-ol, to which 43 mg of sodium hydride (60% in oil) was added, followed by stirring at room temperature for 3 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 190 mg of 4-(4,4-dimethyl-2-pentynyloxy)-6-(2,3-difluorophenyl)pyrimidine (the present compound (119)).

$^1$H-NMR: 1.22 (s, 9H), 5.05 (s, 2H), 7.14-7.35 (m, 2H), 7.30 (s, 1H), 7.88 (t, 1H), 8.86 (s, 1H)

PRODUCTION EXAMPLE 122

In 1 ml of tetrahydrofuran was suspended 0.02 g of sodium hydride (60% in oil), to which 0.3 ml of a tetrahydrofuran solution containing 0.02 g of 2-butyn-1-ol was slowly added dropwise with stirring at room temperature. The mixture was then stirred at room temperature for 20 minutes, to which 0.3 ml of a tetrahydrofuran solution containing 0.06 g of 4-chloro-6-(1-(2-fluorophenyl)ethyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.06 g of 4-(2-butynyloxy)-6-(1-(2-fluorophenyl)ethyl)pyrimidine (the present compound (120)).

$^1$H-NMR: 1.66 (d, 3H), 1.86 (t, 3H), 4.45 (q, 1H), 4.95 (q, 2H), 6.60 (s, 1H), 6.98-7.36 (m, 4H), 8.74 (s, 1H)

PRODUCTION EXAMPLE 123

In 2 ml of tetrahydrofuran was suspended 0.04 g of sodium hydride (60% in oil), to which 0.6 ml of a tetrahydrofuran solution containing 0.06 g of 2-butyn-1-ol was slowly added dropwise with stirring at room temperature. The mixture was then stirred at room temperature for 20 minutes, to which 0.6 ml of a tetrahydrofuran solution containing 0.2 g of 4-chloro-6-(2-chloro-5-methyl-6-fluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.24 g of 4-(2-butynyloxy)-6-(2-chloro-5-methyl-6-fluorobenzyl)pyrimidine (the present compound (121)).

$^1$H-NMR: 1.86 (t, 3H), 2.35 (s, 3H), 4.26 (s, 2H), 4.94 (q, 2H), 6.41 (s, 1H), 6.95 (t, 1H), 7.16 (dd, 1H), 8.73 (s, 1H)

PRODUCTION EXAMPLE 124

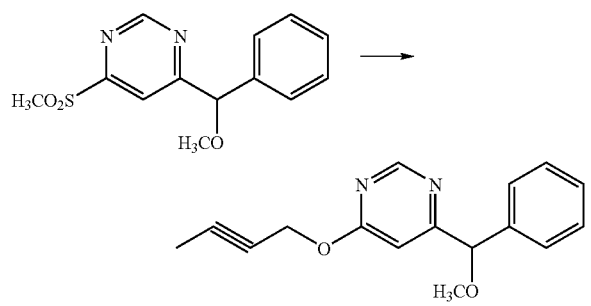

In 2 ml of tetrahydrofuran was suspended 0.04 g of sodium hydride, to which 0.06 g of 2-butyn-1-ol dissolved in 0.3 ml of tetrahydrofuran was added at room temperature. The mixture was then stirred for 15 minutes, to which 0.2 g of 4-(α-methoxyphenylmethyl)-6-methanesulfonylpyrimidine dissolved in 0.3 ml of tetrahydrofuran was added dropwise under ice cooling, followed by further stirring for 30 minutes. The reaction mixture was then poured into a saturated aqueous ammonium chloride solution and extracted three times with chloroform. The organic layers were combined, washed with water, dried over anhydrous magnesium sulfate, and then concentrated. The residue was subjected to silica gel column chromatography to give 0.14 g of 4-(2-butynyloxy)-6-(α-methoxybenzyl)pyrimidine (the present compound (122)).

$^1$H-NMR: 1.86 (t, 3H), 3.41 (s, 3H), 4.97 (q, 2H), 5.21 (s, 1H), 7.02 (s, 1H), 7.28-7.42 (m, 5H), 8.69 (s, 1H)

PRODUCTION EXAMPLE 125

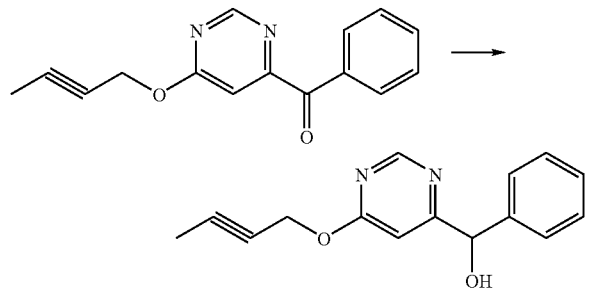

In 2 ml of ethanol was suspended 0.5 g of 6-(2-butynyloxy)-4-benzoylpyrimidine, to which 0.11 g of sodium borohydride was added, followed by stirring at 0° C. for 4 hours. The reaction mixture was then poured into a saturated aqueous ammonium chloride solution and extracted three times with ethyl acetate. The organic layers were combined and washed with a saturated aqueous sodium chloride solution, and the combined organic layer was then dried over anhydrous magnesium sulfate and concentrated. The residue was subjected to silica gel column chromatography to give 0.4 g of 6-(2-butynyloxy)-4-(α-hydroxybenzyl)pyrimidine (the present compound (123)).

$^1$H-NMR: 1.84 (t, 3H), 4.58 (bs, 1H), 4.95 (q, 2H), 5.63 (s, 1H), 6.72 (s, 1H), 7.28-7.38 (m, 5H), 8.71 (s, 1H)

PRODUCTION EXAMPLE 126

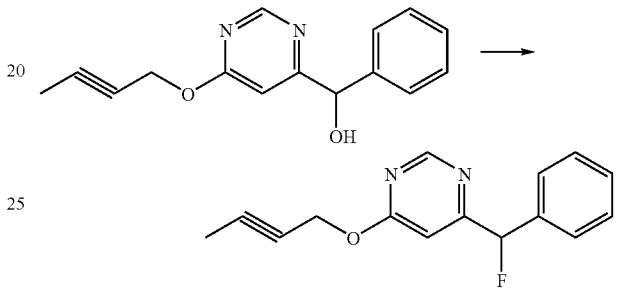

In 4 ml of acetonitrile was dissolved 0.26 g of 6-(2-butynyloxy)-4-α-hydroxybenzyl)pyrimidine, to which a solution of 0.17 g of 2,2-difluoro-1,3-dimethylimidazolidine in 1.5 ml of acetonitrile was added, followed by stirring at room temperature for 4 hours. The reaction mixture was then poured into a saturated aqueous ammonium chloride solution and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.14 g of 4-(2-butynyloxy)-6-(α-fluorobenzyl)pyrimidine (the present compound (124)).

$^1$H-NMR: 1.87 (t, 3H), 5.00 (q, 2H), 6.35 (d, 1H), 7.07 (s, 1H), 7.35-7.44 (m, 5H), 8.72 (s, 1H)

PRODUCTION EXAMPLE 127

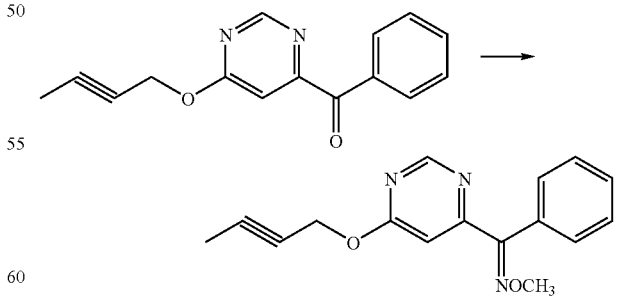

In 3 ml of pyridine were added 0.3 g of 6-(2-butynyloxy)-4-benzoylpyrimidine and 0.15 g of O-methylhydroxylamine hydrochloride, followed by stirring at room temperature for 3 hours. The reaction mixture was then poured into 10% hydrochloric acid and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give two isomers of (6-(2-butynyloxy)-4-pyrimidyl)phenylketone O-methyloxime (referred to as isomers A and B).

Isomer A (the present compound (125)): 0.25 g
Isomer B (the present compound (126)): 0.07 g
Isomer A
$^1$H-NMR: 1.89 (t, 3H), 3.98 (s, 3H), 5.04 (q, 2H), 6.93 (s, 1H), 7.32-7.48 (m, 5H), 8.90 (s, 1H)
Isomer B
$^1$H-NMR: 1.87 (t, 3H), 4.05 (s, 3H), 4.99 (q, 2H), 6.98 (s, 1H), 7.32-7.36 (m, 2H), 7.41-7.48 (m, 3H), 8.81 (s, 1H)

PRODUCTION EXAMPLE 128

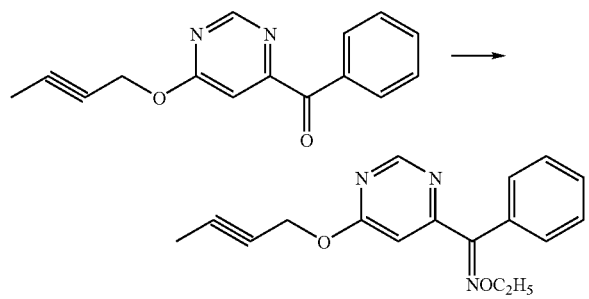

In 3 ml of pyridine were added 0.3 g of 6-(2-butynyloxy)-4-benzoylpyrimidine and 0.17 g of O-ethylhydroxylamine hydrochloride, followed by stirring at room temperature for 3 hours. The reaction mixture was then poured into 10% hydrochloric acid and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give two isomers of (6-(2-butynyloxy)-4-pyrimidyl)phenylketone O-ethyloxime (referred to as isomers A and B).

Isomer A (the present compound (127)): 0.20 g
Isomer B (the present compound (128)): 0.12 g
Geometrical Isomer A
$^1$H-NMR: 1.29 (t, 3H), 1.88 (t, 3H), 4.24 (q, 2H), 5.05 (q, 2H), 6.97 (s, 1H), 7.29-7.34 (m, 3H), 7.45-7.48 (m, 2H), 8.90 (s, 1H)
Geometrical Isomer B
$^1$H-NMR: 1.31 (t, 3H), 1.86 (t, 3H), 4.32 (q, 2H), 4.99 (q, 2H), 7.05 (s, 1H), 7.34-7.46 (m, 5H), 8.80 (s, 1H)

PRODUCTION EXAMPLE 129

To 4 ml of ethanol were added 0.5 g of 4-chloro-6-(2-butynyloxy)pyrimidine and 0.68 g of N-ethyl-N-benzylamine, followed by heating under reflux for 6 hours. The reaction mixture was then left for cooling to room temperature and concentrated under reduced pressure. A saturated aqueous ammonium chloride solution was poured onto the residue, which was extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.42 g of 6-(2-butynyloxy)-4-(N-ethyl-N-benzylamino)pyrimidine (the present compound (129)).

$^1$H-NMR: 1.14 (t, 3H), 1.84 (t, 3H), 3.29 (q, 2H), 4.71 (s, 2H), 4.91 (q, 2H), 5.78 (s, 1H), 7.17-7.32 (m, 5H), 8.34 (s, 1H)

PRODUCTION EXAMPLE 130

In 2 ml of tetrahydrofuran was suspended 0.04 g of sodium hydride (60% in oil), to which 0.6 ml of a tetrahydrofuran solution containing 0.06 g of 2-butyn-1-ol was slowly added dropwise with stirring at room temperature. The mixture was stirred at room temperature for 20 minutes, to which 0.6 ml of a tetrahydrofuran solution containing 0.2 g of 4-chloro-6-(2-chloro-3,6-difluorobenzyl)pyrimidine was slowly added dropwise at room temperature, followed by stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.22 g of 4-(2-butynyloxy)-6-(2-chloro-3,6-difluorobenzyl)pyrimidine (the present compound (130)).

$^1$H-NMR: 1.86 (t, 3H), 4.25 (s, 2H), 4.95 (q, 2H), 6.46 (s, 1H), 6.99-7.14 (m, 2H), 8.72 (s, 1H)

PRODUCTION EXAMPLE 131

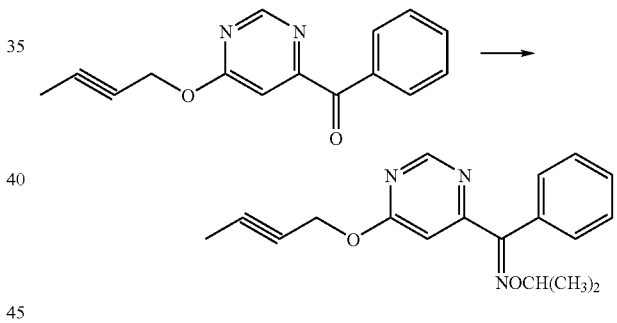

In 3 ml of pyridine were added 0.3 g of 6-(2-butynyloxy)-4-benzoylpyrimidine and 0.20 g of O-isopropylhydroxylamine hydrochloride, followed by stirring at room temperature for 3 hours. The reaction mixture was then poured into 10% hydrochloric acid and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give two isomers of (6-(2-butynyloxy)-4-pyrimidyl)phenylketone O-isopropyloxime (referred to as isomers A and B).

Isomer A (the present compound (131)): 0.26 g
Isomer B (the present compound (132)): 0.15 g
Isomer A
$^1$H-NMR: 1.26 (d, 6H), 1.89 (t, 3H), 4.43-4.55 (m, 1H), 5.05 (q, 2H), 6.99 (s, 1H), 7.30-7.36 (m, 3H), 7.44-7.48 (m, 2H), 8.89 (s, 1H)
Isomer B
$^1$H-NMR: 1.29 (d, 6H), 1.87 (t, 3H), 4.50-4.61 (m, 1H), 4.99 (q, 2H), 7.12 (s, 1H), 7.37-7.41 (m, 5H), 8.79 (s, 1H)

PRODUCTION EXAMPLE 132

In 8 ml of ethanol were added 1 g of 4-chloro-6-(2-butynyloxy)pyrimidine and 1.17 g of benzylamine, followed by heating under reflux for 6 hours. The reaction mixture was then left for cooling to room temperature and concentrated under reduced pressure. A saturated aqueous ammonium chloride solution was poured onto the residue, which was extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 1.58 g of 6-(2-butynyloxy)-4-benzylaminopyrimidine (the present compound (133)).

$^1$H-NMR: 1.86 (t, 3H), 4.43 (d, 2H), 4.90 (q, 2H), 5.38 (bs, 1H), 5.70 (s, 1H), 7.28-7.37 (m, 5H), 8.25 (s, 1H)

PRODUCTION EXAMPLE 133

In 6 ml of N,N-dimethylformamide were dissolved 150 mg of 4-chloro-6-(2,3-difluorophenyl)pyrimidine and 56 mg of 3-butyn-2-ol, to which 32 mg of sodium hydride (60% in oil) was added, followed by stirring at room temperature for 12 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 120 mg of 4-(2,3-difluorophenyl)-6-(1-methyl-2-propynyloxy)pyrimidine (the present compound (134)).

$^1$H-NMR: 1.68 (d, 3H), 2.49 (t, 1H), 5.89 (dq, 1H), 7.17-7.42 (m, 2H), 7.82-7.92 (m, 1H), 7.89 (s, 1H), 8.89 (s, 1H)

PRODUCTION EXAMPLE 134

In 6 ml of acetonitrile was dissolved 255 mg of 4-(2,3-difluorophenyl)-6-(4-hydroxy-2-butynyloxy)pyrimidine, to which 148 mg of 2,2-difluoro-1,3-dimethylimidazolidine was added, followed by stirring at room temperature for 24 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 43 mg of 4-(2,3-difluorophenyl)-6-(4-fluoro-2-butynyloxy)pyrimidine (the present compound (135)).

$^1$H-NMR: 5.04 (dt, 2H), 5.17 (dd, 2H), 7.12-7.51 (m, 3H), 7.33 (s, 1H), 8.14 (t, 1H), 8.90 (s, 1H)

PRODUCTION EXAMPLE 135

In 5 ml of carbon tetrachloride was dissolved 241 mg of 4-(2,3-difluorophenyl)-6-(2-propynyloxy)pyrimidine, to which 136 mg of potassium carbonate and 136 mg of tetra-n-butylammonium chloride were added, followed by stirring at room temperature for 16 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 159 mg of 4-(2,3-difluorophenyl)-6-(3-chloro-2-propynyloxy)pyrimidine (the present compound (136)).

$^1$H-NMR: 5.09 (s, 2H), 7.16-7.34 (m, 3H, involving a singlet at 7.29), 7.88 (t, 1H), 8.90 (s, 1H)

PRODUCTION EXAMPLE 136

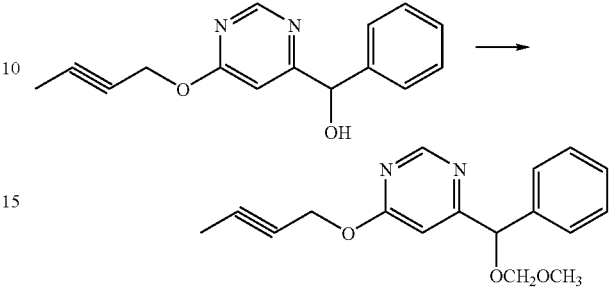

In 1.5 ml of tetrahydrofuran was suspended 0.05 g of sodium hydride (60% in oil), to which 0.2 g of 6-(2-butynyloxy)-4-(α-hydroxybenzyl)pyrimidine was added under ice cooling, followed by stirring for 15 minutes. Then, 0.2 ml of a tetrahydrofuran solution containing 0.08 g of chloromethyl methyl ether was slowly added dropwise, followed by further stirring at the same temperature for 2 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.25 g of 6-(2-butynyloxy)-4-(α-methoxymethoxybenzyl)pyrimidine (the present compound (137)).

$^1$H-NMR: 1.86 (t, 3H), 3.36 (s, 3H), 4.71 (dd, 2H), 4.98 (q, 2H), 5.67 (s, 1H), 7.08 (s, 1H), 7.27-7.43 (m, 5H), 8.70 (s, 1H)

PRODUCTION EXAMPLE 137

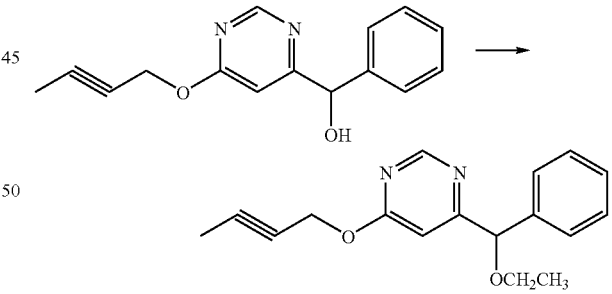

In 1.5 ml of tetrahydrofuran was suspended 0.05 g of sodium hydride (60% in oil), to which 0.2 g of 6-(2-butynyloxy)-4-(α-hydroxybenzyl)pyrimidine was added under ice cooling, followed by stirring for 15 minutes. Then, 0.2 ml of a tetrahydrofuran solution containing 0.18 g of ethyl iodide was slowly added dropwise, followed by further stirring at the same temperature for 2 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.07 g of 6-(2-butynyloxy)-4-(α-ethoxybenzyl)pyrimidine (the present compound (138)).

¹H-NMR: 1.27 (t, 3H), 1.86 (t, 3H), 3.55 (q, 2H), 4.97 (q, 2H), 5.32 (s, 1H), 7.07 (s, 1H), 7.27-7.43 (m, 5H), 8.68 (s, 1H)

PRODUCTION EXAMPLE 138

To 1.8 ml of tetrahydrofuran were added 0.15 ml of diisopropylethylamine and 0.15 g of 6-(2-butynyloxy)-4-(α-hydroxybenzyl)pyrimidine under ice cooling. Then, 0.2 ml of a tetrahydrofuran solution containing 0.06 g of acetyl chloride was slowly added dropwise, followed by further stirring at the same temperature for 3 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.18 g of the present compound (139) of the following formula

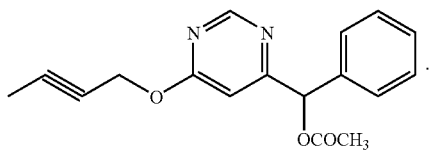

¹H-NMR: 1.86 (t, 3H), 2.19 (s, 3H), 4.98 (q, 2H), 6.70 (s, 1H), 6.90 (s, 1H), 7.30-7.43 (m, 5H), 8.72 (s, 1H)

PRODUCTION EXAMPLE 139

To 1.8 ml of tetrahydrofuran were added 0.15 ml of diisopropylethylamine and 0.15 g of 6-(2-butynyloxy)-4-(α-hydroxybenzyl)pyrimidine under ice cooling. Then, 0.2 ml of a tetrahydrofuran solution containing 0.07 g of propionyl chloride was slowly added dropwise, and after completion of the dropwise addition, the mixture was stirred at the same temperature for 3 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.12 g of the present compound (140) of the following formula

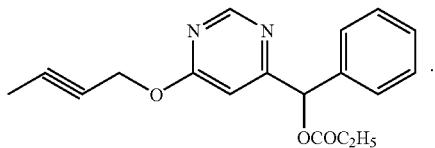

¹H-NMR: 1.19 (t, 3H), 1.86 (t, 3H), 2.58 (q, 2H), 4.97 (q, 2H), 6.71 (s, 1H), 6.90 (s, 1H), 7.29-7.44 (m, 5H), 8.72 (s, 1H)

PRODUCTION EXAMPLE 140

To 1.8 ml of tetrahydrofuran were added 0.15 ml of diisopropylethylamine and 0.15 g of 6-(2-butynyloxy)-4-(α-hydroxybenzyl)pyrimidine under ice cooling. Then, 0.2 ml of a tetrahydrofuran solution containing 0.08 g of isobutyryl chloride was slowly added dropwise, and after completion of the dropwise addition, the mixture was stirred at the same temperature for 3 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.21 g of the present compound (141) of the following formula

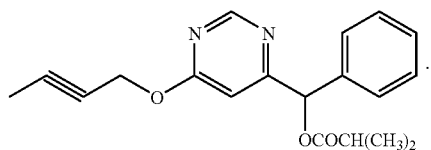

¹H-NMR: 1.21-1.26 (m, 6H), 1.87 (t, 3H), 2.46-2.77 (m, 1H), 4.98 (q, 2H), 6.69 (s, 1H), 6.91 (s, 1H), 7.27-7.43 (m, 5H), 8.71 (s, 1H)

PRODUCTION EXAMPLE 141

To 5 ml of chloroform were added 0.95 ml of diisopropylethylamine, 0.5 g of 4-(2-butynyloxy)-6-chloropyrimidine, and 0.42 g of 2-chlorothiophenol, followed by stirring at room temperature for 7 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.51 g of 4-(2-butynyloxy)-6-(2-chlorothiophenoxy)pyrimidine (the present compound (142)).

¹H-NMR: 1.84 (t, 3H), 4.91 (q, 2H), 6.13 (s, 1H), 7.34 (dt, 1H), 7.44 (dt, 1H), 7.57 (dd, 1H), 7.69 (dd, 1H), 8.55 (s, 1H)

PRODUCTION EXAMPLE 142

In 1.5 ml of tetrahydrofuran was suspended 0.05 g of sodium hydride (60% in oil), to which 0.08 g of 2-butyn-1-ol was added, followed by stirring for 15 minutes. Then, 0.2 ml of a tetrahydrofuran solution containing 0.2 g of 4-chloro-6-(4-fluorobenzyl)pyrimidine was slowly added dropwise, followed by further stirring at room temperature for 2 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.22 g of 4-(2-butynyloxy)-6-(4-fluorobenzyl)pyrimidine (the present compound (143)).

¹H-NMR: 1.85 (t, 3H), 3.99 (s, 2H), 4.95 (q, 2H), 6.51 (s, 1H), 6.97-7.03 (m, 21), 7.19-7.23 (m, 21), 8.72 (s, 1H)

PRODUCTION EXAMPLE 143

To 2 ml of N,N-dimethylformamide were added 183 mg of 4-chloro-6-(2-butynyloxy)pyrimidine, 166 mg of potassium carbonate, and 73 mg of diethylamine, followed by stirring at a bath temperature of 50° C. for 4 hours. Then, 73 mg of diethylamine was further added, followed by stirring at a bath temperature of 50° C. for 5.5 hours. Then, 146 mg of diethylamine was further added, followed by stirring at a bath temperature of 40° C. for 6 hours. The reaction mixture was left for cooling to room temperature, diluted with ethyl acetate, and washed three times with an aqueous sodium chloride solution. The organic layers were dried over anhydrous magnesium sulfate and concentrated. The residue was subjected to silica gel thin layer chromatography to give 136 mg of 4-(2-butynyloxy)-6-(N,N-diethylamino)pyrimidine (the present compound (144)).

$^1$H-NMR: 1.17 (t, 6H), 1.88 (t, 3H), 3.47 (q, 4H), 4.91 (q, 2H), 5.75 (s, 1H), 8.30 (s, 1H)

PRODUCTION EXAMPLE 144

In 40 ml of tetrahydrofuran was suspended 4.61 g of potassium t-butoxide, to which 4.44 g of (2-fluorophenyl) acetonitrile was added under ice cooling. Then, a solution of 5.00 g of 4-chloro-6-(2-butynyloxy)pyrimidine in 20 ml of tetrahydrofuran was added at 0° C., followed by stirring at room temperature for 4 hours. The reaction mixture was then poured into a saturated aqueous ammonium chloride solution and extracted three times with chloroform. The chloroform layers were combined and washed with a saturated aqueous sodium chloride solution. The organic layer was dried over anhydrous magnesium sulfate and then concentrated. The residue was subjected to silica gel column chromatography to give 6.40 g of 4-α-cyano-2-fluorobenzyl)-6-(2-butynyloxy)pyrimidine (the present compound (145)).

$^1$H-NMR: 1.87 (t, 3H), 4.98 (q, 2H), 5.44 (s, 1H), 6.83 (s, 1H), 7.11-7.49 (m, 4H), 8.78 (s, 1H)

PRODUCTION EXAMPLE 145

To 2.2 ml of chloroform were added 0.29 ml of diisopropylethylamine, 0.2 g of 4-(2-butynyloxy)-6-chloropyrimidine, and 0.17 g of 2-fluorothiophenol, followed by stirring at room temperature for 7 hours. Then, a saturated aqueous ammonium chloride solution was poured into the reaction mixture, which was extracted three times with t-butyl methyl ether. The organic layers were combined, washed with water, dried over anhydrous magnesium sulfate, and then concentrated. The residue was subjected to silica gel column chromatography to give 0.07 g of 4-(2-butynyloxy)-6-(2-fluorophenylthio)pyrimidine (the present compound (146)).

$^1$H-NMR: 1.85 (t, 3H), 4.92 (q, 2H), 6.21 (s, 1H), 7.20-7.28 (m, 2H), 7.48-7.63 (m, 2H), 8.55 (s, 1H)

PRODUCTION EXAMPLE 146

In 1 ml of tetrahydrofuran was suspended 0.04 g of sodium hydride (60% in oil), to which 0.2 ml of a tetrahydrofuran solution containing 0.06 g of 3-pentyn-2-ol was slowly added dropwise under stirring at room temperature. The mixture was stirred at room temperature for 20 minutes, and 0.4 ml of a tetrahydrofuran solution containing 0.15 g of 4-chloro-6-(2,6-difluorobenzyl)pyrimidine was slowly added dropwise at room temperature, followed by stirring for 3 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.24 g of 4-(2,6-difluorobenzyl)-6-(1-methyl-2-butynyloxy)pyrimidine (the present compound (147)).

$^1$H-NMR: 1.56 (d, 3H), 1.82 (t, 3H), 4.11 (s, 2H), 5.75-5.79 (m, 1H), 6.47 (s, 1H), 6.87-6.96 (m, 2H), 7.19-7.29 (m, 2H), 8.72 (s, 1H)

PRODUCTION EXAMPLE 147

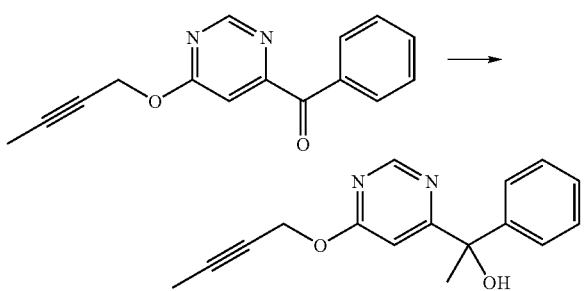

In 3.2 ml of tetrahydrofuran was dissolved 0.4 g of 6-(2-butynyloxy)-4-benzoylpyridmidine, to which 1.67 ml (1.14 mol/l diethyl ether solution) of methyl lithium was added dropwise at 0° C. After stirring at room temperature for 2 hours, the reaction mixture was poured into a saturated aqueous ammonium chloride solution and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.38 g of 4-(2-butynyloxy)-6-(α-hydroxy-α-methylbenzyl)pyrimidine (the present compound (148)).

$^1$H-NMR: 1.85 (t, 3H), 1.88 (s, 3H), 4.80 (s, 1H), 4.96 (q, 2H), 6.79 (s, 1H), 7.25 (t, 1H), 7.29 (t, 2H), 7.47 (d, 2H), 8.73 (s, 1H)

PRODUCTION EXAMPLE 148

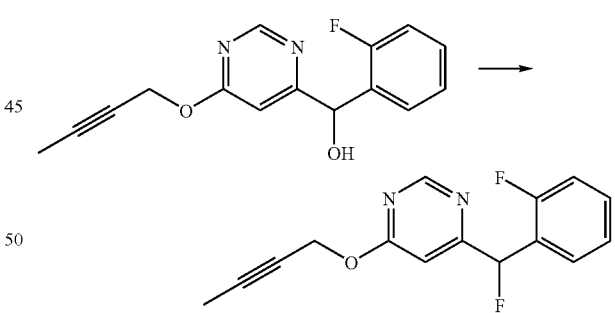

To a solution of 0.2 g of 6-(2-butynyloxy)-4-(α-hydroxy-2-fluorobenzyl)pyrimidine in 3.6 ml of acetonitrile was added dropwise a solution of 0.12 g of 2,2-difluoro-1,3-diemthylimidazolidine in 1 ml of acetonitrile, followed by stirring at room temperature for 4 hours. The reaction mixture was then poured into water and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.08 g of 4-(2-butynyloxy)-6-α-fluoro-2-fluorobenzyl)pyrimidine (the present compound (149)).

¹H-NMR: 1.88 (t, 3H), 5.00 (q, 2H), 6.64 (d, 1H), 7.06-7.41 (m, 5H, involving a singlet at 7.10), 8.73 (s, 1H)

PRODUCTION EXAMPLE 149

In 10 ml of N,N-dimethylformamide were dissolved 458 mg of 4-chloro-6-(2-fluorophenyl)pyrimidine and 231 mg of 3-butyn-2-ol, to which 132 mg of sodium hydride (60% in oil) was added, followed by stirring at room temperature for 10 hours. The reaction mixture was then poured into water and extracted three times with ethyl acetate. The organic layers were combined, washed with a saturated aqueous sodium chloride solution, dried over anhydrous magnesium sulfate, and then concentrated. The resulting residue was subjected to silica gel column chromatography to give 506 mg of 4-(2-fluorophenyl)-6-(1-methyl-2-propynyloxy)pyrimidine (the present compound (150)).

¹H-NMR: 1.68 (d, 3H), 2.49 (d, 1H), 5.89 (dq, 1H), 7.13-7.23 (m, 1H), 7.25-7.34 (m, 2H, involving a singlet at 7.30), 7.39-7.49 (m, 1H), 8.07-8.16 (m, 1H), 8.89 (s, 1H)

PRODUCTION EXAMPLE 150

In 10 ml of N,N-dimethylformamide were dissolved 449 mg of 4-chloro-6-(2-fluorophenyl)pyrimidine and 272 mg of 3-pentyn-2-ol, to which 130 mg of sodium hydride (60% in oil) was added, followed by stirring at room temperature for 8 hours. The reaction mixture was then poured into water and extracted three times with ethyl acetate. The organic layers were combined, washed with a saturated aqueous sodium chloride solution, dried over anhydrous magnesium sulfate, and then concentrated. The resulting residue was subjected to silica gel column chromatography to give 510 mg of 4-(2-fluorophenyl)-6-(1-methyl-2-butynyloxy)pyrimidine (the present compound (151)).

¹H-NMR: 1.63 (d, 3H), 2.32 (d, 3H), 5.87 (m, 1H), 7.03-7.21 (m, 1H), 7.25-7.32 (m, 2H, involving a singlet at 7.31), 7.39-7.49 (m, 1H), 8.07-8.16 (m, 1H), 8.88 (s, 1H)

PRODUCTION EXAMPLE 151

In 10 ml of N,N-dimethylformamide were dissolved 450 mg of 4-chloro-6-(2-fluorophenyl)pyrimidine and 227 mg of 3-butyn-1-ol, to which 130 mg of sodium hydride (60% in oil) was added, followed by stirring at room temperature for 12 hours. The reaction mixture was then poured into water and extracted three times with ethyl acetate. The organic layers were combined, washed with a saturated aqueous sodium chloride solution, dried over anhydrous magnesium sulfate, and then concentrated. The resulting residue was subjected to silica gel column chromatography to give 302 mg of 4-(2-fluorophenyl)-6-(3-butynyloxy)pyrimidine (the present compound (152)).

¹H-NMR: 2.06 (t, 1H), 2.72 (dt, 2H), 4.54 (t, 2H), 7.12-7.22 (m, 1H), 7.27 (s, 1H), 7.26-7.32 (m, 1H), 7.40-7.49 (m, 1H), 8.08-8.16 (m, 1H), 8.84 (s, 1H)

PRODUCTION EXAMPLE 152

In 10 ml of N,N-dimethylformamide were dissolved 457 mg of 4-chloro-6-(2-fluorophenyl)pyrimidine and 277 mg of 3-pentyn-1-ol, to which 132 mg of sodium hydride (60% in oil) was added, followed by stirring at room temperature for 8 hours. The reaction mixture was then poured into water and extracted three times with ethyl acetate. The organic layers were combined, washed with a saturated aqueous sodium chloride solution, dried over anhydrous magnesium sulfate, and then concentrated. The resulting residue was subjected to silica gel column chromatography to give 467 mg of 4-(2-fluorophenyl)-6-(3-pentynyloxy)pyrimidine (the present compound (153)).

¹H-NMR: 1.79 (t, 3H), 2.65 (m, 2H), 4.15 (t, 21), 7.01-7.20 (m, 1H), 7.23-7.30 (m, 1H), 7.38-7.48 (m, 1H), 7.27 (s, 1H), 8.07-8.16 (m, 1H), 8.83 (s, 1H)

PRODUCTION EXAMPLE 153

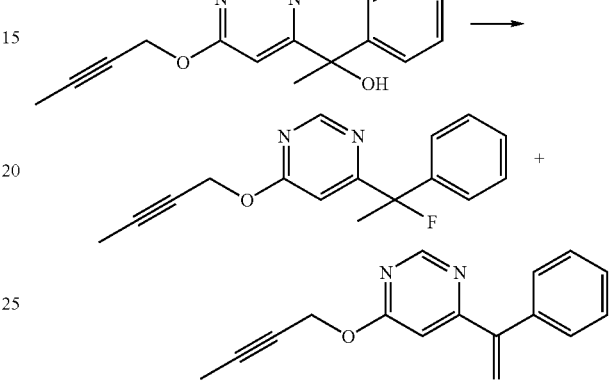

To a solution of 0.33 g of 6-(2-butynyloxy)-4-(α-hydroxy-α-methylbenzyl)pyrimidine in 4 ml of acetonitrile was added dropwise a solution of 0.2 g of 2,2-difluoro-1,3-dimethylimidazolidine in 2 ml of acetonitrile, followed by stirring at room temperature for 6 hours. The reaction mixture was then poured into water and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.20 g of 4-(2-butynyloxy)-6-α-fluoro-α-methylbenzyl)pyrimidine (the present compound (154)) and 0.09 g of 4-(2-butynyloxy)-6-(1-phenylvinyl)pyrimidine (the present compound (155)).

The present compound (154):
¹H-NMR: 1.85 (t, 3H), 2.05 (d, 3H), 4.97 (q, 2H), 7.07 (d, 1H), 7.25-7.36 (m, 3H), 7.50-7.53 (m, 2H), 8.73 (s, 1H)

The present compound (155):
¹H-NMR: 1.86 (t, 3H), 4.98 (q, 2H), 5.66 (d, 1H), 6.03 (d, 1H), 6.65 (s, 1H), 7.29-7.37 (m, 5H), 8.80 (s, 1H)

PRODUCTION EXAMPLE 154

To 2 ml of N,N-dimethylformamide were added 0.2 g of 4-chloro-6-(2-butynyloxy)pyrimidine, 0.23 g of potassium carbonate and 0.19 g of 2-chloro-5-fluorophenol, followed by stirring at 60° C. for 7 hours. The reaction mixture was then left for cooling to room temperature and poured into a saturated aqueous ammonium chloride solution, which was extracted three times with chloroform. The chloroform layers were combined and washed with diluted hydrochloric acid and then with water, and dried over anhydrous magnesium sulfate and then concentrated. The residue was subjected to silica gel column chromatography to give 0.30 g of 4-(2-butynyloxy)-6-(2-chloro-5-fluorophenoxy)pyrimidine (the present compound (156)).

¹H-NMR: 1.88 (t, 3H), 5.00 (q, 2H), 6.33 (s, 1H), 6.94-7.00 (m, 2H), 7.41-7.46 (m, 1H), 8.44 (s, 1H)

PRODUCTION EXAMPLE 155

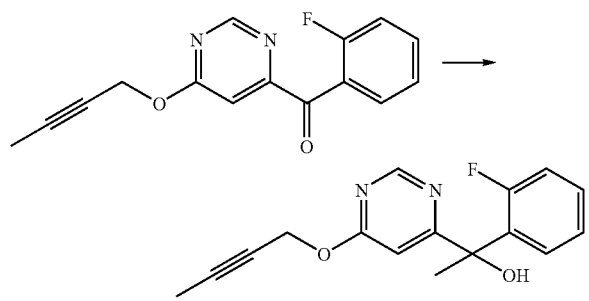

In 3.7 ml of tetrahydrofuran was dissolved 0.4 g of 6-(2-butynyloxy)pyrimidin-4-yl 2-fluorophenyl ketone, to which 3.6 ml (1.14 mol/l diethyl ether solution) of methyl lithium was added dropwise at −78° C. After stirring at −78° C. for 3 hours, the reaction mixture was poured into a saturated aqueous ammonium chloride solution and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 0.34 g of 4-(2-butynyloxy)-6-(α-hydroxy-α-methyl-2-fluorobenzyl)pyrimidine (the present compound (157)).

¹H-NMR: 1.86 (t, 3H), 1.91 (s, 3H), 4.85 (s, 1H), 4.98 (q, 2H), 6.88 (s, 1H), 6.95 (dd, 1H), 7.13-7.30 (m, 2H), 7.70 (td, 1H), 8.71 (s, 1H)

PRODUCTION EXAMPLE 156

Under an atmosphere of a nitrogen gas, 400 mg of sodium hydride was added to 20 ml of N,N-dimethylformamide, followed by ice cooling, to which an N,N-dimethylformamide (4 ml) solution of 861 mg of cyclopentyl alcohol was added dropwise, and the mixture was stirred for 1 hour. Under ice cooling, 1.49 g of 4,6-dichloropyrimidine was added, and the mixture was stirred at room temperature for 6 hours. The reaction mixture was then poured into water, which was extracted twice with t-butyl methyl ether and then washed three times with water. The organic layers were dried over anhydrous magnesium sulfate and concentrated to give 950 mg of the crude product.

Under an atmosphere of a nitrogen gas, 240 mg of sodium hydride was added to 10 ml of N,N-dimethylformamide, followed by ice cooling, to which an N,N-dimethylformamide (2 ml) solution of 421 mg of 2-butyn-1-ol was added dropwise, and the mixture was stirred at room temperature for 30 minutes. After ice cooling, an N,N-dimethylformamide (2 ml) solution of the crude product obtained above was added dropwise. The mixture was stirred at room temperature for 1 hour and then at a bath temperature of 50° C. for 4 hours. After left for cooling to room temperature, the reaction mixture was poured into water. The mixture was extracted three times with t-butyl methyl ether and then washed three times with water. The organic layers were dried over anhydrous magnesium sulfate and concentrated. The residue was subjected to silica gel thin layer chromatography to give 396 mg of 4-(2-butynyloxy)-6-(cyclopentyloxy)pyrimidine (the present compound (158)).

¹H-NMR: 1.55-2.05 (m, 11H), 4.94 (q, 2H), 5.35 (m, 1H), 6.05 (s, 1H), 8.43 (s, 1H)

PRODUCTION EXAMPLE 157

Under an atmosphere of a nitrogen gas, 240 mg of sodium hydride was added to 10 ml of N,N-dimethylformamide, followed by ice cooling, to which an N,N-dimethylformamide (2 ml) solution of 601 mg of cyclohexyl alcohol was added dropwise, and the mixture was stirred for 6 hours. Under ice cooling, 894 mg of 4,6-dichloropyrimidine was added, and the mixture was stirred at room temperature overnight. The reaction mixture was then poured into water, which was extracted twice with t-butyl methyl ether and then washed three times with water. The organic layers were dried over anhydrous magnesium sulfate and concentrated to give 450 mg of the crude product.

Under an atmosphere of a nitrogen gas, 160 mg of sodium hydride was added to 4 ml of N,N-dimethylformamide, followed by ice cooling, to which an N,N-dimethylformamide (2 ml) solution of 280 mg of 2-butyn-1-ol was added dropwise, and the mixture was stirred at room temperature for 1 hour. After ice cooling, an N,N-dimethylformamide (2 ml) solution of the crude product obtained above was added dropwise. After stirring at room temperature for 6 hours, the reaction mixture was poured into water. The mixture was extracted two times with t-butyl methyl ether and then washed four times with water. The organic layers were dried over anhydrous magnesium sulfate and concentrated. The residue was subjected to silica gel thin layer chromatography to give 50 mg of 4-(2-butynyloxy)-6-(cyclohexyl oxy)pyrimidine (the present compound (159)).

¹H-NMR: 1.20-1.65 (m, 6H), 1.77 (m, 2H), 1.87 (t, 3H), 1.96 (m, 2H), 4.94 (q, 2H), 5.01 (m, 1H), 6.05 (s, 1H), 8.42 (s, 1H)

PRODUCTION EXAMPLE 158

To 2 ml of N,N-dimethylformamide were added 0.2 g of 4-chloro-6-(2-butynyloxy)pyrimidine, 0.23 g of potassium carbonate, and 0.20 g of 2,6-dichloro-4-fluorophenol, followed by stirring at 80° C. for 7 hours. The reaction mixture was then left for cooling to room temperature and poured into a saturated aqueous ammonium chloride solution, which was extracted three times with chloroform. The chloroform layers were combined, washed with diluted hydrochloric acid and then with water, and dried over anhydrous magnesium sulfate and then concentrated. The residue was subjected to silica gel column chromatography to give 0.22 g of 4-(2-butynyloxy)-6-(2,6-dichloro-4-fluorophenoxy)pyrimidine (the present compound (160)).

¹H-NMR: 1.89 (t, 3H), 5.00 (q, 2H), 6.40 (s, 1H), 7.17 (d, 2H), 8.40 (s, 1H)

PRODUCTION EXAMPLE 159

In 10 ml of N,N-dimethylformamide were dissolved 255 mg of 4-chloro-2-methyl-6-(2,3-difluorophenyl)pyrimidine and 97 mg of 3-butyn-2-ol, to which 56 mg of sodium hydride (60% in oil) was added, followed by stirring at room temperature for 9 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 250 mg of 2-methyl-4-(2,3-difluorophenyl)-6-(1-methyl-2-propynyloxy)pyrimidine (the present compound (161)).

$^1$H-NMR: 1.67 (d, 3H), 2.48 (d, 1H), 2.69 (s, 3H), 5.94 (dq, 1H), 7.06 (s, 1H), 7.13-7.30 (m, 2H), 7.79-7.86 (m, 1H)

PRODUCTION EXAMPLE 160

In 10 ml of N,N-dimethylformamide were dissolved 401 mg of 4-chloro-2-methyl-6-(2,3-difluorophenyl)pyrimidine and 152 mg of 2-butyn-1-ol, to which 87 mg of sodium hydride (60% in oil) was added, followed by stirring at room temperature for 11 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 395 mg of 2-methyl-4-(2,3-difluorophenyl)-6-(2-butynyloxy)pyrimidine (the present compound (162)).

$^1$H-NMR: 1.90 (t, 3H), 2.68 (s, 3H), 5.02 (q, 2H), 7.08 (s, 1H), 7.14-7.30 (m, 2H), 7.78-7.87 (m, 1H)

PRODUCTION EXAMPLE 161

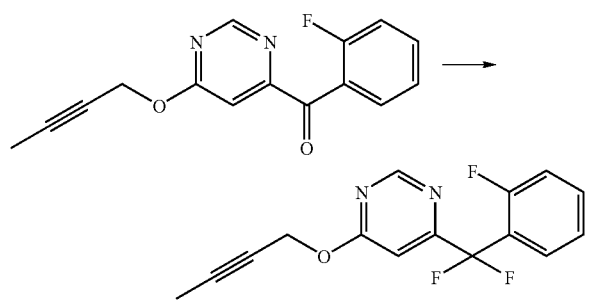

In 5.5 ml of acetonitrile was dissolved 0.4 g of 6-(2-butynyloxy)pyrimidin-4-yl 2-fluorophenyl ketone, to which a solution of 0.44 of 2,2-difluoro-1,3-dimethylimidazolidine in 2 ml of acetonitrile was added, followed by heating under reflux for 20 hours. The reaction mixture was then poured into water and extracted three times with ethyl acetate. The organic layers were combined and washed with a saturated aqueous sodium chloride solution, and the combined organic layer was dried over anhydrous magnesium sulfate and then concentrated. The resulting residue was subjected to silica gel column chromatography to give 0.23 g of 4-(2-butynyloxy)-6-(α,α-difluoro-2-fluorobenzyl)pyrimidine (the present compound (163)).

$^1$H-NMR: 1.88 (t, 3H), 5.03 (q, 2H), 7.06 (dd, 1H), 7.10-7.30 (m, 2H, involving a singlet at 7.26), 7.46 (qd, 1H), 7.77 (td, 1H), 8.78 (s, 1H)

PRODUCTION EXAMPLE 162

In 1.5 ml of tetrahydrofuran was suspended 0.04 g of sodium hydride (60% in oil), to which 0.5 ml of a tetrahydrofuran solution containing 0.06 g of 2-butyn-1-ol was slowly added dropwise under stirring at room temperature. The mixture was stirred at room temperature for 20 minutes, and 0.5 ml of a tetrahydrofuran solution containing 0.2 g of 4-chloro-6-(N-ethyl-N-(2,3-difluorophenyl)amino)pyrimidine was slowly added dropwise, followed by stirring at room temperature for 5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.16 g of 6-(2-butynyloxy)-4-(N-ethyl-N-(2,3-difluorophenyl)amino)pyrimidine (the present compound (164)).

$^1$H-NMR: 1.21 (t, 3H), 1.85 (t, 3H), 3.93 (q, 2H), 4.89 (q, 2H), 5.59 (s, 1H), 7.03-7.21 (m, 3H), 8.39 (s, 1H)

PRODUCTION EXAMPLE 163

In 3 ml of tetrahydrofuran was suspended 0.10 g of sodium hydride (60% in oil), to which 0.5 ml of a tetrahydrofuran solution containing 0.15 g of 2-butyn-1-ol was slowly added dropwise under stirring at room temperature. The mixture was stirred at room temperature for 20 minutes, and 0.5 ml of a tetrahydrofuran solution containing 0.43 g of 4-chloro-6-(N-ethyl-N-(3-fluorophenyl)amino)pyrimidine was slowly added dropwise, followed by stirring at room temperature for 6 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.2 g of 6-(2-butynyloxy)-4-(N-ethyl-N-(3-fluorophenyl)amino)pyrimidine (the present compound (165)).

$^1$H-NMR: 1.21 (t, 3H), 1.84 (t, 3H), 3.97 (q, 2H), 4.87 (q, 2H), 5.63 (s, 1H), 6.93-7.06 (m, 3H), 7.31-7.42 (m, 1H), 8.39 (s, 1H)

PRODUCTION EXAMPLE 164

In 1.2 ml of tetrahydrofuran was suspended 0.03 g of sodium hydride (60% in oil), to which 0.4 ml of a tetrahydrofuran solution containing 0.05 g of 2-butyn-1-ol was slowly added dropwise under stirring at room temperature. The mixture was stirred at room temperature for 20 minutes, and 0.4 ml of a tetrahydrofuran solution containing 0.16 g of 4-chloro-6-(2-chlorocyclohexyloxy)pyrimidine was slowly added dropwise, followed by stirring at 0° C. for 3 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.15 g of 6-(2-butynyloxy)-4-(2-chlorocyclohexyloxy)pyrimidine (the present compound (166)).

$^1$H-NMR: 1.32-1.64 (m, 3H), 1.75-1.82 (m, 3H), 1.87 (t, 3H), 2.18-2.29 (m, 2H), 3.98-4.04 (m, 1H), 4.95 (q, 2H), 5.08-5.22 (m, 1H), 6.12 (s, 1H), 8.43 (s, 1H)

PRODUCTION EXAMPLE 165

In 5 ml of N,N-dimethylformamide were dissolved 135 mg of 4-chloro-6-(2,3-difluorophenyl)pyrimidine and 60 mg of 3-pentyn-2-ol, to which 29 mg of sodium hydride (60% in oil) was added, followed by stirring at room temperature for 5 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 130 mg of 4-(2,3-difluorophenyl)-6-(1-methyl-2-butynyloxy)pyrimidine (the present compound (167)).

$^1$H-NMR: 1.64 (d, 3H), 1.86 (d, 3H), 5.76-5.90 (m, 1H), 7.14-7.33 (m, 3H, involving a singlet at 7.24), 7.81-7.91 (m, 1H), 8.90 (s, 1H)

PRODUCTION EXAMPLE 166

In 5 ml of tetrahydrofuran was suspended 0.15 g of sodium hydride (60% in oil), to which 1 ml of a tetrahydrofuran solution containing 0.20 g of 2-butyn-1-ol was slowly added dropwise under stirring at room temperature. The mixture was stirred at room temperature for 20 minutes, and 1 ml of a tetrahydrofuran solution containing 0.55 g of 4-chloro-6-(2-methylcyclohexyloxy(cis:trans=3:7))pyrimidine was slowly added dropwise, followed by stirring at room temperature for 3 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.36 g of 4-(2-butynyloxy)-6-(2-methylcyclohexyloxy)pyrimidine (the present compound (168)) as a mixture of its cis and trans forms.

Cis Form:
$^1$H-NMR: 0.93 (d, 3H), 1.51-1.98 (m, 12H, involving a triplet at 1.87), 4.95 (q, 2H), 5.15-5.19 (m, 1H), 6.09 (s, 1H), 8.42 (s, 1H)

Trans Form:
$^1$H-NMR: 0.93 (d, 3H), 1.10-1.37 (m, 4H), 1.63-1.83 (m, 4H), 1.87 (t, 3H), 2.08-2.14 (m, 1H), 4.69 (td, 1H), 4.94 (q, 2H), 6.06 (s, 1H), 8.42 (s, 1H)

PRODUCTION EXAMPLE 167

In 3.6 ml of tetrahydrofuran was suspended 0.09 g of sodium hydride (60% in oil), to which 0.6 ml of a tetrahydrofuran solution containing 0.14 g of 2-butyn-1-ol was slowly added dropwise under stirring at room temperature. The mixture was stirred at room temperature for 20 minutes, and 0.6 ml of a tetrahydrofuran solution containing 0.38 g of 4-chloro-6-(trans-2-methylcyclopentyloxy)pyrimidine was slowly added dropwise, followed by stirring at room temperature for 3 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.36 g of 4-(2-butynyloxy)-6-(trans-2-methylcyclopentyloxy)pyrimidine (the present compound (169)).

$^1$H-NMR: 1.04 (d, 3H), 1.20-1.27 (m, 1H), 1.66-2.17 (m, 9H, involving a triplet at 1.87), 4.90-4.95 (m, 3H), 6.06 (s, 1H), 8.43 (s, 1H)

PRODUCTION EXAMPLE 168

In 4 ml of tetrahydrofuran was suspended 0.10 g of sodium hydride (60% in oil), to which 0.6 ml of a tetrahydrofuran solution containing 0.15 g of 2-butyn-1-ol was slowly added dropwise under stirring at room temperature. The mixture was stirred at room temperature for 20 minutes, and 0.6 ml of a tetrahydrofuran solution containing 0.43 g of 4-chloro-6-(cycloheptyloxy)pyrimidine was slowly added dropwise, followed by stirring at room temperature for 3 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.52 g of 6-(2-butynyloxy)-4-(cycloheptyloxy)pyrimidine (the present compound (170)).

$^1$H-NMR: 1.48-1.80 (m, 10H), 1.88 (t, 3H), 1.98-2.06 (m, 2H), 4.93 (q, 2H), 5.10-5.22 (m, 1H), 6.04 (s, 1H), 8.42 (s, 1H)

PRODUCTION EXAMPLE 169

To a solution of 0.3 g of 4-(2-propynyloxy)-6-phenoxypyrimidine dissolved in 3 ml of ethanol were added 1.87 ml of 10% sodium hydroxide and 0.51 g of iodine at 0° C. The mixture was stirred at room temperature for 5 hours, and the alcohol was distilled out under reduced pressure. A saturated sodium thiosulfate solution was added to the residue, which was extracted three times with ethyl acetate. The organic layers were combined, dried over anhydrous magnesium sulfate, and then concentrated. The residue was subjected to silica gel column chromatography to give 0.12 g of 4-(3-iodo-2-propynyloxy)-6-phenoxypyrimidine (the present compound (171)).

$^1$H-NMR: 5.15 (s, 2H), 6.17 (s, 1H), 7.13 (d, 2H), 7.27 (t, 1H), 7.43 (t, 2H), 8.46 (s, 1H)

PRODUCTION EXAMPLE 170

In 1 ml of tetrahydrofuran was suspended 0.03 g of sodium hydride (60% in oil), to which 0.2 ml of a tetrahydrofuran solution containing 0.04 g of 2-butyn-1-ol was slowly added dropwise under stirring at room temperature. The mixture was stirred at room temperature for 20 minutes, and 0.2 ml of a tetrahydrofuran solution containing 0.12 g of 4-chloro-6-(cis-2-methylcyclohexyloxy)pyrimidine was slowly added dropwise, followed by stirring at room temperature for 5 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.10 g of 4-(2-butynyloxy)-6-(cis-2-methylcyclohexyloxy)pyrimidine (the present compound (172)).

$^1$H-NMR: 0.93 (d, 3H), 1.51-1.98 (m, 12H, involving a triplet at 1.87), 4.95 (q, 2H), 5.15-5.19 (m, 1H), 6.09 (s, 1H), 8.42 (s, 1H)

PRODUCTION EXAMPLE 171

In 5 ml of N,N-dimethylformamide were dissolved 246 mg of 4-chloro-6-(3-fluorophenyl)pyrimidine and 119 mg of 3-pentyn-2-ol, to which 57 mg of sodium hydride (60% in oil) was added, followed by stirring at room temperature for 8 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 200 mg of 4-(3-fluorophenyl)-6-(1-methyl-2-butynyloxy)pyrimidine (the present compound (173)).

$^1$H-NMR: 1.63 (d, 3H), 1.84 (d, 3H), 5.81-5.91 (m, 1H), 7.09 (s, 1H), 7.14-7.21 (m, 1H), 7.40-7.51 (m, 1H), 7.73-7.83 (m, 2H), 8.85 (s, 1H)

PRODUCTION EXAMPLE 172

In 10 ml of N,N-dimethylformamide were dissolved 344 mg of 4-chloro-6-(4-fluorophenyl)pyrimidine and 166 mg of 3-pentyn-2-ol, to which 166 mg of sodium hydride (60% in oil) was added, followed by stirring at room temperature for 10 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 205 mg of 4-(4-fluorophenyl)-6-(1-methyl-2-butynyloxy)pyrimidine (the present compound (174)).

$^1$H-NMR: 1.62 (d, 3H), 1.84 (d, 3H), 5.80-5.91 (m, 1H), 7.07 (s, 1H), 7.12-7.22 (m, 2H), 8.00-8.09 (m, 2H), 8.83 (s, 1H)

PRODUCTION EXAMPLE 173

In 1.6 ml of tetrahydrofuran was suspended 0.04 g of sodium hydride (60% in oil), to which 0.4 ml of a tetrahydrofuran solution containing 0.06 g of 2-butyn-1-ol was slowly added dropwise under stirring at room temperature. The mixture was stirred at room temperature for 20 minutes, and 0.4 ml of a tetrahydrofuran solution containing 0.18 g of 4-chloro-6-(trans-2-methylcyclohexyloxy)pyrimidine was slowly added dropwise, followed by stirring at room temperature for 6 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.14 g of 6-(2-butynyloxy)-4-(trans-2-methylcyclohexyloxy)pyrimidine (the present compound (175)).

$^1$H-NMR: 0.93 (d, 3H), 1.10-1.37 (m, 4H), 1.63-1.83 (m, 4H), 1.87 (t, 3H), 2.08-2.14 (m, 1H), 4.69 (td, 1H), 4.94 (q, 2H), 6.06 (s, 1H), 8.42 (s, 1H)

PRODUCTION EXAMPLE 174

Under an atmosphere of a nitrogen gas, 192 mg of sodium hydride was added to 10 ml of tetrahydrofuran, followed by ice cooling, to which an tetrahydrofuran (4 ml) solution of 280 mg of 2-butyn-1-ol was added dropwise, and the mixture was stirred at room temperature for 1 hour. Under ice cooling, an tetrahydrofuran (4 ml) solution of 778 mg of 4-(2-butynyloxy)-6-(3,3-dimethyl-1-butynyl)pyrimidine was added dropwise. The mixture was stirred at room temperature for 4 hours and then poured into water. The mixture was extracted with t-butyl methyl ether and then washed three times with water. And the organic layers were dried over sodium sulfate and concentrated. The residue was subjected to silica gel thin layer chromatography to give 560 mg of 4-(2-butynyloxy)-6-(3,3-dimethyl-1-ethynyl)pyrimidine (the present compound (176)).

$^1$H-NMR: 1.34 (s, 9H), 1.87 (t, 3H), 4.97 (q, 2H), 6.78 (s, 1H), 8.70 (s, 1

PRODUCTION EXAMPLE 175

To 0.5 ml of ethanol were added 0.3 g of 4,5-dichloro-6-(2-butynyloxy)pyrimidine and 0.48 g of N-ethylpropylamine, followed by heating under reflux for 8 hours. The reaction mixture was then left for cooling to room temperature and concentrated under reduced pressure. The residue was subjected to silica gel column chromatography to give 0.15 g of 5-choloro-4-(N-ethylpropylamino)-6-(2-butynyloxy)pyrimidine (the present compound (177)).

$^1$H-NMR: 0.91 (t, 3H), 1.22 (t, 3H), 1.67 (dt, 2H), 1.87 (t, 3H), 3.50 (t, 2H), 3.63 (q, 2H), 4.98 (q, 2H), 8.16 (s, 1H)

PRODUCTION EXAMPLE 176

In 5.4 ml of chloroform was dissolved 0.62 g of 4-chloro-6-(2-hydroxycyclohexyloxy)pyrimidine (mixture of cis-form and trans-form), to which 1.09 g of (dimethylamino) sulfur trifluoride was slowly added dropwise under stirring at room temperature, followed by further stirring at room temperature for 1 hour. The reaction mixture was then poured into water and extracted three times with t-butyl ethyl ether. The organic layers were combined, washed with a saturated aqueous sodium hydrogen carbonate, brine, and dried over anhydrous magnesium sulfate, and then concentrated. The residue was used for the next steps without purification.

In 2 ml of tetrahydrofuran was suspended 0.05 g of sodium hydride (60% in oil), to which 0.5 ml of a tetrahydrofuran solution containing 0.08 g of 2-butyn-1-ol was slowly added dropwise with stirring at room temperature. The mixture was stirred at room temperature for 20 minutes, to which 1 ml of a tetrahydrofuran solution containing the mixture of the crude product was slowly added dropwise, followed by further stirring at room temperature for 1 hour. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.14 g of 4-(2-butynyloxy)-6-(2-fluorocyclohexyloxy)pyrimidine (the present compound (178)).

$^1$H-NMR: 1.32-1.46 (m, 2H), 1.59-1.94 (m, 7H, involving a triplet at 1.87), 2.18-2.21 (m, 2H), 4.45-4.70 (m, 1H), 4.95 (q, 2H), 5.17-5.27 (m, 1H), 6.12 (s, 1H), 8.43 (s, 1H) with peaks due to the minor isomer at 6.18 (s), 8.48 (s)

PRODUCTION EXAMPLE 177

To 2 ml of N,N-dimethylformamide were added 0.1 g of 4-chloro-6-(2-butynyloxy)-5-fluoropyrimidine, 0.1 g of potassium carbonate, and 0.06 g of phenol, followed by stirring at 80° C. for 2 hours. The reaction mixture was left for cooling to room temperature and poured into a saturated aqueous ammonium chloride solution, which was extracted three times with t-butyl methyl ether. The organic layers were combined, washed with brine, dried over anhydrous magnesium sulfate, and then concentrated. The residue was subjected to silica gel column chromatography to give 0.12 g of 4-(2-butynyloxy)-5-fluoro-6-phenoxypyrimidine (the present compound (179)).

$^1$H-NMR: 1.88 (t, 3H), 5.07 (q, 2H), 7.17 (d, 2H), 7.27 (t, 1H), 7.43 (t, 2H), 8.15 (s, 1H)

PRODUCTION EXAMPLE 178

To 2 ml of N,N-dimethylformamide were added 0.1 g of 4-chloro-6-(2-butynyloxy)-5-fluoropyrimidine, 0.1 g of potassium carbonate, and 0.08 g of 2,3-difluorophenol, followed by stirring at 80° C. for 2 hours. The reaction mixture was left for cooling to room temperature and poured into a saturated aqueous ammonium chloride solution, which was extracted three times with t-butyl methyl ether.

The organic layers were combined, washed with brine, dried over anhydrous magnesium sulfate, and then concentrated. The residue was subjected to silica gel column chromatography to give 0.12 g of 4-(2-butynyloxy)-6-(2,3-difluorophenoxy)-5-fluoropyrimidine (the present compound (180)).

$^1$H-NMR: 1.88 (t, 3H), 5.08 (q, 2H), 7.02-7.15 (m, 3H), 8.12 (s, 1H)

PRODUCTION EXAMPLE 179

In 4 ml of tetrahydrofuran was suspended 0.16 g of sodium hydride (60% in oil), to which 0.5 ml of a tetrahydrofuran solution containing 0.23 g of 2-butyn-1-ol was slowly added dropwise with stirring at room temperature. The mixture was stirred at room temperature for 20 minutes, to which 1.5 ml of a tetrahydrofuran solution containing 0.72 g of 4-choloro-6-(2,3-dimethylcyclohexyloxy)pyrimidine (mixture of isomers) was slowly added dropwise at 0° C., followed by further stirring at room temperature for 3 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.67 g of 4-(2-butynyloxy)-6-(2,3-dimethylcyclohexyloxy)pyrimidine (the present compound (181)).

$^1$H-NMR: 0.83-2.26 (m, 17H, involving a triplet at 1.87), 4.67-4.77 (m, 1H), 4.94 (q, 2H), 6.07 (s, 1H), 8.42 (s, 1H) with peaks due to the minor isomers at 4.99-5.11 (m)

PRODUCTION EXAMPLE 180

In 2 ml of tetrahydrofuran was suspended 0.08 g of sodium hydride (60% in oil), to which 0.5 ml of a tetrahydrofuran solution containing 0.14 g of 2-butyn-1-ol was slowly added dropwise with stirring at room temperature. The mixture was stirred at room temperature for 20 minutes, to which 1.5 ml of a tetrahydrofuran solution containing 0.31 g of 4-choloro-6-(3-methylcyclohexyloxy)pyrimidine (mixture of cis-form and trans-form) was slowly added dropwise at 0° C., followed by further stirring at room temperature for 3 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.26 g of 4-(2-butynyloxy)-6-(3-methylcyclohexyloxy)pyrimidine (the present compound (182)).

$^1$H-NMR: 0.84-2.12 (m, 15H), 4.93-5.02 (m, 3H), 6.05 (s, 1H), 8.42 (s, 1H) with peaks due to the minor isomer at 5.31-5.34 (m), 6.07 (s)

PRODUCTION EXAMPLE 181

To 2 ml of N,N-dimethylformamide were added 0.1 g of 4-chloro-6-(2-butynyloxy)-5-fluoropyrimidine, 0.1 g of potassium carbonate, and 0.07 g of 2-fluorophenol, followed by stirring at 80° C. for 3 hours. The reaction mixture was left for cooling to room temperature and poured into a saturated aqueous ammonium chloride solution, which was extracted three times with t-butyl methyl ether. The organic layers were combined, washed with brine, dried over anhydrous magnesium sulfate, and then concentrated. The residue was subjected to silica gel column chromatography to give 0.11 g of 4-(2-butynyloxy)-6-(2-fluorophenoxy)-5-fluoropyrimidine (the present compound (183)).

$^1$H-NMR: 1.88 (t, 3H), 5.07 (q, 2H), 7.17-7.28 (m, 4H), 8.13 (s, 1H)

PRODUCTION EXAMPLE 182

To 2 ml of N,N-dimethylformamide were added 0.1 g of 4-chloro-6-(2-butynyloxy)-5-fluoropyrimidine, 0.1 g of potassium carbonate, and 0.08 g of 2-chlorophenol, followed by stirring at 60° C. for 1 hour. The reaction mixture was left for cooling to room temperature and poured into a saturated aqueous ammonium chloride solution, which was extracted three times with t-butyl methyl ether. The organic layers were combined, washed with brine, dried over anhydrous magnesium sulfate, and then concentrated. The residue was subjected to silica gel column chromatography to give 0.12 g of 4-(2-butynyloxy)-6-(2-chlorophenoxy)-5-fluoropyrimidine (the present compound (184)).

$^1$H-NMR: 1.88 (t, 3H), 5.07 (q, 2H), 7.22-7.37 (m, 3H), 7.50 (d, 1H), 8.12 (s, 1H)

PRODUCTION EXAMPLE 183

To 0.5 ml of ethanol ware added 0.1 g of 4-(2-butynyloxy)-6-chloro-5-fluoropyrimidine and 0.11 g of N-ethylpropylamine, followed by heating under reflux for 10 hours. The reaction mixture was then left for cooling to room temperature and concentrated under reduced pressure. The residue was added water and extracted three times with t-butyl methyl ether. The organic layers were combined, dried over anhydrous magnesium sulfate, and then concentrated. The residue was subjected to silica gel column chromatography to give 0.15 g of 6-(2-butynyloxy)-4-(N-ethylpropylamino)-5-fluoropyrimidine (the present compound (185)).

$^1$H-NMR: 0.92 (t, 3H), 1.21 (t, 3H), 1.65 (dt, 2H), 1.87 (t, 3H), 3.45 (t, 2H), 3.57 (q, 2H), 4.97 (q, 2H), 8.01(s, 1H)

PRODUCTION EXAMPLE 184

In 2 ml of tetrahydrofuran was suspended 0.11 g of sodium hydride (60% in oil), to which 0.5 ml of a tetrahydrofuran solution containing 0.14 g of 2-butyn-1-ol was slowly added dropwise with stirring at room temperature. The mixture was stirred at room temperature for 20 minutes, to which 1 ml of a tetrahydrofuran solution containing 0.5 g of 4,5-dicholoro-6-(N-ethyl-N-phenylamino)pyrimidine was slowly added dropwise at room temperature, followed by further stirring at room temperature for 4 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.38 g of 6-(2-butynyloxy)-5-chloro-4-(N-ethyl-N-phenylamino)pyrimidine (the present compound (186)).

$^1$H-NMR: 1.22 (t, 3H), 1.86 (t, 3H), 4.03 (q, 2H), 4.99 (q, 2H), 7.04-7.35 (m, 5H), 8.35 (s, 1H)

PRODUCTION EXAMPLE 185

In 1.5 ml of tetrahydrofuran was suspended 0.08 g of sodium hydride (60% in oil) to which 0.5 ml of a tetrahydrofuran solution containing 0.13 g of 2-butyn-1-ol was slowly added dropwise with stirring at room temperature.

The mixture was stirred at room temperature for 20 minutes, to which 1.5 ml of a tetrahydrofuran solution containing 0.37 g of 4-choloro-6-(cis-4-methylcyclohexyloxy)pyrimidine was slowly added dropwise at room temperature, followed by further stirring at room temperature for 4 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.36 g of 4-(2-butynyloxy)-6-(cis-4-methylcyclohexyloxy)pyrimidine (the present compound (187)).

$^1$H-NMR: 0.91 (d, 3H), 1.27-1.66 (m, 7H), 1.86-2.01 (m, 5H involving a triplet at 1.88), 4.94 (q, 2H), 5.18-5.24 (m, 1H), 6.08 (s, 1H), 8.42 (s, 1H)

PRODUCTION EXAMPLE 186

In 1.5 ml of tetrahydrofuran was suspended 0.09 g of sodium hydride (60% in oil), to which 0.5 ml of a tetrahydrofuran solution containing 0.13 g of 2-butyn-1-ol was slowly added dropwise with stirring at room temperature. The mixture was stirred at room temperature for 20 minutes, to which 1.5 ml of a tetrahydrofuran solution containing 0.37 g of 4-choloro-6-(trans-4-methylcyclohexyloxy)pyrimidine was slowly added dropwise at room temperature, followed by further stirring at room temperature for 2 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.43 g of 4-(2-butynyloxy)-6-(trans-4-methylcyclohexyloxy)pyrimidine (the present compound (188)).

$^1$H-NMR: 0.91 (d, 3H), 1.06-1.16 (m, 2H), 1.37-1.51 (m, 3H), 1.75-1.79 (m, 2H), 1.87 (t, 3H), 2.07-2.13 (m, 2H), 4.90-4.97 (m, 3H), 6.04 (s, 1H), 8.41 (s, 1H)

PRODUCTION EXAMPLE 187

In 1.5 ml of tetrahydrofuran was suspended 0.09 g of sodium hydride (60% in oil), to which 0.5 ml of a tetrahydrofuran solution containing 0.13 g of 2-butyn-1-ol was slowly added dropwise with stirring at room temperature. The mixture was stirred at room temperature for 20 minutes, to which 1.5 ml of a tetrahydrofuran solution containing 0.5 g of 4-choloro-6-(cis-2-trimetylsilanyloxycyclohexyloxy) pyrimidine was slowly added dropwise at room temperature, followed by further stirring at room temperature for 3 hours. The reaction mixture was then poured into 10% hydrochloric acid at room temperature, followed by further stirring for 10 minutes. Then the mixture was extracted three times with t-butyl methyl ether. The organic layers were combined, washed with brine, dried over anhydrous magnesium sulfate, and then concentrated. The residue was subjected to silica gel column chromatography to give 0.25 g of 4-(2-butynyloxy)-6-(cis-2-hydroxycyclohexyloxy)pyrimidine (the present compound (189)).

$^1$H-NMR: 1.37-1.44 (m, 2H), 1.65-2.01 (m, 9H, involving a triplet at 1.87), 2.98 (bs, 1H), 3.96-3.99 (m, 1H), 4.95 (q, 2H), 5.18-5.23 (m, 1H), 6.12 (s, 1H), 8.40 (s, 1H)

PRODUCTION EXAMPLE 188

To 2 ml of N,N-dimethylformamide were added 0.1 g of 4-chloro-6-(2-butynyloxy)-5-fluoropyrimidine, 0.1 g of potassium carbonate, and 0.08 g of 2,6-difluorophenol, followed by stirring at 60° C. for 4 hours. The reaction mixture was left for cooling to room temperature and poured into a saturated aqueous ammonium chloride solution, which was extracted three times with t-butyl methyl ether. The organic layers were combined, washed with brine, dried over anhydrous magnesium sulfate, and then concentrated. The residue was subjected to silica gel column chromatography to give 0.1 g of 4-(2-butynyloxy)-6-(2,6-difluorophenoxy)-5-fluoropyrimidine (the present compound (190)).

$^1$H-NMR: 1.88 (t, 3H), 5.08 (q, 2H), 7.00-7.07 (m, 2H), 7.18-7.27 (m, 1H), 8.12 (s, 1)

PRODUCTION EXAMPLE 189

In 3 ml of tetrahydrofuran was suspended 0.1 g of sodium hydride (60% in oil), to which 0.5 ml of a tetrahydrofuran solution containing 0.15 g of 2-butyn-1-ol was slowly added dropwise with stirring at room temperature. The mixture was stirred at room temperature for 20 minutes, to which 1 ml of a tetrahydrofuran solution containing 0.46 g of 4-choloro-6-(2-fluorobenzyl)-5-fluoropyrimidine was slowly added dropwise at 0° C., followed by further stirring at 0° C. for 2 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.46 g of 4-(2-butynyloxy)-6-(2-fluorobenzyl)-5-fluoropyrimidine (the present compound (191)).

$^1$H-NMR: 1.86 (t, 3H), 4.16 (s, 2H), 5.04 (q, 2H), 6.99-7.10 (m, 2H), 7.18-7.30 (m, 2H), 8.46 (s, 1H)

The present compounds described in the above production examples are shown with their compound numbers in the following tables.

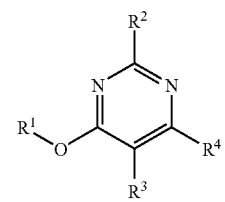

| Compd. No. | $R^1$ | $R^4$ | $R^2$ | $R^3$ |
|---|---|---|---|---|
| 1 | 2-butynyl | 2-butynyloxy | H | H |
| 2 | 2-propynyl | 2-butynyloxy | H | H |
| 3 | 2-pentynyl | 2-pentynyloxy | H | H |
| 4 | 2-butynyl | 4-chloro-2-fluorophenoxy | H | H |
| 5 | 2-pentynyl | 2-propynyloxy | H | H |
| 6 | 2-pentynyl | 2-butynyloxy | H | H |
| 7 | 4,4-dimethyl-2-pentynyl | 2-butynyloxy | H | H |
| 8 | 4,4-dimethyl-2-pentynyl | 4,4-dimethyl-2-pentynyloxy | H | H |
| 9 | 2-butynyl | phenoxy | H | H |
| 10 | 2-butynyl | 3,4-difluorophenoxy | H | H |
| 11 | 2-propynyl | 1-methyl-2-propynyloxy | H | H |
| 12 | 2-propynyl | 3-butynyloxy | H | H |
| 13 | 2-propynyl | benzyloxy | H | H |
| 14 | 2-propynyl | 4-chlorophenoxy | H | H |

-continued

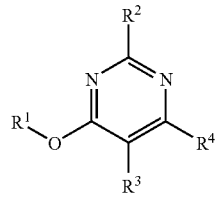

| Compd. No. | R¹ | R⁴ | R² | R³ |
|---|---|---|---|---|
| 15 | 2-propynyl | 3-chlorophenoxy | H | H |
| 16 | 2-butynyl | 2-chloro-4-fluorophenoxy | H | H |
| 17 | 2-propynyl | 3-trifluoromethylphenoxy | H | H |
| 18 | 2-propynyl | 2-trifluoromethylphenoxy | H | H |
| 19 | 2-propynyl | 2-chlorophenoxy | H | H |
| 20 | 2-propynyl | 4-trifluoromethylphenoxy | H | H |
| 21 | 2-propynyl | 2,6-difluorophenoxy | H | H |
| 22 | 2-propynyl | 2,4-dichlorophenoxy | H | H |
| 23 | 2-propynyl | 3,4-dichlorophenoxy | H | H |
| 24 | 2-propynyl | 3,5-dichlorophenoxy | H | H |
| 25 | 2-propynyl | 2,5-dichlorophenoxy | H | H |
| 26 | 2-propynyl | 2,3-dichlorophenoxy | H | H |
| 27 | 2-propynyl | 2-methylphenoxy | H | H |
| 28 | 2-propynyl | 4-methylphenoxy | H | H |
| 29 | 2-propynyl | 3-methylphenoxy | H | H |
| 30 | 2-propynyl | 3-methoxyphenoxy | H | H |
| 31 | 2-propynyl | 4-methoxyphenoxy | H | H |
| 32 | 2-propynyl | 2-methoxyphenoxy | H | H |
| 33 | 2-butynyl | 2,6-difluorophenoxy | H | H |
| 34 | 2-propynyl | 2-fluorophenoxy | H | H |
| 35 | 2-propynyl | 4-fluorophenoxy | H | H |
| 36 | 2-propynyl | 3-fluorophenoxy | H | H |
| 37 | 2-propynyl | phenyl | H | H |
| 38 | 2-butynyl | phenyl | H | H |
| 39 | 2-butynyl | 2,3-difluorophenoxy | H | H |
| 40 | 2-butynyl | 3-cyanophenoxy | H | H |
| 41 | 2-butynyl | 4-cyanophenoxy | H | H |
| 42 | 2-butynyl | 2-cyanophenoxy | H | H |
| 43 | 2-butynyl | 2,5-difluorophenoxy | H | H |
| 44 | 2-butynyl | 2,4-difluorophenoxy | H | H |
| 45 | 2-butynyl | 2,4,6-trifluorophenoxy | H | H |
| 46 | 2-butynyl | 2,3,6-trifluorophenoxy | H | H |
| 47 | 2-butynyl | 2-chloro-4,6-difluorophenoxy | H | H |
| 48 | 2-butynyl | 4-fluoro-3-trifluoromethyl-phenoxy | H | H |
| 49 | 2-butynyl | 3-trifluoromethoxyphenoxy | H | H |
| 50 | 2-butynyl | 4-trifluoromethoxyphenoxy | H | H |
| 51 | 2-butynyl | phenoxy | H | H |
| 52 | 2-propynyl | 2-propynyloxy | H | H |
| 53 | 2-butynyl | phenylamino | H | H |
| 54 | 2-propynyl | 2-fluorophenyl | H | H |
| 55 | 2-butynyl | 2-fluorophenyl | H | H |
| 56 | 2-propynyl | 3-fluorophenyl | H | H |
| 57 | 2-butynyl | 3-fluorophenyl | H | H |
| 58 | 2-propynyl | 4-fluorophenyl | H | H |
| 59 | 2-butynyl | 4-fluorophenyl | H | H |
| 60 | 2-pentynyl | 2,3-difluorophenoxy | H | H |
| 61 | 2-butynyl | 3-fluorophenoxy | H | H |
| 62 | 2-butynyl | 4-fluorophenoxy | H | H |
| 63 | 2-butynyl | 2-fluorophenoxy | H | H |
| 64 | 2-butynyl | 2,3-(methylenedioxy)phenoxy | H | H |
| 65 | 2-butynyl | 2-fluoro-4-nitrophenoxy | H | H |
| 66 | 2-butynyl | N-(2,3-difluorophenyl)-N-methylamino | H | H |
| 67 | 2-butynyl | 2,3-dimethylphenoxy | H | H |
| 68 | 2-butynyl | 2,6-difluorobenzyloxy | H | H |
| 69 | 2-butynyl | 3-phenylphenoxy | H | H |
| 70 | 2-butynyl | 3-phenoxyphenoxy | H | H |
| 71 | 2-butynyl | 3-acetylphenoxy | H | H |
| 72 | 2-butynyl | α-cyano-2,3-difluorobenzyl | H | H |
| 73 | 2-butynyl | 2,3-difluorophenylamino | H | H |
| 74 | 2-butynyl | α-cyanobenzyl | H | H |
| 75 | 2-butynyl | benzoyl | H | H |
| 76 | 2-butynyl | 2,3-difluorobenzyloxy | H | H |
| 77 | 2-propynyl | phenyl | CH₃ | H |
| 78 | 2-butynyl | phenyl | CH₃ | H |

-continued

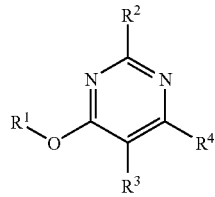

| Compd. No. | R¹ | R⁴ | R² | R³ |
|---|---|---|---|---|
| 79 | 2-butynyl | N-(2,3-difluorophenyl)-N-methoxymethylamino | H | H |
| 80 | 2-butynyl | 2,6-difluorobenzyl | H | H |
| 81 | 2-butynyl | N-phenyl-N-ethylamino | H | H |
| 82 | 2-propynyl | 2,3-difluorophenyl | H | H |
| 83 | 2-butynyl | 2,3-difluorophenyl | H | H |
| 84 | 2-butynyl | α-cyano-2-chloro-6-fluoro-benzyl | H | H |
| 85 | 2-butynyl | N-(2,3-difluorophenyl)-N-cyanomethylamino | H | H |
| 86 | 2-pentynyl | 2-fluorophenyl | H | H |
| 87 | 2-butynyl | 2,6-difluorophenyl | H | H |
| 88 | 2-butynyl | 2-fluorobenzyl | H | H |
| 89 | 2-butynyl | 2-chlorobenzyl | H | H |
| 90 | 2-butynyl | 2,3,5,6-tetrafluorophenoxy | H | H |
| 91 | 2-butynyl | benzyl | H | H |
| 92 | 2-butynyl | 2-methylbenzyl | H | H |
| 93 | 2-butynyl | N-methyl-N-phenylamino | H | H |
| 94 | 2-butynyl | 1-phenylethyl | H | H |
| 95 | 2-butynyl | 2-trifluorobenzyl | H | H |
| 96 | 2-butynyl | 2,3-difluorobenzyl | H | H |
| 97 | 2-butynyl | phenylthio | H | H |
| 98 | 2-butynyl | N-propyl-N-phenylamino | H | H |
| 99 | 2-butynyl | 2,4-difluorobenzyl | H | H |
| 100 | 2-butynyl | 3-fluorobenzyl | H | H |
| 101 | 2-butynyl | 2-chloro-6-fluorobenzyl | H | H |
| 102 | 2-butynyl | 3-chloro-2-fluorobenzyl | H | H |
| 103 | 2-butynyl | 2-bromobenzyl | H | H |
| 104 | 2-butynyl | N-ethyl-N-methylamino | H | H |
| 105 | 2-butynyl | N-ethyl-N-isopropylamino | H | H |
| 106 | 2-butynyl | isopropylamino | H | H |
| 107 | 2-butynyl | N-(2-butynyl)-N-isopropylamino | H | H |
| 108 | 2-butynyl | ethylamino | H | H |
| 109 | 2-butynyl | N-ethyl-N-(2-butynyl)amino | H | H |
| 110 | 2-butynyl | N-ethyl-N-(2-propenyl)amino | H | H |
| 111 | 2-butynyl | 2,2,3,3,3-pentafluoropropyl amino | H | H |
| 112 | 2-butynyl | N-(2,2,3,3,3-pentafluoropropyl)-N-ethylamino | H | H |
| 113 | 2-butynyl | di-n-propylamino | H | H |
| 114 | 2-butynyl | 2,2,2-trifluoroethylamino | H | H |
| 115 | 2-butynyl | N-ethyl-N-(2,2,2-trifluoroethyl)amino | H | H |
| 116 | 2-butynyl | 1-(3-fluorophenyl)ethyl | H | H |
| 117 | 2-pentynyl | 2,3-difluorophenyl | H | H |
| 118 | 2-heptynyl | 2,3-difluorophenyl | H | H |
| 119 | 4,4-dimethyl-2-pentynyl | 2,3-difluorophenyl | H | H |
| 120 | 2-butynyl | 1-(2-fluorophenyl)ethyl | H | H |
| 121 | 2-butynyl | 2-chloro-5-methyl-6-fluoro-benzyl | H | H |
| 122 | 2-butynyl | α-methoxybenzyl | H | H |
| 123 | 2-butynyl | α-hydroxybenzyl | H | H |
| 124 | 2-butynyl | α-fluorobenzyl | H | H |
| 125 | 2-butynyl | α-methoxyiminobenzyl (A) | H | H |
| 126 | 2-butynyl | α-methoxyiminobenzyl (B) | H | H |
| 127 | 2-butynyl | α-ethoxyiminobenzyl (A) | H | H |
| 128 | 2-butynyl | α-ethoxyiminobenzyl (B) | H | H |
| 129 | 2-butynyl | N-benzyl-N-ethylamino | H | H |
| 130 | 2-butynyl | 2-chloro-3,6-difluorobenzyl | H | H |
| 131 | 2-butynyl | α-isopropoxyiminobenzyl (A) | H | H |
| 132 | 2-butynyl | α-isopropoxyiminobenzyl (B) | H | H |
| 133 | 2-butynyl | benzylamino | H | H |
| 134 | 1-methyl-propynyl | 2,3-difluorophenyl | H | H |

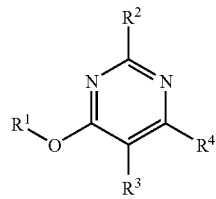

| Compd. No. | R¹ | R⁴ | R² | R³ |
|---|---|---|---|---|
| 135 | 4-fluoro-2-butynyl | 2,3-difluorophenyl | H | H |
| 136 | 3-chloro-2-propynyl | 2,3-difluorophenyl | H | H |
| 137 | 2-butynyl | α-methoxymethoxybenzyl | H | H |
| 138 | 2-butynyl | α-ethoxybenzyl | H | H |
| 139 | 2-butynyl | α-acetoxybenzyl | H | H |
| 140 | 2-butynyl | α-propionyloxybenzyl | H | H |
| 141 | 2-butynyl | α-isobutyryloxybenzyl | H | H |
| 142 | 2-butynyl | 2-chlorophenylthio | H | H |
| 143 | 2-butynyl | 4-fluorobenzyl | H | H |
| 144 | 2-butynyl | diethylamino | H | H |
| 145 | 2-butynyl | α-cyano-2-fluorobenzyl | H | H |
| 146 | 2-butynyl | 2-fluorophenylthio | H | H |
| 147 | 1-methyl-2-butynyl | 2,6-difluorobenzyl | H | H |
| 148 | 2-butynyl | α-hydroxy-α-methylbenzyl | H | H |
| 149 | 2-butynyl | α-fluoro-2-fluorobenzyl | H | H |
| 150 | 1-methyl-2-propynyl | 2-fluorophenyl | H | H |
| 151 | 1-methyl-2-butynyl | 2-fluorophenyl | H | H |
| 152 | 3-butynyl | 2-fluorophenyl | H | H |
| 153 | 3-pentynyl | 2-fluorophenyl | H | H |
| 154 | 2-butynyl | α-fluoro-α-methylbenzyl | H | H |
| 155 | 2-butynyl | 1-phenylvinyl | H | H |
| 156 | 2-butynyl | 2-chloro-5-fluorophenoxy | H | H |
| 157 | 2-butynyl | α-hydroxy-α-methyl-2-fluorobenzyl | H | H |
| 158 | 2-butynyl | cyclopentyloxy | H | H |
| 159 | 2-butynyl | cyclohexyloxy | H | H |
| 160 | 2-butynyl | 2,6-dichloro-4-fluorophenoxy | H | H |
| 161 | 1-methyl-2-propynyl | 2,3-difluorophenyl | CH₃ | H |
| 162 | 2-butynyl | 2,3-difluorophenyl | CH₃ | H |
| 163 | 2-butynyl | α,α-difluoro-2-fluorobenzyl | H | H |
| 164 | 2-butynyl | N-ethyl-N-2,3-difluorophenyl-amino | H | H |
| 165 | 2-butynyl | N-ethyl-N-3-fluorophenyl-amino | H | H |
| 166 | 2-butynyl | 2-chlorocyclohexyloxy | H | H |
| 167 | 1-methyl-2-butynyl | 2,3-difluorophenyl | H | H |
| 168 | 2-butynyl | 2-methylcyclohexyloxy | H | H |
| 169 | 2-butynyl | 2-methylcyclopentyloxy | H | H |
| 170 | 2-butynyl | cycloheptyloxy | H | H |
| 171 | 3-iodo-2-propynyl | phenoxy | H | H |
| 172 | 2-butynyl | cis-2-methylcyclohexyloxy | H | H |
| 173 | 1-methyl-2-butynyl | 3-fluorophenyl | H | H |
| 174 | 1-methyl-2-butynyl | 4-fluorophenyl | H | H |
| 175 | 2-butynyl | trans-2-methylcyclohexyloxy | H | H |
| 176 | 2-butynyl | 3,3-dimethyl-1-butynyl | H | H |
| 177 | 2-butynyl | N-ethyl-N-n-propyl-amino | H | Cl |
| 178 | 2-butynyl | 2-fluorocyclohexyloxy | H | H |
| 179 | 2-butynyl | phenoxy | H | F |
| 180 | 2-butynyl | 2,3-difluorophenoxy | H | F |
| 181 | 2-butynyl | 2,3-dimethylcyclohexyloxy | H | H |
| 182 | 2-butynyl | 3-methylcyclohexyloxy | H | H |
| 183 | 2-butynyl | 2-fluorophenoxy | H | F |
| 184 | 2-butynyl | 2-chlorophenoxy | H | F |
| 185 | 2-butynyl | N-ethyl-N-n-propyl-amino | H | F |
| 186 | 2-butynyl | N-ethyl-N-phenyl-amino | H | Cl |
| 187 | 2-butynyl | cis-4-methylcyclohexyloxy | H | H |

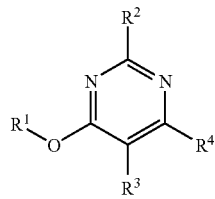

| Compd. No. | R¹ | R⁴ | R² | R³ |
|---|---|---|---|---|
| 188 | 2-butynyl | trans-4-methylcyclohexyloxy | H | H |
| 189 | 2-butynyl | 2-hydroxycyclohexyloxy | H | H |
| 190 | 2-butynyl | 2,6-difluorophenoxy | H | F |
| 191 | 2-butynyl | 2-fluorobenzyl | H | F |

The following will describe the reference production examples for the intermediates used in the production of the present compounds.

REFERENCE PRODUCTION EXAMPLE 1

In 12 ml of tetrahydrofuran was suspended 0.61 g of sodium hydride (60% in oil), to which 4 ml of a tetrahydrofuran solution containing 0.57 g of 2-propyn-1-ol was slowly added dropwise with stirring at room temperature. The mixture was stirred at room temperature for 20 minutes and then cooled to 0° C., to which 4 ml of a tetrahydrofuran solution containing 1.5 g of 4,6-dichloropyrimidine was slowly added dropwise, followed by further stirring for 2.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 1.61 g of 4-chloro-6-(2-propynyloxy)pyrimidine.

4-Chloro-6-(2-propynyloxy)pyrimidine

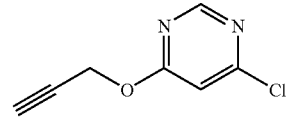

¹H-NMR: 2.58 (t, 1H), 5.06 (d, 2H), 6.86 (s, 1H), 8.63 (s, 1H)

REFERENCE PRODUCTION EXAMPLE 2

In 24 ml of tetrahydrofuran was suspended 1.05 g of sodium hydride (60% in oil), to which 8 ml of a tetrahydrofuran solution containing 1.42 g of 2-butyn-1-ol was slowly added dropwise with stirring at room temperature. The mixture was stirred at room temperature for 20 minutes and then cooled to 0° C., to which 8 ml of a tetrahydrofuran solution containing 3 g of 4,6-dichloropyrimidine was slowly added dropwise, followed by further stirring at 0° C. for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 3.16 g of 4-chloro-6-(2-butynyloxy)pyrimidine, m.p.: 43.5° C.

4-Chloro-6-(2-butynyloxy)pyrimidine

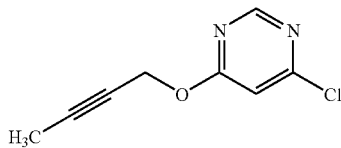

REFERENCE PRODUCTION EXAMPLE 3

In 3 ml of tetrahydrofuran was suspended 0.12 g of sodium hydride (60% in oil), to which 0.5 ml of a tetrahydrofuran solution containing 0.22 g of benzyl alcohol was slowly added dropwise with stirring at room temperature. The mixture was stirred at room temperature for 20 minutes and then cooled to 0° C., to which 0.5 ml of a tetrahydrofuran solution containing 0.3 g of 4,6-dichloropyrimidine was slowly added dropwise, followed by stirring at 0° C. for 1.5 hours and then further stirring at room temperature for 4.5 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.43 g of 4-chloro-6-benzyloxypyrimidine.

4-Chloro-6-benzyloxypyrimidine

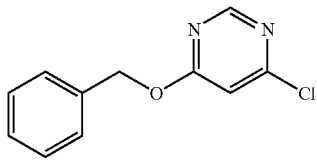

$^1$H-NMR: 5.38 (s, 2H), 6.73 (s, 1H), 7.29-7.39 (m, 5H), 8.52 (s, 1H)

REFERENCE PRODUCTION EXAMPLE 4

A reaction vessel was charged with 0.17 g of tetrakistriphenylphosphine palladium, 0.91 g of phenylboronic acid, and 3.53 g of barium hydroxide, to which 44 ml of 1,2-dimethoxyethane, 8 ml of water, and 1.11 g of 4,6-dichloropyrimidine were added, followed by stirring at 80° C. under an atmosphere of a nitrogen gas for 6 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.51 g of 4-chloro-6-phenylpyrimidine, m.p.: 101.3° C.

4-Chloro-6-phenylpyrimidine

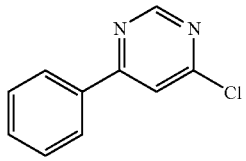

REFERENCE PRODUCTION EXAMPLE 5

A reaction vessel was charged with 0.258 g of tetrakistriphenylphosphine palladium, 1.143 g of 2-fluorophenylboronic acid, and 3.153 g of tripotassium phosphate n-hydrate, to which 36 ml of 1,2-dimethoxyethane, 9 ml of water, and 1.106 g of 4,6-dichloropyrimidine were added, followed by stirring at 80° C. under an atmosphere of a nitrogen gas for 9 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.519 g of 4-chloro-6-(2-fluorophenyl)pyrimidine.

4-Chloro-6-(2-fluorophenyl)pyrimidine

$^1$H-NMR: 7.17-7.37 (m, 2H), 7.46-7.56 (m, 1H), 7.90 (s, 1H), 8.19 (dt, 1H), 9.07 (s, 1H)

REFERENCE PRODUCTION EXAMPLE 6

A reaction vessel was charged with 0.303 g of tetrakistriphenylphosphine palladium, 1.344 g of 3-fluorophenylboronic acid, and 3.707 g of tripotassium phosphate n-hydrate, to which 36 ml of 1,2-dimethoxyethane, 9 ml of water, and 1.301 g of 4,6-dichloropyrimidine were added, followed by stirring at 80° C. under an atmosphere of a nitrogen gas for 7 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.45 g of 4-chloro-6-(3-fluorophenyl)pyrimidine.

4-Chloro-6-(3-fluorophenyl)pyrimidine

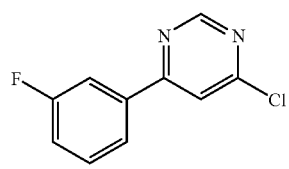

$^1$H-NMR: 7.19-7.29 (m, 1H), 7.45-7.55 (m, 1H), 7.73 (s, 1H), 7.79-7.89 (m, 2H), 9.04 (s, 1H)

REFERENCE PRODUCTION EXAMPLE 7

A reaction vessel was charged with 0.255 g of tetrakistriphenylphosphine palladium, 1.132 g of 4-fluorophenylboronic acid, and 3.122 g of tripotassium phosphate n-hydrate, to which 36 ml of 1,2-dimethoxyethane, 9 ml of water, and 1.095 g of 4,6-dichloropyrimidine were added, followed by stirring at 80° C. under an atmosphere of a nitrogen gas for 8 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.399 g of 4-chloro-6-(4-fluorophenyl)pyrimidine.

4-Chloro-6-(4-fluorophenyl)pyrimidine

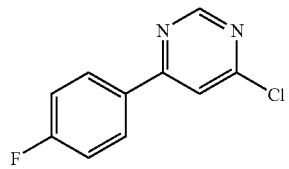

$^1$H-NMR: 7.20 (t, 2H), 7.71 (s, 1H), 8.07-8.12 (m, 2H), 9.01 (s, 1H)

REFERENCE PRODUCTION EXAMPLE 8

To 14 ml of ethanol were added 2.2 g of 4,6-dichloropyrimidine and 2.3 g of 2,3-difluoroaniline, followed by heating under reflux for 6 hours. The reaction mixture was then left for cooling to room temperature and concentrated under reduced pressure. The residue was recrystallized from ethyl acetate to give 3.5 g of 4-chloro-6-(2,3-difluoroanilino)pyrimidine.

4-Chloro-6-(2,3-difluoroanilino)pyrimidine

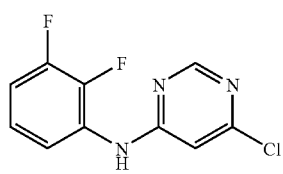

$^1$H-NMR (DMSO-d$_6$): 6.89 (s, 1H), 7.20-7.24 (m, 2H), 7.60-7.81 (m, 1H), 8.47 (s, 1H), 9.95 (bs, 1H)

REFERENCE PRODUCTION EXAMPLE 9

In 2 ml of tetrahydrofuran was suspended 0.07 g of sodium hydride (60% in oil), to which 0.6 ml of a tetrahydrofuran solution containing 0.3 g of 4-chloro-6-(2,3-difluoroanilino)pyrimidine was slowly added dropwise with stirring at room temperature. The mixture was stirred at room temperature for 20 minutes, to which 0.6 ml of a tetrahydrofuran solution containing 0.2 g of iodomethane was slowly added dropwise, followed by further stirring for 8 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.16 g of 4-chloro-6-(N-methyl-N-2,3-difluorophenylamino)pyrimidine.

4-Chloro-6-(N-methyl-N-(2,3-difluorophenyl)amino)pyrimidine

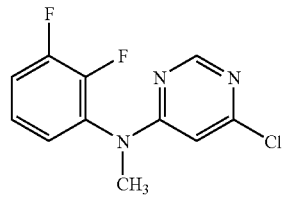

$^1$H-NMR: 3.46 (s, 3H), 6.28 (s, 1H), 7.05-7.26 (m, 3H), 8.49 (s, 1H)

REFERENCE PRODUCTION EXAMPLE 10

To 2 ml of chloroform were added 0.3 g of 4-chloro-6-(2,3-difluoroanilino)pyrimidine and 0.65 ml of diisopropylethylamine, to which 0.6 ml of a chloroform solution containing 0.15 g of chloromethyl methyl ether was slowly added dropwise. After stirring for 8 hours, the reaction mixture was poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.12 g of 4-(N-methoxymethyl-N-2,3-difluorophenylamino)-6-chloropyrimidine.

4-(N-Methoxymethyl-N-2,3-difluorophenylamino)-6-chloropyrimidine

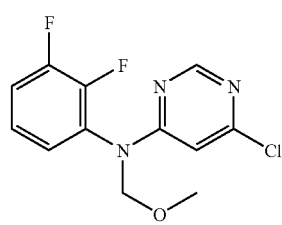

$^1$H-NMR: 3.44 (s, 3H), 5.31 (s, 2H), 6.36 (s, 1H), 7.14-7.29 (m, 3H), 8.52 (s, 1H)

REFERENCE PRODUCTION EXAMPLE 11

In 2 ml of tetrahydrofuran was suspended 0.07 g of sodium hydride (60% in oil), to which 0.6 ml of a tetrahydrofuran solution containing 0.3 g of 4-chloro-6-(2,3-difluoroanilino)pyrimidine was slowly added dropwise with stirring at room temperature. The mixture was stirred at room temperature for 20 minutes, to which 0.6 ml of a tetrahydrofuran solution containing 0.18 g of bromoacetonitrile was slowly added dropwise, followed by further stirring for 8 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 0.24 g of 4-chloro-6-(N-cyanomethyl-N-(2,3-difluorophenyl)amino)pyrimidine.

4-Chloro-6-(N-cyanomethyl-N-(2,3-difluorophenyl)amino)pyrimidine

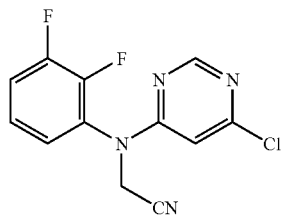

REFERENCE PRODUCTION EXAMPLE 12

$^1$H-NMR: 4.85 (bs, 2H), 6.29 (s, 1H), 7.21-7.39 (m, 3H), 8.64 (s, 1H) To 10 ml of an ethanol solution of 1.5 g of 4,6-dichloropyrimidine was slowly added 0.78 g of sodium thiomethoxide at 0° C., followed by stirring at 0° C. for 7 hours. A saturated aqueous ammonium chloride solution was added to the reaction mixture and concentrated under reduced pressure. The residue was extracted three times with chloroform. The chloroform layers were combined, washed with water, dried over anhydrous magnesium sulfate, and then concentrated. The residue was subjected to silica gel column chromatography to give 1.1 g of 4-chloro-6-methylthiopyrimidine.

4-Chloro-6-methylthiopyrimidine

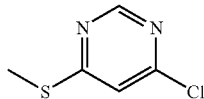

$^1$H-NMR: 2.58 (s, 3H), 7.21 (s, 1H), 8.72 (s, 1H)

REFERENCE PRODUCTION EXAMPLE 13

In 10 ml of tetrahydrofuran was suspended 0.41 g of sodium hydride (60% in oil), to which 2 ml of a tetrahydrofuran solution containing 0.58 g of 2-butyn-1-ol was slowly added dropwise with stirring at room temperature. The mixture was stirred at room temperature for 20 minutes, to which 2 ml of a tetrahydrofuran solution containing 1.1 g of 4-chloro-6-methylthiopyrimidine was slowly added dropwise, followed by further stirring for 4 hours. The reaction mixture was then poured into a saturated aqueous ammonium chloride solution and extracted three times with chloroform. The chloroform layers were combined, washed with water, dried over anhydrous magnesium sulfate, and then concentrated. The residue was subjected to silica gel column chromatography to give 1.3 g of 4-(2-butynyloxy)-6-methylthiopyrimidine.

4-(2-butynyloxy)-6-methylthiopyrimidine

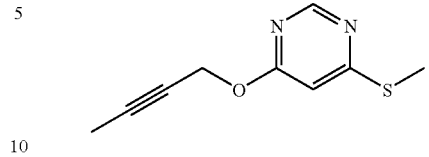

$^1$H-NMR: 1.87 (t, 3H), 2.52 (s, 3H), 4.59 (q, 2H), 6.60 (s, 1H), 8.57 (s, 1H)

REFERENCE PRODUCTION EXAMPLE 14

To 14 ml of chloroform were added 4-(2-butynyloxy)-6-methylthiopyrimidine and 3.5 g of m-chloroperbenzoic acid (>65%), followed by stirring at 0° C. for 10 hours. The reaction mixture was then poured into a saturated aqueous sodium thiosulfate solution and extracted three times with chloroform. The chloroform layers were combined, washed with water, dried over anhydrous magnesium sulfate, and then concentrated. The residue was subjected to silica gel column chromatography to give 1.4 g of 4-(2-butynyloxy)-6-methanesulfonylpyrimidine.

4-(2-Butynyloxy)-6-methanesulfonylpyrimidine

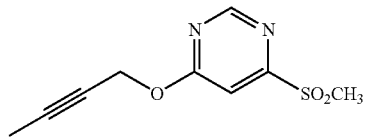

$^1$H-NMR: 1.88 (t, 3H), 3.23 (s, 3H), 5.07 (q, 2H), 7.46 (s, 1H), 8.92 (s, 1H)

REFERENCE PRODUCTION EXAMPLE 15

A reaction vessel was charged with 9.84 g of 2-methyl-4,6-dihydroxy-pyrimidine, 29.46 g of phosphorus oxychloride, and 20.18 g of diisopropylethylamine under ice cooling, followed by stirring for 30 minutes and further stirring at 80° C. for 3 hours. The reaction mixture was then left for cooling to room temperature and poured into a saturated aqueous sodium bicarbonate, which was extracted with ethyl acetate. The organic layer was washed with a saturated aqueous sodium bicarbonate and a saturated aqueous sodium chloride solution, dried over anhydrous magnesium sulfate, and then concentrated. The residue was subjected to silica gel column chromatography to give 9.5 g of 2-methyl-4,6-dichloropyrimidine.

2-Methyl-4,6-dichloropyrimidine

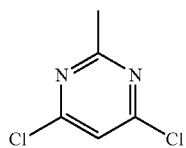

$^1$H-NMR: 2.71 (s, 3H), 7.26 (s, 1H)

REFERENCE PRODUCTION EXAMPLE 16

A reaction vessel was charged with 2.19 g of tetrakistriphenylphosphine palladium, 847 mg of phenylboronic acid, and 2.99 g of barium hydroxide, to which 40 ml of 1,2-dimethoxyethane, 7 ml of water, and 1.01 g of 2-methyl-4,6-dichloropyrimidine were added, followed by stirring at 80° C. under an atmosphere of a nitrogen gas for 6 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.65 g of 2-methyl-4-chloro-6-phenylpyrimidine.

2-Methyl-4-chloro-6-phenylpyrimidine

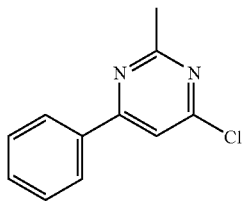

$^1$H-NMR: 1.58 (s, 3H), 7.47-7.58 (m, 4H, involving a singlet at 7.56), 8.02-8.11 (m, 2H)

REFERENCE PRODUCTION EXAMPLE 17

In 30 ml of tetrahydrofuran was suspended 5.24 g of potassium t-butoxide, to which 2.63 g of phenylacetonitrile and 3.0 g of 4-chloro-6-methylthiopyrimidine, followed by stirring at 0° C. for 4 hours. The reaction mixture was then poured into a saturated aqueous ammonium chloride solution and extracted three times with ethyl acetate. The organic layers were combined and washed with a saturated aqueous sodium chloride solution, and the combined organic layer was dried over anhydrous magnesium sulfate and then concentrated. The residue was subjected to silica gel column chromatography to give 3.67 g of 4-(α-cyanobenzyl)-6-methylthiopyrimidine.

4-(α-Cyanobenzyl)-6-methylthiopyrimidine

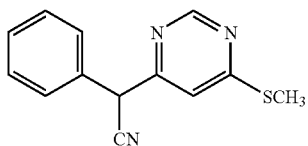

$^1$H-NMR: 2.55 (s, 3H), 5.13 (s, 1H), 7.25 (s, 1H), 7.35-7.45 (m, 5H), 8.89 (s, 1H)

REFERENCE PRODUCTION EXAMPLE 18

To 2 ml of ethanol was suspended 0.3 g of 6-methylthio-4-benzoylpyrimidine, to which 0.07 g of sodium borohydride was added, followed by stirring at 0° C. for 4 hours. The reaction mixture was then poured into a saturated aqueous ammonium chloride solution and extracted three times with ethyl acetate. The organic layers were combined and washed with a saturated aqueous sodium chloride solution, and the combined organic layer was dried over anhydrous magnesium sulfate and then concentrated to give 6-methylthio-4-(α-hydroxybenzyl)pyrimidine.

6-Methylthio-4-(α-hydroxybenzyl)pyrimidine

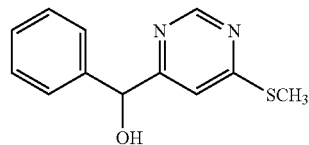

$^1$H-NMR: 2.52 (s, 3H), 4.64 (bs, 1H), 5.60 (s, 1H), 7.16 (s, 1H), 7.28-7.35 (m, 5H), 8.81 (s, 1H)

REFERENCE PRODUCTION EXAMPLE 19

In 3 ml of tetrahydrofuran was suspended 0.08 g of sodium hydride (60% in oil), to which 6-methylthio-4-(α-hydroxylbenzyl)pyrimidine dissolved in 0.3 ml of tetrahydrofuran was added. The mixture was stirred at 0° C. for 15 minutes, to which 0.28 g of iodomethane was added dropwise at room temperature, followed by stirring at the same temperature for 30 minutes. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.17 g of 6-methylthio-4-(α-methoxybenzyl)pyrimidine.

6-Methylthio-4-(α-methoxybenzyl)pyrimidine

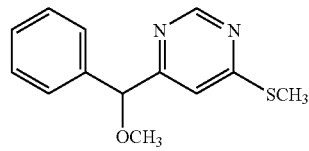

$^1$H-NMR: 2.54 (s, 3H), 3.40 (s, 3H), 5.19 (s, 1H), 7.25-7.41 (m, 5H), 7.45 (s, 1H), 8.82 (s, 1H)

REFERENCE PRODUCTION EXAMPLE 20

To 2 ml of chloroform were added 0.17 g of 6-methylthio-4-(α-methoxybenzyl)pyrimidine and 0.43 g of m-chloroperbenzoic acid (>65%), followed by stirring at 0° C. for 10 hours. The reaction mixture was then poured into a saturated aqueous sodium thiosulfate solution and extracted three times with chloroform. The chloroform layers were combined, washed with water, dried over anhydrous magnesium sulfate, and then concentrated. The residue was subjected to silica gel column chromatography to give 0.2 g of 4-(α-methoxybenzyl)-6-methanesulfonylpyrimidine.

4-(α-Methoxybenzyl)-6-methanesulfonylpyrimidine

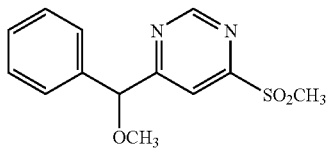

$^1$H-NMR: 3.25 (s, 3H), 3.45 (s, 3H), 5.39 (s, 1H), 7.31-7.44 (m, 5H), 8.31 (s, 1H), 9.21 (s, 1H)

REFERENCE PRODUCTION EXAMPLE 21

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 1.7 g of benzyl bromide dissolved in 20 ml of tetrahydrofuran was slowly added with heating under reflux, followed by stirring for 20 minutes. (The solution thus obtained is referred to as solution A). In 10 ml of tetrahydrofuran were suspended 1.5 g of 4,6-dichloropyrimidine and 0.1 g of dichlorobistriphenylphosphine palladium, to which the above solution A was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.83 g of 4-chloro-6-benzylpyrimidine.

4-Chloro-6-benzylpyrimidine

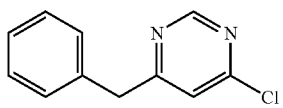

$^1$H-NMR: 4.11 (s, 2H), 7.13 (s, 1H), 7.24-7.38 (m, 5H), 8.91 (s, 1H)

REFERENCE PRODUCTION EXAMPLE 22

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 1.9 g of 2-fluorobenzyl bromide dissolved in 20 ml of tetrahydrofuran was slowly added with heating under reflux, followed by stirring for 20 minutes. (The solution thus obtained is referred to as solution B). In 10 ml of tetrahydrofuran were suspended 1.5 g of 4,6-dichloropyrimidine and 0.1 g of dichlorobistriphenylphosphine palladium, to which the above solution B was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.63 g of 4-chloro-6-(2-fluorobenzyl)pyrimidine.

4-Chloro-6-(2-fluorobenzyl)pyrimidine

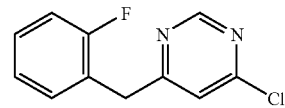

$^1$H-NMR: 4.05 (s, 2H), 6.70-7.08 (m, 3H), 7.17-7.23 (m, 2H), 8.81 (s, 1H)

REFERENCE PRODUCTION EXAMPLE 23

A reaction vessel was charged with [1,1'-bis(diphenylphosphino)ferrocene dichloropalladium]methylene chloride complex, 1.007 g of 2,6-difluorophenylboronic acid, and 2.707 g of tripotassium phosphate n-hydrate, to which 16 ml of 1,2-dimethoxyethane, 4 ml of water, and 0.95 g of 4,6-dichloropyrimidine were added, followed by stirring at 80° C. under an atmosphere of a nitrogen gas for 5 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 0.241 g of 4-chloro-6-(2,6-difluorophenyl)pyrimidine.

4-Chloro-6-(2,6-difluorophenyl)pyrimidine

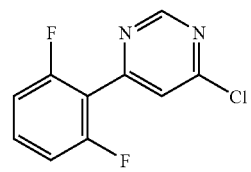

$^1$H-NMR: 7.06 (t, 2H), 7.49-7.53 (m, 1H), 7.58 (s, 1H), 9.13 (s, 1H)

REFERENCE PRODUCTION EXAMPLE 24

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.1 g of 2-chlorobenzyl bromide dissolved in 20 ml of tetrahydrofuran was slowly added with heating under reflux, followed by stirring for 20 minutes. (The solution thus obtained is referred to as solution C). In 10 ml of tetrahydrofuran were suspended 1.5 g of 4,6-dichloropyrimidine and 0.1 g of dichlorobistriphenylphosphine palladium, to which the above solution C was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.84 g of 4-chloro-6-(2-chlorobenzyl)pyrimidine.

4-Chloro-6-(2-chlorobenzyl)pyrimidine

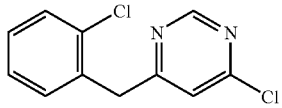

$^1$H-NMR: 4.25 (s, 2H), 7.10 (s, 1H), 7.26-7.33 (m, 3H), 7.41-7.44 (m, 1H), 8.91 (s, 1H)

REFERENCE PRODUCTION EXAMPLE 25

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 1.9 g of 2-methylbenzyl bromide dissolved in 20 ml of tetrahydrofuran was slowly added with heating under reflux, followed by stirring for 20 minutes. (The solution thus obtained is referred to as solution D). In 10 ml of tetrahydrofuran were suspended 1.5 g of 4,6-dichloropyrimidine and 0.1 g of dichlorobistriphenylphosphine palladium, to which the above solution D was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.55 g of 4-chloro-6-(2-methylbenzyl)pyrimidine.

4-Chloro-6-(2-methylbenzyl)pyrimidine

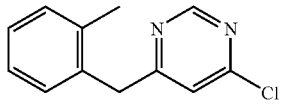

$^1$H-NMR: 2.24 (s, 3H), 4.13 (s, 2H), 6.98 (s, 1H), 7.18-7.23 (m, 4H), 8.91 (s, 1H)

REFERENCE PRODUCTION EXAMPLE 26

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.5 g of 2,6-difluorobenzyl bromide dissolved in 20 ml of tetrahydrofuran was slowly added with heating under reflux, followed by stirring for 20 minutes. (The solution thus obtained is referred to as solution E). In 10 ml of tetrahydrofuran were suspended 1.5 g of 4,6-dichloropyrimidine and 0.1 g of dichlorobistriphenylphosphine palladium, to which the above solution D was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.69 g of 4-chloro-6-(2,6-difluorobenzyl) pyrimidine.

4-Chloro-6-(2,6-difluorobenzyl)pyrimidine

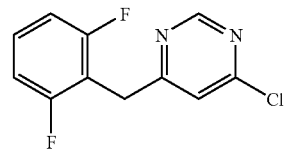

$^1$H-NMR: 4.18 (s, 2H), 6.92-6.99 (m, 2H), 7.17 (s, 1H), 7.24-7.34 (m, 1H), 8.90 (s, 1H)

REFERENCE PRODUCTION EXAMPLE 27

A reaction vessel was charged with 2.03 g of tetrakistriphenylphosphine palladium, 5.55 g of 2,3-difluorophenylboronic acid, and 14.9 g of tripotassium phosphate n-hydrate, to which 120 ml of 1,2-dimethoxyethane, 30 ml of water, and 5.20 g of 4,6-dichloropyrimidine were added, followed by stirring at 80° C. under an atmosphere of a nitrogen gas for 12 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 3.32 g of 4-chloro-6-(2,3-difluorophenyl)pyrimidine.

4-Chloro-6-(2,3-difluorophenyl)pyrimidine

$^1$H-NMR: 7.19-7.51 (m, 2H), 7.85-7.98 (m, 2H, involving a singlet at 7.89), 9.08 (s, 1H)

REFERENCE PRODUCTION EXAMPLE 28

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.4 g of 2-trifluoromethylbenzyl bromide dissolved in 20 ml of tetrahydrofuran was slowly added with heating under reflux, followed by stirring for 20 minutes. (The solution thus obtained is referred to as solution F). In 10 ml of tetrahydrofuran were suspended 1.5 g of 4,6-dichloropyrimidine and 0.1 g of dichlorobistriphenylphosphine palladium, to which the above solution F was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.92 g of 4-chloro-6-(2-trifluoromethylbenzyl)pyrimidine.

4-Chloro-6-(2-trifluoromethylbenzyl)pyrimidine

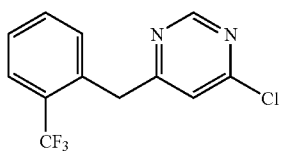

$^1$H-NMR: 4.32 (s, 2H), 7.02 (s, 1H), 7.38-7.45 (m, 2H), 7.55 (t, 1H), 7.72 (d, 1H), 8.92 (s, 1H)

REFERENCE PRODUCTION EXAMPLE 29

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.1 g of 2,3-difluorobenzyl bromide dissolved in 20 ml of tetrahydrofuran was slowly added with heating under reflux, followed by stirring for 20 minutes. (The solution thus obtained is referred to as solution G). In 10 ml of tetrahydrofuran were suspended 1.5 g of 4,6-dichloropyrimidine and 0.1 g of dichlorobistriphenylphosphine palladium, to which the above solution G was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.93 g of 4-chloro-6-(2,3-difluorobenzyl)pyrimidine.

4-Chloro-6-(2,3-difluorobenzyl)pyrimidine

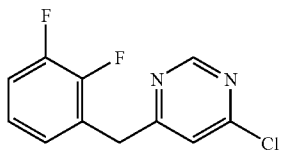

$^1$H-NMR: 4.16 (s, 2H), 6.95-7.16 (m, 3H), 7.20 (s, 1H), 8.92 (s, 1H)

REFERENCE PRODUCTION EXAMPLE 30

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.1 g of 2,4-difluorobenzyl bromide dissolved in 20 ml of tetrahydrofuran was slowly added with heating under reflux, followed by stirring for 20 minutes. (The solution thus obtained is referred to as solution H). In 10 ml of tetrahydrofuran were suspended 1.5 g of 4,6-dichloropyrimidine and 0.1 g of dichlorobistriphenylphosphine palladium, to which the above solution H was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.95 g of 4-chloro-6-(2,4-difluorobenzyl)pyrimidine.

4-Chloro-6-(2,4-difluorobenzyl)pyrimidine

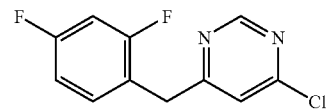

$^1$H-NMR: 4.10 (s, 2H), 6.82-6.92 (m, 2H), 7.18 (s, 1H), 7.23-7.28 (m, 1H), 8.90 (s, 1H)

REFERENCE PRODUCTION EXAMPLE 31

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 1.5 g of 3-fluorobenzyl bromide dissolved in 20 ml of tetrahydrofuran was slowly added with heating under reflux, followed by stirring for 20 minutes. (The solution thus obtained is referred to as solution I). In 10 ml of tetrahydrofuran were suspended 1.5 g of 4,6-dichloropyrimidine and 0.1 g of dichlorobistriphenylphosphine palladium, to which the above solution I was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.62 g of 4-chloro-6-(3-fluorobenzyl)pyrimidine.

4-Chloro-6-(3-fluorobenzyl)pyrimidine

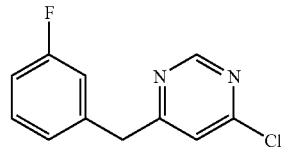

$^1$H-NMR: 4.09 (s, 2H), 6.96-7.05 (m, 3H), 7.15 (s, 1H), 7.26-7.33 (m, 1H), 8.92 (s, 1H)

REFERENCE PRODUCTION EXAMPLE 32

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.2 g of 2-chloro-6-fluorobenzyl bromide dissolved in 20 ml of tetrahydrofuran was slowly added with heating under reflux, followed by stirring for 20 minutes. (The solution thus obtained is referred to as solution J). In 10 ml of tetrahydrofuran were suspended 1.5 g of 4,6-dichloropyrimidine and 0.1 g of dichlorobistriphenylphosphine palladium, to which the above solution J was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.77 g of 4-chloro-6-(2-chloro-6-fluorobenzyl)pyrimidine.

4-Chloro-6-(2-chloro-6-fluorobenzyl)pyrimidine

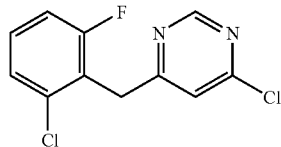

$^1$H-NMR: 4.30 (s, 2H), 7.05-7.08 (m, 2H), 7.24-7.29 (m, 2H), 8.90 (s, 1H)

REFERENCE PRODUCTION EXAMPLE 33

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.2 g of 3-chloro-2-fluorobenzyl bromide dissolved in 20 ml of tetrahydrofuran was slowly added with heating under reflux, followed by stirring for 20 minutes. (The solution thus obtained is referred to as solution K). In 10 ml of tetrahydrofuran were suspended 1.5 g of 4,6-dichloropyrimidine and 0.1 g of dichlorobistriphenylphosphine palladium, to which the above solution K was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.89 g of 4-chloro-6-(3-chloro-2-fluorobenzyl)pyrimidine.

4-Chloro-6-(3-chloro-2-fluorobenzyl)pyrimidine

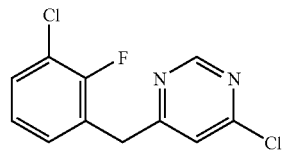

$^1$H-NMR: 4.14 (s, 2H), 7.04-7.43 (m, 4H), 8.90 (s, 1H)

REFERENCE PRODUCTION EXAMPLE 34

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.0 g of 2-bromobenzyl bromide dissolved in 20 ml of tetrahydrofuran was slowly added with heating under reflux, followed by stirring for 20 minutes. (The solution thus obtained is referred to as solution L). In 10 ml of tetrahydrofuran were suspended 1.5 g of 4,6-dichloropyrimidine and 0.1 g of dichlorobistriphenylphosphine palladium, to which the above solution L was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.69 g of 4-chloro-6-(2-bromobenzyl)pyrimidine.

4-Chloro-6-(2-bromobenzyl)pyrimidine

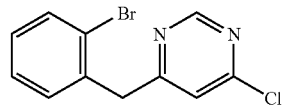

$^1$H-NMR: 4.27 (s, 2H), 7.10 (s, 1H), 7.16-7.22 (m, 1H), 7.31-7.34 (m, 2H), 7.61 (d, 1H), 8.90 (s, 1H)

REFERENCE PRODUCTION EXAMPLE 35

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.0 g of 1-(1-bromoethyl)-3-fluorobenzene dissolved in 20 ml of tetrahydrofuran was slowly added with heating under reflux, followed by stirring for 20 minutes. (The solution thus obtained is referred to as solution M). In 10 ml of tetrahydrofuran were suspended 1.5 g of 4,6-dichloropyrimidine and 0.2 g of tetrakistriphenylphosphine palladium, to which the above solution M was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.43 g of 4-chloro-6-(1-(3-fluorophenyl)ethyl)pyrimidine.

4-Chloro-6-(1-(3-fluorophenyl)ethyl)pyrimidine

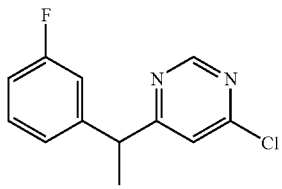

¹H-NMR: 1.68 (d, 3H), 4.21 (q, 1H), 6.90-7.11 (m, 3H), 7.15 (s, 1H), 7.28-7.36 (m, 1H), 8.93 (s, 1H)

REFERENCE PRODUCTION EXAMPLE 36

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.0 g of 1-(1-bromoethyl)-2-fluorobenzene dissolved in 20 ml of tetrahydrofuran was slowly added with heating under reflux, followed by stirring for 20 minutes. (The solution thus obtained is referred to as solution N). In 10 ml of tetrahydrofuran were suspended 1.5 g of 4,6-dichloropyrimidine and 0.2 g of tetrakistriphenylphosphine palladium, to which the above solution N was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.67 g of 4-chloro-6-(1-(2-fluorophenyl)ethyl)pyrimidine.

4-Chloro-6-(1-(2-fluorophenyl)ethyl)pyrimidine

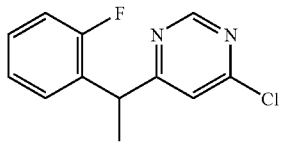

¹H-NMR: 1.68 (d, 3H), 4.50 (q, 1H), 7.04-7.37 (m, 5H, involving a singlet at 7.20), 8.92 (s, 1H)

REFERENCE PRODUCTION EXAMPLE 37

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.4 g of 2-chloro-5-methyl-6-fluorobenzyl bromide dissolved in 20 ml of tetrahydrofuran was slowly added with heating under reflux, followed by stirring for 20 minutes. (The solution thus obtained is referred to as solution L). In 10 ml of tetrahydrofuran were suspended 1.5 g of 4,6-dichloropyrimidine and 0.1 g of dichlorobistriphenylphosphine palladium, to which the above solution L was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.53 g of 4-chloro-6-(2-chloro-5-methyl-6-fluorobenzyl)pyrimidine.

4-Chloro-6-(2-chloro-5-methyl-6-fluorobenzyl)pyrimidine

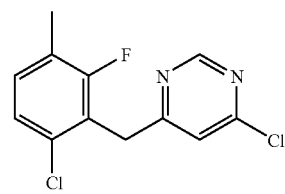

¹H-NMR: 2.38 (s, 3H), 4.34 (s, 2H), 7.02 (t, 1H), 7.07 (s, 1H), 7.24 (dd, 1H), 7.27 (s, 1H), 8.91 (s, 1H)

REFERENCE PRODUCTION EXAMPLE 38

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 2.4 g of 2-chloro-3,6-difluorobenzyl bromide dissolved in 20 ml of tetrahydrofuran was slowly added with heating under reflux, followed by stirring for 20 minutes. (The solution thus obtained is referred to as solution P). In 10 ml of tetrahydrofuran were suspended 1.5 g of 4,6-dichloropyrimidine and 0.1 g of dichlorobistriphenylphosphine palladium, to which the above solution P was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.64 g of 4-chloro-6-(2-chloro-3,6-difluorobenzyl)pyrimidine.

4-Chloro-6-(2-chloro-3,6-difluorobenzyl)pyrimidine

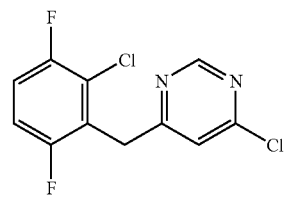

¹H-NMR: 4.32 (s, 2H), 7.02-7.19 (m, 3H, involving a singlet at 7.13), 8.90 (s, 1H)

REFERENCE PRODUCTION EXAMPLE 39

In 10 ml of N,N-dimethylformamide were dissolved 608 mg of 4-chloro-6-(2-fluorophenyl)pyrimidine and 527 mg of 2-butyn-1,4-diol, to which 245 mg of sodium hydride (60% in oil) was added, followed by stirring at room temperature for 9 hours. The reaction mixture was then poured into water and extracted with ethyl acetate. The organic layer was washed with a saturated aqueous sodium chloride solution, dried over anhydrous magnesium sulfate, and then concentrated. The resulting residue was subjected to silica gel column chromatography to give 465 mg of 4-(2-fluorophenyl)-6-(4-hydroxy-2-butynyloxy)pyrimidine.

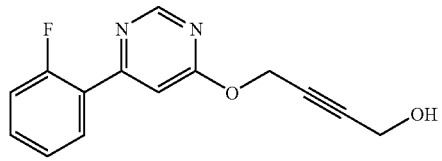

$^1$H-NMR: 1.68 (t, 1H), 4.34 (dt, 2H), 5.13 (t, 2H), 7.18 (dt, 1H), 7.23-7.51 (m, 2H), 7.33 (s, 1H), 8.12 (dt, 1H), 8.88 (s, 1H)

REFERENCE PRODUCTION EXAMPLE 40

In 10 ml of tetrahydrofuran was suspended 1.3 g of zinc (powder), to which dibromoethane (2 drops) was added. The mixture was heated under reflux for 5 minutes, to which trimethylsilane chloride was added. The mixture was further heated under reflux for 5 minutes, to which a solution of 1.9 g of 4-fluorobenzyl bromide dissolved in 20 ml of tetrahydrofuran was slowly added with heating under reflux, followed by stirring for 20 minutes. (The solution thus obtained is referred to as solution Q). In 10 ml of tetrahydrofuran were suspended 1.5 g of 4,6-dichloropyrimidine and 0.1 g of dichlorobistriphenylphosphine palladium, to which the above solution Q was added, followed by heating under reflux for 3 hours and further stirring at room temperature for 12 hours. The reaction mixture was then poured into water and extracted three times with ethyl acetate. The organic layers were combined, washed with water, dried over anhydrous magnesium sulfate, and then concentrated. The residue was subjected to silica gel column chromatography to give 0.72 g of 4-chloro-6-(4-fluorobenzyl)pyrimidine.

4-Chloro-6-(4-fluorobenzyl)pyrimidine

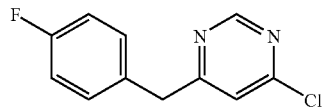

$^1$H-NMR: 4.07 (s, 2H), 6.94-7.24 (m, 5H), 8.91 (s, 1H)

REFERENCE PRODUCTION EXAMPLE 41

A reaction vessel was charged with [1,1'-bis(diphenylphosphino)ferrocene dichloropalladium]methylene chloride complex, 984 mg of 2,6-difluorophenylboronic acid, and 1.32 g of sodium carbonate, to which 15 ml of toluene, 4 ml of ethanol, 4 ml of water, and 997 mg of 2-methyl-4,6-dichloropyrimidine were added, followed by stirring at 80° C. under an atmosphere of a nitrogen gas for 6 hours. The reaction mixture was then left for cooling to room temperature, and water was added to the reaction mixture, which was extracted with ethyl acetate. The organic layer was washed with a saturated aqueous sodium chloride solution, dried over anhydrous magnesium sulfate, and then concentrated. The residue was subjected to silica gel column chromatography to give 656 mg of 4-chloro-2-methyl-6-(2,3-difluorophenyl)pyrimidine.

4-Chloro-2-methyl-6-(2,3-difluorophenyl)pyrimidine

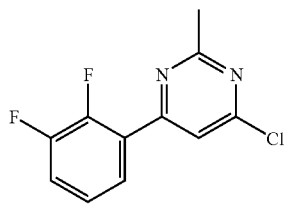

$^1$H-NMR: 2.79 (s, 3H), 7.15-7.48 (m, 2H), 7.67 (s, 1H), 7.85-7.95 (m, 1H)

REFERENCE PRODUCTION EXAMPLE 42

In 4.2 ml of tetrahydrofuran was suspended 0.12 g of sodium hydride (60% in oil), to which 0.8 ml of a tetrahydrofuran solution containing 0.5 g of 4-chloro-6-(2,3-difluorophenylamino)pyrimidine was slowly added dropwise with stirring at room temperature. The mixture was stirred at room temperature for 20 minutes, to which 0.8 ml of a tetrahydrofuran solution containing 0.48 g of iodoethane was slowly added dropwise at 0° C., followed by further stirring for 8 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.23 g of 4-chloro-6-(N-ethyl-N-(2,3-difluorophenyl)amino)pyrimidine.

4-Chloro-6-(N-ethyl-N-(2,3-difluorophenyl)amino)pyrimidine

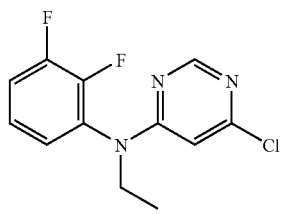

$^1$H-NMR: 1.25 (t, 3H), 3.96 (q, 2H), 6.72 (s, 1H), 7.00-7.30 (m, 2H), 7.64 (dd, 1H), 8.55 (s, 1H)

REFERENCE PRODUCTION EXAMPLE 43

In 6.7 ml of tetrahydrofuran was suspended 0.16 g of sodium hydride (60% in oil), to which 0.8 ml of a tetrahydrofuran solution containing 0.5 g of 4-chloro-6-(3-fluorophenylamino)pyrimidine was slowly added dropwise with stirring at room temperature. The mixture was stirred at room temperature for 20 minutes, to which 0.8 ml of a tetrahydrofuran solution containing 0.42 g of iodoethane was slowly added at 0° C., followed by further stirring for 8 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.43 g of 4-chloro-6-(N-ethyl-N-(3-fluorophenyl) amino)pyrimidine.

4-Chloro-6-(N-ethyl-N-(3-fluorophenyl)amino)pyrimidine

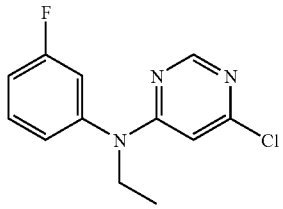

$^1$H-NMR: 1.22 (t, 3H), 3.99 (q, 2H), 6.17 (s, 1H), 6.93-7.15 (m, 3H), 7.43-7.52 (m, 1H), 8.46 (s, 1H)

REFERENCE PRODUCTION EXAMPLE 44

In 4.7 ml of tetrahydrofuran was suspended 0.12 g of sodium hydride (60% in oil), to which 1 ml of a tetrahydrofuran solution containing 0.45 g of 2-chlorocyclohexanol was slowly added dropwise with stirring at 0° C. The mixture was stirred at 0° C. for 10 minutes, to which 1 ml of a tetrahydrofuran solution containing 0.5 g of 4,6-dichloropyrimidine was added at 0° C., followed by further stirring for 20 minutes. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.38 g of 4-chloro-6-(2-chlorocyclohexyloxy)pyrimidine.

4-Chloro-6-(2-chlorocyclohexyloxy)pyrimidine

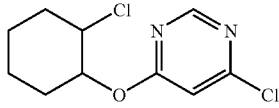

$^1$H-NMR: 1.44-1.49 (m, 2H), 1.73-1.82 (m, 2H), 2.15-2.30 (m, 2H), 3.91-4.08 (m, 1H), 5.19-5.31 (m, 1H), 6.79 (s, 1H), 8.56 (s, 1H)

REFERENCE PRODUCTION EXAMPLE 45

In 6.7 ml of tetrahydrofuran was suspended 0.18 g of sodium hydride (60% in oil), to which 1 ml of a tetrahydrofuran solution containing 0.42 g of 2-methylcyclohexanol(cis:trans=3:7) was slowly added dropwise with stirring at 0° C. The mixture was stirred at 0° C. for 10 minutes, to which 1 ml of a tetrahydrofuran solution containing 0.5 g of 4,6-dichloropyrimidine was added at 0° C., followed by further stirring at room temperature for 2 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.55 g of 4-chloro-6-(2-methylcyclohexyloxy)pyrimidine as a mixture of cis and trans forms.

4-Chloro-6-(2-methylcyclohexyloxy)pyrimidine

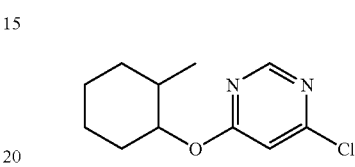

Cis Form:
$^1$H-NMR: 0.92 (d, 3H), 1.33-2.00 (m, 9H), 5.26-5.31 (m, 1H), 6.76 (s, 1H), 8.53 (s, 1H)

Trans Form:
$^1$H-NMR: 0.93 (d, 3H), 1.11-1.38 (m, 4H), 1.65-1.83 (m, 4H), 2.10-2.14 (m, 1H), 4.78-4.85 (m, 1H), 6.72 (s, 1H), 8.53 (s, 1H)

REFERENCE PRODUCTION EXAMPLE 46

In 5 ml of tetrahydrofuran was suspended 0.11 g of sodium hydride (60% in oil), to which 1 ml of a tetrahydrofuran solution containing 0.22 g of trans-2-methylcyclopentanol was slowly added dropwise with stirring at 0° C. The mixture was stirred at 0° C. for 10 minutes, to which 1 ml of a tetrahydrofuran solution containing 0.3 g of 4,6-dichloropyrimidine was added at 0° C., followed by further stirring for 2 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.38 g of 4-chloro-6-(trans-2-methylcyclopentyloxy) pyrimidine.

4-Chloro-6-(trans-2-methylcyclopentyloxy)pyrimidine

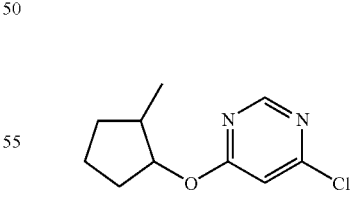

$^1$H-NMR: 1.05 (d, 3H), 1.21-1.32 (m, 1H), 1.68-1.81 (m, 3H), 1.93-2.00 (m, 1H), 2.01-2.18 (m, 1H), 4.99-5.04 (m, 1H), 6.72 (s, 1H), 8.55 (s, 1H)

REFERENCE PRODUCTION EXAMPLE 47

In 4 ml of tetrahydrofuran was suspended 0.11 g of sodium hydride (60% in oil), to which 1 ml of a tetrahydrofuran solution containing 0.25 g of cycloheptanol was slowly added dropwise with stirring at 0° C. The mixture was stirred at 0° C. for 10 minutes, to which 1 ml of a tetrahydrofuran solution containing 0.3 g of 4,6-dichloropyrimidine was added at 0° C., followed by further stirring for 2 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.43 g of 4-chloro-6-cycloheptyloxypyrimidine.

4-Chloro-6-cycloheptyloxypyrimidine

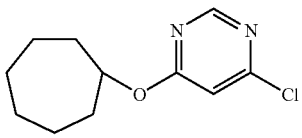

$^1$H-NMR: 1.50-1.83 (m, 10H), 1.99-2.05 (m, 2H), 5.27-5.35 (m, 1H), 6.70 (s, 1H), 8.54 (s, 1H)

REFERENCE PRODUCTION EXAMPLE 48

First, 18.9 g of 28% sodium methoxide in methanol was rapidly mixed with 4.7 g of formamide, and the mixture was heated under reflux, to which 30 ml of a methanol solution containing 5 g of ethyl methylmalonate was slowly added dropwise over 3 hours. The mixture was further heated under reflux with stirring for 10 hours and then left for cooling, and the suspension was concentrated under reduced pressure. Then, 10 ml of water was added to the residue, which was acidified with concentrated hydrochloric acid. The resulting precipitate was filtered by suction and dried under reduced pressure to give 2.8 g of 4,6-dihydroxy-5-methylpyrimidine.

4,6-Dihydroxy-5-methylpyrimidine

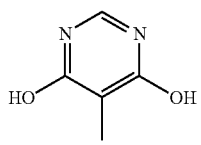

$^1$H-NMR (DMSO-d$_6$): 1.73 (s, 3H), 7.90 (s, 1H)

REFERENCE PRODUCTION EXAMPLE 49

A reaction vessel was charged at 0° C. with 2.8 g of 4,6-dihydroxy-5-emthylpyrimidine, 5.00 g of phosphorus oxychloride, and 3.3 g of diisopropylethylamine, followed by stirring at 80° C. for 4 hours. The mixture was then left for cooling and poured into ice water. The mixture was further stirred for 30 minutes and then extracted with ethyl acetate. The organic layers were combined and washed with a saturated aqueous sodium hydrogencarbonate solution and then with a saturated aqueous sodium chloride solution, and the organic layers were then dried over anhydrous magnesium sulfate and concentrated. The residue was subjected to silica gel column chromatography to give 2.4 g of 4,6-dichloro-5-methylpyrimidine.

4,6-Dichloro-5-methylpyrimidine

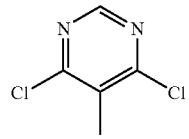

$^1$H-NMR: 2.50 (s, 3H), 8.63 (s, 1H)

REFERENCE PRODUCTION EXAMPLE 50

In 12 ml of tetrahydrofuran was suspended 0.32 g of sodium hydride (60% in oil), to which 2 ml of a tetrahydrofuran solution containing 0.43 g of 2-butyn-1-ol was slowly added dropwise with stirring at room temperature. The mixture was stirred at room temperature for 20 minutes and then cooled to 0° C., to which 2 ml of a tetrahydrofuran solution containing 1 g of 4,6-dichloro-5-methylpyrimidine was slowly added, followed by further stirring at 0° C. for 2 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 1.1 g of 4-chloro-6-(2-butynyloxy)-5-methylpyrimidine.

4-Chloro-6-(2-butynyloxy)-5-methylpyrimidine

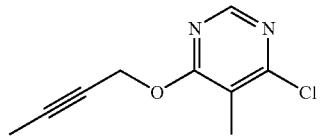

$^1$H-NMR: 1.88 (t, 3H), 2.26 (s, 3H), 5.00 (q, 2H), 8.44 (s, 1H)

REFERENCE PRODUCTION EXAMPLE 51

In 4 ml of tetrahydrofuran was suspended 0.12 g of sodium hydride (60% in oil), to which 1 ml of a tetrahydrofuran solution containing 0.28 g of cis-2-methylcyclohexanol was slowly added dropwise with stirring at 0° C. The mixture was stirred at 0° C. for 10 minutes, to which 1 ml of a tetrahydrofuran solution containing 0.3 g of 4,6-dichloropyrimidine was added at 0° C., followed by further stirring at room temperature for 3 hours. The reaction mixture was then poured into a saturated aqueous ammonium chloride solution and extracted three times with t-butyl methyl ether. The organic layers were combined, washed with water, dried over anhydrous magnesium sulfate, and then concentrated. The residue was subjected to silica gel column chromatography to give 0.12 g of 4-chloro-6-(cis-2-methylcyclohexyloxy)pyrimidine.

4-Chloro-6-(cis-2-methylcyclohexyloxy)pyrimidine

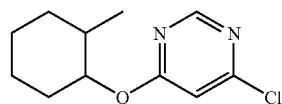

$^1$H-NMR: 0.92 (d, 3H), 1.33-2.00 (m, 9H), 5.26-5.31 (m, 1H), 6.76 (s, 1H), 8.53 (s, 1H)

REFERENCE PRODUCTION EXAMPLE 52

In 4 ml of tetrahydrofuran was suspended 0.11 g of sodium hydride (60% in oil), to which 1 ml of a tetrahydrofuran solution containing 0.25 g of trans-2-methylcyclohexanol was slowly added dropwise with stirring at 0° C. The mixture was stirred at 0° C. for 10 minutes, to which 1 ml of a tetrahydrofuran solution containing 0.3 g of 4,6-dichloropyrimidine was added at 0° C., followed by further stirring at room temperature for 3 hours. The reaction mixture was then poured into a saturated aqueous ammonium chloride solution and extracted three times with ethyl acetate. The organic layers were combined, washed with water, dried over anhydrous magnesium sulfate, and then concentrated. The residue was subjected to silica gel column chromatography to give 0.18 g of 4-chloro-6-(trans-2-methylcyclohexyloxy)pyrimidine.

4-Chloro-6-(trans-2-methylcyclohexyloxy)pyrimidine

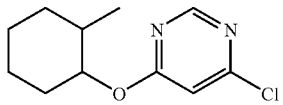

$^1$H-NMR: 0.93 (d, 3H), 1.11-1.38 (m, 4H), 1.65-1.83 (m, 4H), 2.10-2.14 (m, 1H), 4.78-4.85 (m, 1H), 6.72 (s, 1H), 8.53 (s, 1H)

REFERENCE PRODUCTION EXAMPLE 53

Under an atmosphere of a nitrogen gas, 2.98 g of 4,6-dichloropyrimidine, 1.81 g of 3,3-dimethyl-1-butyne, 351 mg of dichlorobis(triphenylphosphine)palladium, 381 mg of copper iodide, 4.05 g of triethylamine and 525 mg of triphenylphosphine was added to 20 ml of acetonitrile and the suspension was stirred for 6 hours at 45° C. After cooling the reaction mixture was diluted with t-butyl methyl ether and washed three times with water. The organic layers were dried over sodium sulfate and concentrated. The residue was subjected to silica gel thin layer chromatography to give 1.86 g of 4-chloro-6-(3,3-dimethyl-1-butynyl)pyrimidine.

4-Chloro-6-(3,3-dimethyl-1-butynyl)pyrimidine

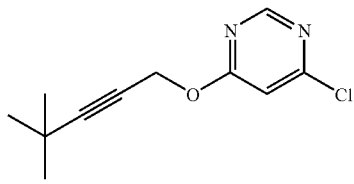

$^1$H-NMR: 1.35 (s, 9H), 7.37 (d, 1H), 8.90 (s, 1H)

REFERENCE PRODUCTION EXAMPLE 54

In 18 ml of tetrahydrofuran was suspended 0.56 g of sodium hydride (60% in oil), to which 2 ml of a tetrahydrofuran solution containing 0.8 g of 2-butyn-1-ol was slowly added dropwise with stirring at room temperature. The mixture was stirred at room temperature for 20 minutes and then cooled to 0° C., to which 3 ml of a tetrahydrofuran solution containing 2 g of 4,5,6-trichloropyrimidine was slowly added dropwise, followed by further stirring at 0° C. for 2 hours. The reaction mixture was then poured into a saturated aqueous ammonium chloride solution and extracted three times with ethyl acetate. The organic layers were combined, washed with brine, dried over anhydrous magnesium sulfate, and then concentrated. The residue was subjected to silica gel column chromatography to give 2.23 g of 4,5-dichloro-6-(2-butynyloxy)pyrimidine.

4,5-Dichloro-6-(2-butynyloxy)pyrimidine

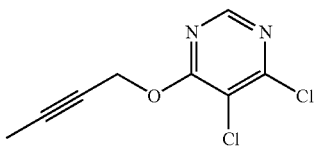

$^1$H-NMR: 1.88 (t, 3H), 5.08 (q, 2H), 8.48 (s, 1H)

REFERENCE PRODUCTION EXAMPLE 55

In 30 ml of tetrahydrofuran was suspended 1.78 g of sodium hydride (60% in oil), to which 3 ml of a tetrahydrofuran solution containing 2.35 g of 1,2-cyclohexanediol (mixture of cis-form and trans-form) was slowly added dropwise with stirring at room temperature. The mixture was stirred at room temperature for 10 minutes and then cooled to 0° C., to which 7 ml of a tetrahydrofuran solution containing 3 g of 4,6-dichloropyrimidine was slowly added dropwise, followed by further stirring at 0° C. for 3 hours. The reaction mixture was then poured into a saturated aqueous ammonium chloride solution and extracted three times with ethyl acetate. The organic layers were combined, washed with brine, dried over anhydrous magnesium sulfate, and then concentrated. The residue was subjected to silica gel column chromatography to give 1.6 g of 4-chloro-6-(2-hydroxycyclohexyloxy)pyrimidine.

4-Chloro-6-(2-hydroxycyclohexyloxy)pyrimidine

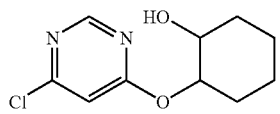

$^1$H-NMR: 1.37-1.45 (m, 2H), 1.59-2.04 (m, 6H), 2.48 (bs, 1H), 3.99-4.02 (m, 1H), 5.30-5.35 (m, 1H), 6.80 (s, 1H), 8.54 (s, 1H) with peaks due to the minor trans-form at 2.55 (bs), 3.64-3.75 (m), 4.93-5.00 (m), 6.78 (s)

REFERENCE PRODUCTION EXAMPLE 56

In 2 ml of tetrahydrofuran was suspended 0.05 g of sodium hydride (60% in oil), to which 0.5 ml of a tetrahydrofuran solution containing 0.12 g of 2-butyn-1-ol was slowly added dropwise with stirring at room temperature. The mixture was stirred at room temperature for 20 minutes and then cooled to 0° C., to which 0.5 ml of a tetrahydrofuran solution containing 0.25 g of 4,6-dichloro-5-fluoropyrimidine was slowly added dropwise, followed by further stirring at 0° C. for 30 minutes. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.30 g of 4-chloro-5-fluoro-6-(2-butynyloxy)pyrimidine.

4-Chloro-5-fluoro-6-(2-butynyloxy)pyrimidine

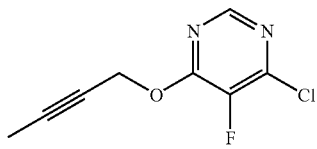

$^1$H-NMR: 1.88 (t, 3H), 5.08 (q, 2H), 8.37 (s, 1H)

REFERENCE PRODUCTION EXAMPLE 57

In 5 ml of tetrahydrofuran was suspended 0.19 g of sodium hydride (60% in oil), to which 0.5 ml of a tetrahydrofuran solution containing 0.48 g of 2,3-dimethylcyclohexanol (mixture of isomers) was slowly added dropwise with stirring at room temperature. The mixture was stirred at room temperature for 10 minutes and then cooled to 0° C., to which 1.5 ml of a tetrahydrofuran solution containing 0.5 g of 4,6-dichloropyrimidine was slowly added dropwise, followed by further stirring at room temperature for 3 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.72 g of 4-chloro-6-(2,3-dimethylcyclohexyloxy)pyrimidine.

4-Chloro-6-(2,3-dimethylcyclohexyloxy)pyrimidine

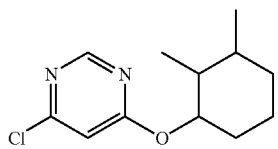

$^1$H-NMR: 0.84-2.14 (m, 14H), 4.74-4.89 (m, 1H), 6.72 (s, 1H), 8.53 (s, 1H) with peaks due to the minor isomers at 5.10-5.21 (m)

REFERENCE PRODUCTION EXAMPLE 58

In 5 ml of tetrahydrofuran was suspended 0.14 g of sodium hydride (60% in oil), to which 0.5 ml of a tetrahydrofuran solution containing 0.34 g of 3-methylcyclohexanol (mixture of cis-dorm and trans-form) was slowly added dropwise with stirring at room temperature. The mixture was stirred at room temperature for 10 minutes and then cooled to 0° C., to which 1.5 ml of a tetrahydrofuran solution containing 0.4 g of 4,6-dichloropyrimidine was slowly added dropwise, followed by further stirring at room temperature for 4 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.31 g of 4-chloro-6-(3-methylcyclohexyloxy)pyrimidine.

4-Chloro-6-(3-methylcyclohexyloxy)pyrimidine

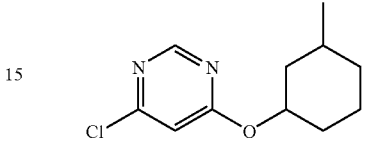

$^1$H-NMR: 0.85-2.12 (m, 12H), 5.02-5.12 (m, 1H), 6.70 (s, 1H), 8.54 (s, 1H) with peaks due to the minor isomer at 5.42-5.51 (m), 6.74 (s)

REFERENCE PRODUCTION EXAMPLE 59

To 2 ml of ethanol were added 0.3 g of 4,5,6-trichloropyrimidine and 0.5 g of N-ethylaniline, followed by heating under reflux for 8 hours. The reaction mixture was then left for cooling to room temperature and concentrated under reduced pressure. The residue was added water and extracted three times with t-butyl methyl ether. The organic layers were combined, dried over anhydrous magnesium sulfate, and then concentrated. The residue was subjected to silica gel column chromatography to give 0.5 g of 4,5-dichloro-6-(N-ethyl-N-phenylamino)pyrimidine.

4,5-Dichloro-6-(N-ethyl-N-phenylamino)pyrimidine

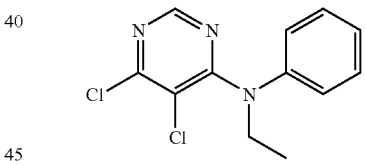

$^1$H-NMR: 1.23 (t, 3H), 4.04 (q, 2H), 7.07 (d, 2H), 7.25 (t, 1H), 7.34 (t, 2H), 8.40 (s, 1H)

REFERENCE PRODUCTION EXAMPLE 60

In 4 ml of tetrahydrofuran was suspended 0.1 g of sodium hydride (60% in oil), to which 0.5 ml of a tetrahydrofuran solution containing 0.23 g of cis-4-methylcyclohexanol was slowly added dropwise with stirring at room temperature. The mixture was stirred at room temperature for 10 minutes and then cooled to 0° C., to which 1 ml of a tetrahydrofuran solution containing 0.3 g of 4,6-dichloropyrimidine was slowly added dropwise, followed by further stirring at room temperature for 4 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.37 g of 4-chloro-6-(cis-4-methylcyclohexyloxy)pyrimidine.

4-Chloro-6-(cis-4-methylcyclohexyloxy)pyrimidine

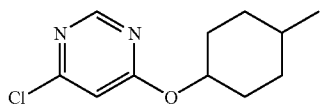

¹H-NMR: 0.94 (d, 3H), 1.26-1.67 (m, 7H), 1.95-2.02 (m, 2H), 5.30-5.39 (m, 1H), 6.76 (s, 1H), 8.54 (s, 1H)

REFERENCE PRODUCTION EXAMPLE 61

In 4 ml of tetrahydrofuran was suspended 0.1 g of sodium hydride (60% in oil), to which 0.5 ml of a tetrahydrofuran solution containing 0.23 g of trans-4-methylcyclohexanol was slowly added dropwise with stirring at room temperature. The mixture was stirred at room temperature for 10 minutes and then cooled to 0° C., to which 1 ml of a tetrahydrofuran solution containing 0.3 g of 4,6-dichloropyrimidine was slowly added dropwise, followed by further stirring at room temperature for 4 hours. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.37 g of 4-chloro-6-(trans-4-methylcyclohexyloxy)pyrimidine.

4-Chloro-6-(trans-4-methylcyclohexyloxy)pyrimidine

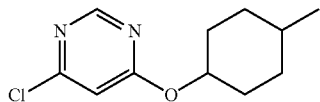

¹H-NMR: 0.94 (d, 3H), 1.03-1.17 (m, 2H), 1.39-1.52 (m, 3H), 1.76-1.81 (m, 2H), 2.07-2.13 (m, 2H), 4.98-5.08 (m, 1H), 6.69 (s, 1H), 8.53 (s, 1H)

REFERENCE PRODUCTION EXAMPLE 62

REFERENCE PRODUCTION EXAMPLE 61

In 4 ml of tetrahydrofuran was suspended 0.2 g of sodium hydride (60% in oil), to which 1 ml of a tetrahydrofuran solution containing 0.39 g of cis-1,2-cyclohexanediol was slowly added dropwise with stirring at room temperature. The mixture was stirred at room temperature for 10 minutes and then cooled to 0° C., to which 2 ml of a tetrahydrofuran solution containing 0.5 g of 4,6-dichloropyrimidine was slowly added dropwise, followed by further stirring at 0° C. for 30 minutes. The reaction mixture was then poured into a saturated aqueous ammonium chloride solution and extracted three times with ethyl acetate. The organic layers were combined, washed with brine, dried over anhydrous magnesium sulfate, and then concentrated. The residue was subjected to silica gel column chromatography to give 0.42 g of 4-chloro-6-(cis-2-hydroxycyclohexyloxy)pyrimidine.

4-Chloro-6-(cis-2-hydroxycyclohexyloxy)pyrimidine

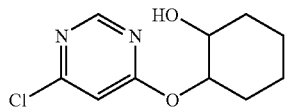

¹H-NMR: 1.37-1.45 (m, 2H), 1.59-2.04 (m, 6H), 2.48 (bs, 1H), 3.99-4.02 (m, 1H), 5.30-5.35 (m, 1H), 6.80 (s, 1H), 8.54 (s, 1H)

REFERENCE PRODUCTION EXAMPLE 63

To 3.2 ml of tetrahydrofuran were added 0.37 g of 4-chloro-6-(cis-2-hydroxycyclohexyloxy)pyrimidine and 0.45 ml of triethylamine, to which 0.25 ml of chlorotrimethylsilane was slowly added dropwise with stirring at 0° C. After stirring at room temperature for 3 hours, the reaction mixture was then poured into a saturated aqueous ammonium chloride solution and extracted three times with ethyl acetate. The organic layers were combined, washed with brine, dried over anhydrous magnesium sulfate, and then concentrated. The residue was subjected to silica gel column chromatography to give 0.5 g of 4-chloro-6-(cis-2-trimethylsilanyloxycyclohexyloxy)pyrimidine.

4-Chloro-6-(cis-2-trimethylsilanyloxycyclohexyloxy)pyrimidine

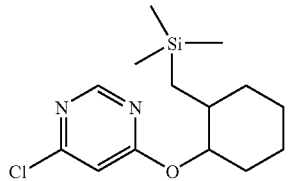

¹H-NMR: 0.14 (s, 9H), 1.12-1.36 (m, 2H), 1.48-1.73 (m, 5H), 1.88-1.95 (m, 1H), 3.94-3.98 (m, 1H), 5.12-5.16 (m, 1H), 6.69 (s, 1H), 8.46 (s, 1H)

REFERENCE PRODUCTION EXAMPLE 64

In 2 ml of tetrahydrofuran was suspended 0.63 g of zinc (powder), to which dibromoethane (1 drop) was added. The mixture was heated under reflux for 5 minutes, to which chlorotrimethylsilane (1 drop) was added. The mixture was further heated under reflux for 5 minutes, to which a solution of 0.91 g of 2-fluorobenzylbromide dissolved in 4 ml of tetrahydrofuran was slowly added with heating under reflux, followed by stirring for 20 minutes. (The solution thus obtained is referred to as solution R). In 4 ml of tetrahydrofuran were suspended 0.8 g of 4,6-dichloropyrimidine and 0.02 g of dichlorobistriphenylphosphine palladium, to which the above solution R was added, followed by heating under reflux for 3 hours and further stirring at room temperature for 12 hours. The reaction mixture was then poured into water and extracted three times with t-butyl methyl ether. The organic layers were combined, washed with brine, dried over anhydrous magnesium sulfate, and then concentrated. The residue was subjected to silica gel column chromatography to give 0.46 g of 4-chloro-5-fluoro-6-(2-fluorobenzyl)pyrimidine.

143

4-Chloro-5-fluoro-6-(2-fluorobenzyl)pyrimidine

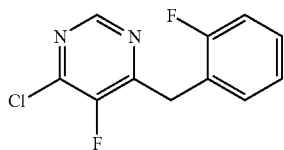

$^1$H-NMR: 4.23 (s, 2H), 7.01-7.12 (m, 2H), 7.21-7.30 (m, 2H), 8.66 (s, 1H)

REFERENCE PRODUCTION EXAMPLE 65

In 1 ml of tetrahydrofuran was suspended 0.04 g of sodium hydride (60% in oil), to which 0.5 ml of a tetrahydrofuran solution containing 0.06 g of 3-pentyn-2-ol was slowly added dropwise with stirring at room temperature. The mixture was stirred at room temperature for 20 minutes and then cooled to 0° C., to which 0.5 ml of a tetrahydrofuran solution containing 0.1 g of 4,6-dichloropyrimidine was slowly added dropwise, followed by further stirring for 30 minutes. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.12 g of 4-chloro-6-(1-methyl-2-butynyloxy)pyrimidine.

4-Chloro-6-(1-methyl-2-butynyloxy)pyrimidine

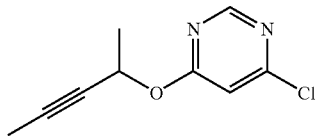

$^1$H-NMR: 1.60 (d, 3H), 1.84 (d, 3H), 5.74-5.82 (m, 1H), 6.78 (s, 1H), 8.60 (s, 1H)

REFERENCE PRODUCTION EXAMPLE 66

In 1 ml of tetrahydrofuran was suspended 0.03 g of sodium hydride (60% in oil), to which 0.5 ml of a tetrahydrofuran solution containing 0.06 g of 2-pentyn-1-ol was slowly added dropwise with stirring at room temperature. The mixture was stirred at room temperature for 20 minutes and then cooled to 0° C., to which 0.5 ml of a tetrahydrofuran solution containing 0.1 g of 4,6-dichloropyrimidine was slowly added dropwise, followed by further stirring for 30 minutes. The reaction mixture was then poured into a saturated aqueous ammonium chloride solution and extracted three times with t-butyl methyl ether. The organic layers were combined, washed with brine, dried over anhydrous magnesium sulfate, and then concentrated. The residue was subjected to silica gel column chromatography to give 0.12 g of 4-chloro-6-(2-pentynyloxy)pyrimidine.

144

4-Chloro-6-(2-pentynyloxy)pyrimidine

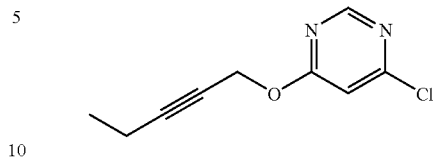

$^1$H-NMR: 1.17 (t, 3H), 2.25 (br. q, 2H), 5.01 (t, 2H), 6.82 (s, 1H), 8.60 (s, 1H) The following will describe formulation examples, in which parts are by weight and the present compounds are designated by their compound numbers shown in the above tables.

FORMULATION EXAMPLE 1

Emulsifiable Concentrates

Nine parts of each of the present compounds (1) to (191) is dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well mixing with stirring, to give an emulsifiable concentrate for each compound.

FORMULATION EXAMPLE 2

Wettable Powders

Nine parts of each of the present compounds (1) to (191) is added to a mixture of 4 parts of sodium lauryl sulfate, 4 parts of calcium lignin sulfonate, 20 parts of synthetic hydrated silicon oxide fine powder, and 65 parts of diatomaceous earth, followed well mixing with stirring, to give a wettable powder for each compound.

FORMULATION EXAMPLE 3

Granules

Three parts of each of the present compounds (1) to (191), 5 parts of synthetic hydrated silicon oxide fine powder, 5 parts of sodium dodecylbenzenesulfonate, 30 parts of bentonite, and 57 parts of clay are well mixed with stirring, and an appropriate amount of water is added to the mixture of these ingredients, followed by further stirring, granulation with a granulator, and drying by ventilation, to give a granule for each compound.

FORMULATION EXAMPLE 4

Dusts

First, 4.5 parts of each of the present compounds (1) to (191), 1 part of synthetic hydrated silicon oxide fine powder, 1 part of Doriresu B (available from Sankyo Co., Ltd.) as a flocculant, and 7 parts of clay are well mixed in a mortar and then mixed with stirring in a juicer. To the resulting mixture is added 86.5 parts by cut clay, followed by well mixing with stirring, to give a dust for each compound.

FORMULATION EXAMPLE 5

Ten parts of each of the present compounds (1) to (191), 35 parts of white carbon containing 50 parts of polyoxyethylene alkyl ether sulfate ammonium salt, and 55 parts of water are mixed and pulverized by wet grinding method to give a formulation for each compound.

FORMULATION EXAMPLE 6

Oil Sprays

First, 0.5% by weight of each of the present compounds (1) to (191) is dissolved in 10% by weight of dichloromethane, and this solution is mixed with 89.5% by weight of ISOPAR M (isoparaffin: registered trade name of Exxon Chemical Japan Ltd.) to give a 0.5% oil spay for each compound.

FORMULATION EXAMPLE 7

Oil-based Aerosols

First, 0.1% by weight of each of the present compounds (1) to (191) and 49.9% by weight of NEO-CHIOZOL (available from Chuo Kasei Co., Ltd.) are placed in an aerosol bomb, which is fitted with an aerosol valve and then filled with 25% by weight of dimethyl ether and 25% by weight of LPG, followed by shaking and fitting with an actuator, to give an oil-based aerosol.

FORMULATION EXAMPLE 8

Water-based Aerosols

An aerosol vessel is filled with a solution prepared by mixing 0.6% by weight of each of the present compounds (1) to (191), 0.01% by weight of BHT, 5% by weight of xylene, 3.3 parts of deodorized kerosine, and 1% by weight of an emulsifier {ATMOS 300 (registered trade name of Atlas Chemical Co.)}; and with 50% by weight of distilled water. The vessel is fitted with a valve part, through which 40% by weight of a propellant (LPG) is filled into the vessel under increased pressure, to give a water-based aerosol for each compound.

The following test examples are provided for demonstrating that the present compounds are useful as the active ingredients of pesticides. The present compounds are designated by their compound numbers shown in the above tables.

TEST EXAMPLE 1

Insecticidal Test Against Cotton Aphids (*Aphis gossypii*)

A formulation of a test compound obtained in Formulation Example 5 was diluted with water so that the active ingredient concentration came to 500 ppm to prepare a test spray solution.

The seeds of cucumber were planted in polyethylene cups and grown until their first foliage leaves developed, on which about 20 cotton aphids (*Aphis gossypii*) were made parasitic. After one day, the test spray solution was sprayed at the rate of 20 ml/cup onto the cucumber plants. On the 6th day after the application, the number of cotton aphids was examined and the control value was determined by the following formula:

Control value (%)={1−($Cb \times Tai$)/($Cai \times Tb$)}×100 wherein the variables in the formula have the following meanings:

Cb: the number of insects before the treatment in the non-treated area;

Cai: the number of insects at the time of observation in the non-treated area;

Tb: the number of insects before the treatment in the treated area; and

Tai: the number of insects at the time of observation in the treated area.

As a result, the present compounds (1), (2), (3), (5), (9), (10), (13), (15) to (19), (21), (26), (27), (29), (33) to (39), (42) to (47), (51), (54) to (64), (66), (67), (72), (73), (75), (77) to (83), (85) to (92), (94) to (110), (112), (113), (115) to (118), (120), (121), (122), (124), (125), (129), (130), (134), (135), (137), (138), (142) to (151), (154) to (170), (172), (173), (175) to (180), (182), (183), (185), (187) to (191) had the control value of 90% or higher.

TEST EXAMPLE 2

Insecticidal Test Against Cotton Aphids (*Aphis gossypii*)

A formulation of a test compound obtained in Formulation Example 5 was diluted with water so that the active ingredient concentration came to 500 ppm to prepare a test chemical solution.

Cucumber seedlings (at the stage of developing the first foliage leaf) cultivated in polyethylene cups each having 5 holes of 5 mm in diameter at the bottom were treated with the test chemical solution, which had been prepared as described above and was absorbed in a volume of 55 ml from the bottom of the cups. The cucumber plants were then left in a greenhouse at 25° C. for 6 days, and about 20 cotton aphids were made parasitic thereon. On the 6th day after the application, the number of cotton aphids was examined, and the control value was determined in the same manner as described in Test Example 1.

As a result, the present compounds (9), (21), (33), (36), (39), (42), (44), (45), (51), (63), (80), (83), (88), (96), (101), (104), (105), (106), (108), (110), (112), (115), (120), (121), (124), (137), (138), (144), (148), (149), (157), (158) and (185) had the control value of 90% or higher.

TEST EXAMPLE 3

Insecticidal Test Against Western Flower Thrips (*Frankliniella occidentalis*)

A formulation of a test compound obtained in Formulation Example 5 was diluted with water so that the active ingredient concentration came to 500 ppm to prepare a test spray solution.

The seeds of cucumber were planted in polyethylene cups and grown until their first foliage leaves developed, and the above test spray solution was sprayed at the rate of 20 ml/cup onto these cucumber plants. After the chemical solution sprayed onto the cucumber plants was dried, the first foliage leaves were cut off and placed on a water-containing filter paper (70 mm in diameter) in a polyethylene cup (110 mm in diameter). Thirty larvae of western flower thrips (*Frankliniella occidentalis*) were set free in the polyethylene cup, and the lid was put on the polyethylene cup. After 7 days, the number of surviving insects was examined.

As a result, for the present compounds (1), (2), (3), (5), (6), (7), (13), (15), (16), (17), (19), (20), (21), (29), (34) to (39), (43), (44), (45), (51), (54), (55), (58), (59), (63), (77), (80), (82), (83), (88), (134), (149), (150), (169), (176), (180), (182), (183), (190) and (191), the number of surviving insects on the leaves treated with each of these compounds was zero.

TEST EXAMPLE 4

Insecticidal Test Against Silverleaf Whiteflies
(*Bemisia argentifoli*)

A formulation of a test compound obtained in Formulation Example 5 was diluted with water so that the active ingredient concentration came to 500 ppm to prepare a test spray solution.

The seeds of cabbage were planted in polyethylene cups and grown until their first foliage leaves developed. The first foliage leaves were left and the other leaves were cut off. Some adults of silverleaf whiteflies were set free on the cabbage plants and allowed to lay eggs for about 24 hours. The cabbage plants with about 80 to 100 eggs thus laid were left in a greenhouse for 8 days, and the above test spray solution was sprayed at the rate of 20 ml/cup onto the cabbage plants with larvae being hatched from the laid eggs. On the 7th day after the application, the number of surviving larvae was counted.

As a result, for the present compounds (1) to (6), (9), (10), (13) to (16), (19), (21), (26) to (29), (33) to (39), (42) to (47), (49), (51), (52), (54) to (63), (66), (67), (68), (73), (76) to (83), (85) to (92), (94) to (105), (110), (112), (113), (115) to (118), (120), (121), (124), (130), (131), (134) to (138), (142), (143), (144), (146), (147), (149) to (156), (158), (159), (160), (164) to (184), (187), (188), (190) and (191), the number of surviving larvae on the cabbage leaves treated with each of these compounds was not greater than 10.

TEST EXAMPLE 5

Insecticidal Test Against Brown Planthoppers
(*Nilaparvata lugens*)

A formulation of a test compound obtained in Formulation Example 5 was diluted with water so that the active ingredient concentration came to 500 ppm to prepare a test spray solution.

Fifty grams of molding Bonsoru 2 (available from Sumitomo Chemical Co., Ltd.) was put into a polyethylene cup, and 10 to 15 seeds of rice were planted in the polyethylene cup. The rice plants were grown until the second foliage leaves developed and then cut into the same height of 5 cm. The test spray solution, which had been prepared as described above, was sprayed at the rate of 20 ml/cup onto these rice plants. After the chemical solution sprayed onto the rice plants was dried, thirty first-instar larvae of brown planthoppers (*Nilaparvata lugens*) were set free on the rice plants, which were then left in a greenhouse at 25° C. On the 6th day after the release of brown planthopper larvae, the number of brown planthoppers parasitic on the rice plants was examined.

As a result, in the treatment with each of the present compounds (5), (11), (21), (36), (38), (39), (55), (57), (59), (60), (61), (80), (83), (86), (87), (88), (91) to (94), (96), (97), (101), (104), (106), (109), (117), (118), (130), (147), (150), (151), (155), (167), (169), (172), (173), (174), (176), (178), (179), (181) to (185), (187), (188) and (191), the number of parasitic insects on the 6th day after the treatment was not greater than 3.

TEST EXAMPLE 6

Insecticidal Test Against Brown Planthoppers
(*Nilaparvata lugens*)

A formulation of a test compound obtained in Formulation Example 5 was diluted with water so that the active ingredient concentration came to 45.5 ppm to prepare a test spray solution.

Fifty grams of molding Bonsoru 2 (available from Sumitomo Chemical Co., Ltd.) was put into a polyethylene cup having a hole of 5 mm in diameter, and 10 to 15 seeds of rice were planted in the polyethylene cup. The rice plants were grown until the second foliage leaves developed and then treated with the test chemical solution, which had been prepared as described above and was absorbed in a volume of 55 ml from the bottom of the cup. The rice plants were left in a greenhouse at 25° C. for 6 days and then cut into the same height of 5 cm. Thirty first-instar larvae of brown planthoppers (*Nilaparvata lugens*) were set free on the rice plants, which were then left in the greenhouse at 25° C. On the 6th day after the release of brown planthopper larvae, the number of brown planthoppers parasitic on the rice plants was examined.

As a result, in the treatment with each of the present compounds (5), (55), (57), (86), (87), (101), (110), (118), (144), (151), (167), (169), (172), (173), (176), (181) and (185), the number of parasitic insects on the 6th day after the treatment was not greater than 3.

INDUSTRIAL AVAILABILITY

The present compounds have excellent pesticidal effect and they are therefore used as the active ingredients of pesticidal compositions.

The invention claimed is:

1. A 4-chloropyrimidine compound selected from the group consisting of 4-chloro-6-(2-propynyloxy)pyrimidine, 4-chloro-6-(2-butynyloxy)pyrimidine, 4-chloro-6-(1-methyl-2-butynyloxy)pyrimidine, 4-chloro-6-(2-pentynyloxy)-pyrimidine, 4-chloro -6-(2-butynyloxy)-5-methylpyrimidine, 4,5-dichloro-6-(2-butynyloxy)pyrimidine, 4-chloro-5-fluoro-6-(2-butynyloxy)pyrimidine, 4-chloro-6-(2,6-difluorobenzy)pyrimidine, 4-chloro-6-(2-fluorobenzy)pyrimidine, 4-chloro-6-(2-chlorobenzyl)pyrimidine, 4-chloro-6-(α-methylbenzyl)pyrimidine, 4-chloro-6-(2,3-difluorobenzy)pyrimidine, 4-chloro-6-(2-chloro-6-fluorobenzyl)pyrimidine, 4-chloro-6-(1-(2-fluorophenyl)ethyl) pyrimidine, 4-chloro-6-(2-chloro-3,6-difluorobenzyl) pyrimidine, 4-chloro-6-(cyclopentyloxy)pyrimidine, 4-chloro-6-(cyclohexyloxy)pyrimidine, 4-chloro-6-(trans-2-methylcyclopentyloxy)pyrimidine and 4-chloro-6-(cis-2-methylcyclohexyloxy)pyrimidine.

2. The 4-chloropyrimidine compound according to claim 1, which is selected from the group consisting of 4-chloro-6-(2-propynyloxy)pyrimidine, 4-chloro-6-(2-butynyloxy) pyrimidine, 4-chloro-6-(1-methyl-2-butynyloxy)pyrimidine, 4-chloro-6-(2-pentynyloxy)pyrimidine, 4-chloro-6-(2-butynyloxy)-5-methylpyrimidine, 4,5-dichloro-6-(2-butynyloxy)pyrimidine, and 4-chloro-5-fluoro-6-(2-butynyloxy)pyrimidine.

3. The-4-chloropyrimidine compound according to claim 1, which is selected from the group consisting of 4-chloro-6-(2,6-difluorobenzyl)pyrimidine, 4-chloro-6-(2-fluorobenzyl)pyrimidine, 4-chloro-6-(2-chlorobenzyl)pyrimidine, 4-chloro-6-(a-methylbenzyl)pyrimidine, 4-chloro-6-(2,3-difluorobenzyl)pyrimidine, 4-chloro-6-(2-chloro-6-fluorobenzyl)pyrimidine, 4-chloro-6-(1-(2-fluorophenyl)ethyl)pyrimidine, and 4-chloro-6-(2-chloro-3,6-difluorobenzyl)pyrimidine.

4. The-4-chloropyrimidine compound according to claim 1, which is selected from the group consisting of 4-chloro-6-(cyclopentyloxy)pyrimidine, 4-chloro-6-(cyclohexyloxy)pyrimidine, 4-chloro-6-(trans-2-methylcyclopentyloxy)pyrimidine and 4-chloro-6-(cis-2-methylcyclohexyloxy)pyrimidine.

* * * * *